US011551786B2

(12) United States Patent
Ellington et al.

(10) Patent No.: US 11,551,786 B2
(45) Date of Patent: Jan. 10, 2023

(54) SYSTEM AND METHOD FOR INCREASING SYNTHESIZED PROTEIN STABILITY

(71) Applicant: Board of Regents, The University of Texas System, Austin, TX (US)

(72) Inventors: Andrew Ellington, Austin, TX (US); Austin Cole, Austin, TX (US); Raghav Shroff, Austin, TX (US); Ross Thyer, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/512,116

(22) Filed: Oct. 27, 2021

(65) Prior Publication Data

US 2022/0076787 A1 Mar. 10, 2022

Related U.S. Application Data

(63) Continuation of application No. PCT/US2020/031084, filed on May 1, 2020.
(Continued)

(51) Int. Cl.
*G16B 30/00* (2019.01)
*G16B 5/00* (2019.01)
*G16B 40/00* (2019.01)

(52) U.S. Cl.
CPC .............. *G16B 30/00* (2019.02); *G16B 5/00* (2019.02); *G16B 40/00* (2019.02)

(58) Field of Classification Search
CPC ...... G06N 3/0454; G06N 20/00; G06N 3/084; G06N 3/0481; G06N 3/088; G06N 7/005;
(Continued)

(56) References Cited

U.S. PATENT DOCUMENTS 6,172,188 B1 1/2001 Thastrup
7,091,317 B2 8/2006 Stubbs
(Continued)

FOREIGN PATENT DOCUMENTS

CN 108460742 A 8/2018
WO 2017062382 A1 4/2017

OTHER PUBLICATIONS

Mura (2018) structural biology meets data science: does any thing change? Current Opinion in Structural Biology 52: 95-102. (Year: 2018).*
(Continued)

*Primary Examiner* — Mary K Zeman
(74) *Attorney, Agent, or Firm* — Riverside Law LLP

(57) ABSTRACT

A computer-implemented method of training a neural network to improve a characteristic of a protein comprises collecting a set of amino acid sequences from a database, compiling each amino acid sequence into a three-dimensional crystallographic structure of a folded protein, training a neural network with a subset of the three-dimensional crystallographic structures, identifying, with the neural network, a candidate residue to mutate in a target protein, and identifying, with the neural network, a predicted amino acid residue to substitute for the candidate residue, to produce a mutated protein, wherein the mutated protein demonstrates an improvement in a characteristic over the target protein. A system for improving a characteristic of a protein is also described. Improved blue fluorescent proteins generated using the system are also described.

26 Claims, 17 Drawing Sheets

Specification includes a Sequence Listing.

Related U.S. Application Data

(60) Provisional application No. 62/841,906, filed on May 2, 2019.

(58) Field of Classification Search
CPC .......... G06N 20/10; G06N 3/08; G06N 5/003;
G06N 3/04; G06N 5/04; G06N 20/20;
G06N 3/0445; G06N 5/046; G06N 3/02;
G06N 7/00; G06N 3/10; G06N 5/022;
G16B 40/00; G16B 15/30; G16B 40/20;
G16B 15/20; G16B 15/00; G16B 20/00;
G16B 20/50; G16B 40/30; G16B 5/00;
G16B 5/20; G16B 5/30; G16B 50/00;
G16B 50/10; G16B 50/20; G16B 50/30;
G16B 45/00; G06K 9/6272; G06K
9/6267; G06K 9/6256; G06K 9/6218;
G06K 9/6232; G06K 9/6262; G06K
9/6268; G06K 9/6277; G06K 9/628;
G06K 9/627; G06K 9/6251; G16C 20/70;
G16C 20/30; G16C 20/50; G06T 15/08;
G06T 2200/04; G06T 2207/20084; G06T
7/60; G06T 15/10; G06T 2207/20081;
G06T 2207/20; G06T 15/00; G06T 17/00;
G06T 19/00; G06T 19/003; G06T 19/20;
G06T 2219/2004; G06T 2219/2016;
G06T 2219/2021; G06F 16/58; G06F
16/907; G06F 30/27; G06F 17/16; G06F
2119/18; G06F 30/20; G06F 16/5854;
G06F 16/56; G06F 16/23; G06V 10/774;
G06V 10/776; G06V 10/82; G01N
23/201; G01N 2333/435; G01N
2021/1785; G01N 23/20
See application file for complete search history.

(56) References Cited

U.S. PATENT DOCUMENTS

| | | | |
|---|---|---|---|
| 9,354,175 | B2 | 5/2016 | Auldridge |
| 2005/0251872 | A1 | 11/2005 | Bear |
| 2008/0215301 | A1 | 9/2008 | Eyal |
| 2011/0301331 | A1 | 12/2011 | Glaser |
| 2014/0286881 | A1 | 9/2014 | Bridgeman |
| 2016/0147936 | A1 | 5/2016 | Vendruscolo |
| 2017/0211206 | A1 | 7/2017 | Cope |

OTHER PUBLICATIONS

Todor K. Avramov and Dong Si. 2018. Deep Learning for Resolution Validation of Three Dimensional Cryo-Electron Microscopy Density Maps. In Proceedings of ACM Conference on Bioinformatics, Computational Biology, and Health Informatics (ACM-BCB 2018). Washington, DC, USA, 2018 6 pages. (Year: 2018).*

DeJesus et al. Capsule networks for protein structure classification and prediction. arXiv Aug. 22, 2018. 12 pages. (Year: 2018).*

Gomes et al. Atomic convolutional netowkrs for predicting protein-ligand binding affinity. arXiv Mar. 30, 2017, 17 pages. (Year: 2017).*

Pu, et al. DeepDrug3D: classification of ligand binding pockets in proteins with a convolutional neural network. (Feb. 2, 2019) PLOS Computational Biology, e1006718, 23 pages. (Year: 2019).*

Alford, R. F., Leaver-Fay, A., Jeliazkov, J. R., O'Meara, M. J., DiMaio, F. P., Park, H., . . . & Labonte, J. W. (2017). The Rosetta all-atom energy function for macromolecular modeling and design. Journal of chemical theory and computation , 13 (6), 3031-3048.

Costantini, L. M., Subach, O. M., Jaureguiberry-Bravo, M., Verkhusha, V. V., & Snapp, E. L. (2013). Cysteineless non-glycosylated monomeric blue fluorescent protein, secBFP2, for studies in the eukaryotic secretory pathway. Biochemical and biophysical research communications, 430(3), 1114-1119.

International Search Report and Written Opinion for App. No. PCT/US2020/031084, dated Feb. 1, 2021, 18 pages.

Ragoza, M., Hochuli, J., Idrobo, E., Sunseri, J., & Koes, D. R. (2017). Protein-Ligand scoring with Convolutional neural networks. Journal of chemical information and modeling , 57 (4), 942-957.

Subach, O. M., Cranfill, P. J., Davidson, M. W., & Verkhusha, V. V. (2011). An enhanced monomeric blue fluorescent protein with the high chemical stability of the chromophore. PloS one, 6(12), e28674.

Subach, O. M., Gundorov, I. S., Yoshimura, M., Subach, F. V., Zhang, J., Gruenwald, D., . . . & Verkhusha, V. V. (2008). Conversion of red fluorescent protein into a bright blue probe. Chemistry & biology, 15(10), 1116-1124.

Torng, W., & Altman, R. B. (2017). 3D deep convolutional neural networks for amino acid environment similarity analysis. BMC bioinformatics , 18 (1), 302.

Wallach, I., Dzamba, M., & Heifets, A. (2015). AtomNet: A deep convolutional neural network for bioactivity prediction in structure-based drug discovery. arXiv preprint arXiv:1510.02855.

\* cited by examiner

SYSTEM AND METHOD FOR INCREASING SYNTHESIZED PROTEIN STABILITY

RELATED APPLICATIONS

The present application claims the benefit of and priority to P.C.T. Application No. PCT/US2020/031084, entitled "System and Method for Increasing Synthesized Protein Stability," filed May 1, 2020, which claims priority to U.S. Provisional Patent Application No. 62/841,906, entitled "System and Method for Increasing Synthesized Protein Stability," filed May 2, 2019, the entirety of each of which are incorporated by reference herein.

STATEMENT REGARDING FEDERALLY SPONSORED RESEARCH OR DEVELOPMENT

This invention was made with government support under Grant no. R43 NS105463 awarded by the National Institutes of Health, and Grant no. FA9550-14-1-0089 awarded by the Air Force Office of Scientific Research. The government has certain rights in the invention.

BACKGROUND

Protein engineering is a transformative approach in biotechnology and biomedicine aimed at either imparting novel functionality on existing proteins or making proteins more persistent in non-native environments. A design consideration that influences both manners of engineering is the overall stability of the protein. In the former case, gain-of-function mutations are introduced that expand the role of a protein through rational design or directed evolution, frequently at a thermodynamic cost. As most natural proteins are only marginally stable, functional mutations that destabilize a protein to the point of unfolding may be missed, while increasing stability before a selection has been shown to promote the evolvability of a protein.

A significant barrier in the translation from useful naturally occurring biocatalyst to industrial use is the adaptation of a protein to radically different environmental conditions, temperature, and solvents. Increasing the stability of a protein can alleviate many of these pressures to allow for large quantity expression with higher yields and lower cost. Thus, stabilization is critical to the success of many protein engineering efforts.

Numerous methods exist to engineer proteins, and all generally represent a compromise between how quickly and accurately protein variants can be measured, and how efficiently the landscape of protein variants can be sampled. Techniques such as mutagenic Polymerase Chain Reaction (PCR) require minimal knowledge about the relationship between sequence and function, yet rely on high-throughput screens or selections to segregate large libraries of protein variants. Structural data and computational approaches can be used to narrow the search space, and concomitantly reduce the amount of downstream characterization. These tools become increasingly important for proteins where the desired properties are difficult to measure, especially at scale. However, due to our incomplete understanding of protein sequence/structure/function relationships, different computational tools for protein engineering will often provide completely different or even conflicting solutions. This is especially true for properties such as stability and folding, which are often the result of many small interactions distributed throughout the entire protein sequence.

Typically, computational methods will identify residues that destabilize a protein by performing computationally intensive folding simulations. The level of detail involved in these simulations varies—some go as far as invoking quantum mechanics (MOE) to explain molecular interactions while others use more coarse grained methods (Rosetta). To a first approximation, coarse grained approaches identify problematic residues by either looking for gaps in a protein structure (RosettaVIP), doing fast local free energy calculations (foldX), or finding residues that are evolutionary outliers (PROSS). A better fitting residue is then suggested by hydrophobic packing or reversion to evolutionary consensus. Then, the effect of these substitutions on stability of a protein is estimated via energetic simulation of the mutant. In total, this process (residue identification, substitution suggestion, refolding & free energy calculations) can take anywhere from several hours to days.

Machine learning is an attractive alternative as it requires no foreknowledge about particular protein features or time-consuming manual inspection and assignment of individual structural features. Recently, Torng and Altman (Torng et al., "3D deep convolutional neural networks for amino acid environment similarity analysis," *BMC Bioinformatics*, 18:302, 2017, incorporated herein by reference) described a general framework that applies 3D convolutional neural networks (3DCNN) to protein structural analysis by predicting the identity of amino acids given information about the surrounding protein microenvironment. This neural network achieved 42% predictive accuracy in assigning amino acids relative to the wild-type sequence, and outperformed other computational methods which relied on identifying pre-assigned structure-based features. Furthermore, given structural data for a model protein, T4 lysozyme, the 3D CNN typically predicted the wild-type residue at locations where mutations are known to be destabilizing, and displayed a strong preference for the wild-type residue when given the structures of these known destabilizing mutants.

SUMMARY

Given that the proteome must simultaneously exhibit several unrelated or even conflicting phenotypes like folding geometry, stability, catalysis, and binding specificity, it is plausible that amino acids which are structural outliers at locations away from the active site might affect folding and stability, but not function. Therefore, there is a need in the art for an improved protein engineering technique that leverages artificial intelligence to learn the consensus microenvironments for the different amino acids and scans entire structures to identify residues which deviate from the structural consensus. These residues, considered to have a low probability of wild-type, are thought to be loci of instability, and as such are good candidates for mutagenesis and stability engineering. Implementations of the systems and methods discussed herein provide such improved protein engineering techniques.

In one aspect, a computer-implemented method of training a neural network to improve a characteristic of a protein comprises collecting a set of amino acid sequences from a database, compiling a set of three-dimensional crystallographic structures having chemical environments for the set of amino acids, translating the chemical environments into voxelized matrices, training a neural network with a subset of the voxelized matrices, identifying, with the neural network, a candidate residue to mutate in a target protein, and identifying, with the neural network, a predicted amino acid residue to substitute for the candidate residue, to produce a mutated protein, wherein the mutated protein demonstrates an improvement in a characteristic over the target protein. In one embodiment, the method further comprises the step of adding the spatial arrangement of a feature selected from the group consisting of hydrogen location, partial charges, beta factors, secondary structure, aromaticity, electron density, polarity and combinations thereof to at least one of the three-dimensional crystallographic structures.

In one embodiment, the method further comprises adjusting the set of amino acid sequences to reflect their natural frequencies. In one embodiment, the method further comprises sampling at least 50% of the amino acids in the set of amino acid sequences from a random location in the sequence. In one embodiment, the method further comprise training a second independent neural network with a second subset of three-dimensional crystallographic structures or voxelized matrices, and identifying candidate and predicted residues based on the results of both neural networks. In one embodiment, the characteristic is stability, maturation, folding, or combinations thereof.

In another aspect, a system for improving a characteristic of a protein comprises a processor and a non-transitory computer-readable medium with instructions stored thereon, that when executed by the processor perform steps comprising providing a target protein comprising a sequence of residues, providing a set of three-dimensional models surrounding an amino acid and a set of protein characteristic values for each three dimensional model, estimating a set of parameters at various points in each three dimensional model, training a neural network with the three dimensional models, the parameters, and the protein characteristic values, identifying, with the neural network, a candidate residue to mutate in the target protein, and identifying, with the neural network, a predicted amino acid residue to substitute for the candidate residue, producing a mutated protein, wherein the mutated protein demonstrates an improvement in the characteristic over the target protein.

In one embodiment, the protein characteristic is stability. In one embodiment, the steps include recompiling at least one amino acid sequence of the folded amino acid sequences to produce an updated three-dimensional model. In one embodiment, the steps include adding a spatial arrangement of a feature to at least one amino acid sequence of the folded amino acid sequences before recompilation.

In another aspect, the invention relates to a protein comprising a secBFP2 variant having one or more mutations at one more residues selected from: T18, S28, Y96, S114, V124, T127, D151, N173, and R198, in relation to full-length wild-type secBFP2. In one embodiment, the protein comprises a secBFP2 variant comprising an amino acid sequence of one of SEQ ID NO:2 to SEQ ID NO:28. In one embodiment, the secBFP2 variant comprises a variant of an amino acid sequence of one of SEQ ID NO:2 to SEQ ID NO:28. In one embodiment, the secBFP2 variant comprises a fusion protein comprising an amino acid sequence of one of SEQ ID NO:2 to SEQ ID NO:28. In one embodiment, the BFP comprises a fragment of an amino acid sequence of one of SEQ ID NO:2 to SEQ ID NO:28.

In another aspect, the invention relates to a nucleic acid molecule comprising a nucleotide sequence encoding a protein comprising the secBFP2 variant. In one embodiment, the nucleotide sequence encodes an amino acid sequence as set forth in SEQ ID NO:2 to SEQ ID NO:28, a variant thereof, a fusion protein thereof or a fragment thereof. In one embodiment, the molecule is a plasmid. In one embodiment, the molecule is an expression vector. In one embodiment, the nucleic acid molecule further comprises a multiple cloning site for insertion of a heterologous protein encoding sequence. In another aspect, the present invention includes a composition comprising a protein as described above, a composition comprising a nucleic acid molecule as described above, a kit comprising a protein as described above, or a nucleic acid molecule as described above.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which.

DETAILED DESCRIPTION

Figure 1A:
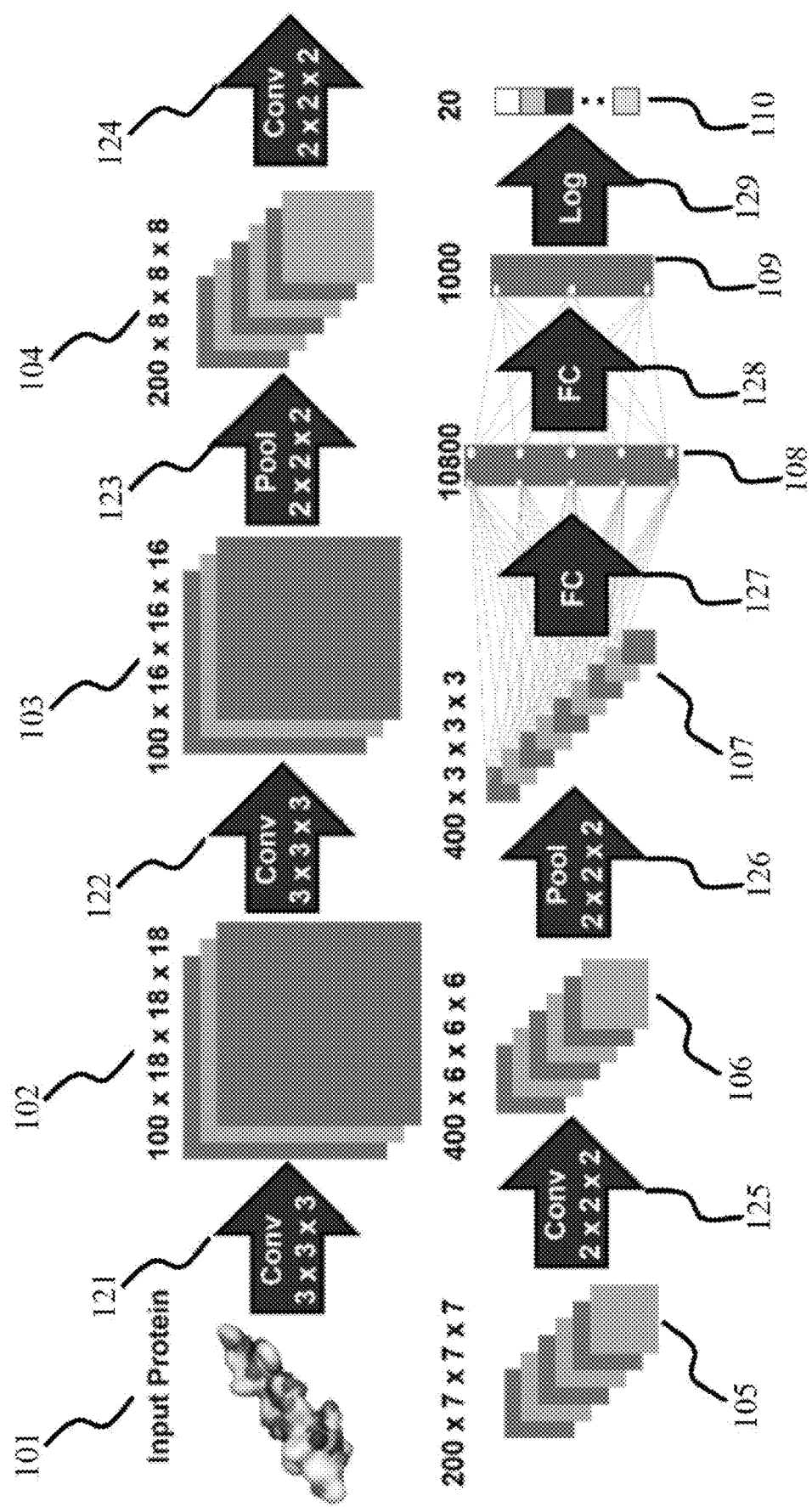
FIG. 1A is a diagram of an implementation of a computer-implemented neural network for increasing synthesized protein characteristics.

It is to be understood that the figures and descriptions of the present invention have been simplified to illustrate elements that are relevant for a clear understanding of the present invention, while eliminating, for the purpose of clarity, many other elements found in related systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The term "nucleic acid molecule" or "polynucleotide" refers to a deoxyribonucleotide or ribonucleotide polymer in either single-stranded or double-stranded form, and, unless specifically indicated otherwise, encompasses polynucleotides containing known analogs of naturally occurring nucleotides that can function in a similar manner as naturally occurring nucleotides. It will be understood that when a nucleic acid molecule is represented by a DNA sequence, this also includes RNA molecules having the corresponding RNA sequence in which "U" (uridine) replaces "T" (thymidine).

The term "recombinant nucleic acid molecule" refers to a non-naturally occurring nucleic acid molecule containing two or more linked polynucleotide sequences. A recombinant nucleic acid molecule can be produced by recombination methods, particularly genetic engineering techniques, or can be produced by a chemical synthesis method. A recombinant nucleic acid molecule can encode a fusion protein, for example, a fluorescent protein variant suggested by the systems and methods discussed herein linked to a polypeptide of interest. The term "recombinant host cell" refers to a cell that contains a recombinant nucleic acid molecule. As such, a recombinant host cell can express a polypeptide from a "gene" that is not found within the native (non-recombinant) form of the cell.

Reference to a polynucleotide "encoding" a polypeptide means that, upon transcription of the polynucleotide and translation of the mRNA produced therefrom, a polypeptide is produced. The encoding polynucleotide is considered to include both the coding strand, whose nucleotide sequence is identical to an mRNA, as well as its complementary strand. It will be recognized that such an encoding polynucleotide is considered to include degenerate nucleotide sequences, which encode the same amino acid residues. Nucleotide sequences encoding a polypeptide can include polynucleotides containing introns as well as the encoding exons.

The term "expression control sequence" refers to a nucleotide sequence that regulates the transcription or translation of a polynucleotide or the localization of a polypeptide to which to which it is operatively linked. Expression control sequences are "operatively linked" when the expression control sequence controls or regulates the transcription and, as appropriate, translation of the nucleotide sequence (i.e., a transcription or translation regulatory element, respectively), or localization of an encoded polypeptide to a specific compartment of a cell. Thus, an expression control sequence can be a promoter, enhancer, transcription terminator, a start codon (ATG), a splicing signal for intron excision and maintenance of the correct reading frame, a STOP codon, a ribosome binding site, or a sequence that targets a polypeptide to a particular location, for example, a cell compartmentalization signal, which can target a polypeptide to the cytosol, nucleus, plasma membrane, endoplasmic reticulum, mitochondrial membrane or matrix, chloroplast membrane or lumen, medial trans-Golgi cisternae, or a lysosome or endosome. Cell compartmentalization domains include, for example, a peptide containing amino acid residues 1 to 81 of human type II membrane-anchored protein galactosyltransferase, or amino acid residues 1 to 12 of the presequence of subunit IV of cytochrome c oxidase (see, also, Hancock et al., EMBO J. 10:4033-4039, 1991; Buss et al., Mol. Cell. Biol. 8:3960-3963, 1988; U.S. Pat. No. 5,776,689, each of which is incorporated herein by reference).

The term "operatively linked" or "operably linked" or "operatively joined" or the like, when used to describe chimeric proteins, refer to polypeptide sequences that are placed in a physical and functional relationship to each other. In a most preferred embodiment, the functions of the polypeptide components of the chimeric molecule are unchanged compared to the functional activities of the parts in isolation. For example, a fluorescent protein suggested by the systems and methods discussed herein can be fused to a polypeptide of interest. In this case, it is preferable that the fusion molecule retains its fluorescence, and the polypeptide of interest retains its original biological activity. In some embodiments of the systems and methods discussed herein, the activities of either the fluorescent protein or the protein of interest can be reduced relative to their activities in isolation. Such fusions can also find use with the systems and methods discussed herein.

The term "label" refers to a composition that is detectable with or without the instrumentation, for example, by visual inspection, spectroscopy, or a photochemical, biochemical, immunochemical or chemical reaction. Useful labels include, for example, phosphorus-32, a fluorescent dye, a fluorescent protein, an electron-dense reagent, an enzyme (such as is commonly used in an ELISA), a small molecule such as biotin, digoxigenin, or other haptens or peptide for which an antiserum or antibody, which can be a monoclonal antibody, is available. It will be recognized that a fluorescent protein variant suggested by implementations of the systems and methods discussed herein, which is itself a detectable protein, can nevertheless be labeled so as to be detectable by a means other than its own fluorescence, for example, by incorporating a radionuclide label or a peptide tag into the protein so as to facilitate, for example, identification of the protein during its expression and isolation of the expressed protein, respectively. A label useful for purposes of implementations of the systems and methods discussed herein generally generates a measurable signal such as a radioactive signal, fluorescent light, enzyme activity, and the like, either of which can be used, for example, to quantitate the amount of the fluorescent protein variant in a sample.

The term "polypeptide" or "protein" refers to a polymer of two or more amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "isolated" or "purified" refers to a material that is substantially or essentially free from components that normally accompany the material in its native state in nature. Purity or homogeneity generally are determined using analytical chemistry techniques such as polyacrylamide gel electrophoresis, high performance liquid chromatography, and the like. A polynucleotide or a polypeptide is considered to be isolated when it is the predominant species present in a preparation. Generally, an isolated protein or nucleic acid molecule represents greater than 80% of the macromolecular species present in a preparation, often represents greater than 90% of all macromolecular species present, usually represents greater than 95%, of the macromolecular species, and, in particular, is a polypeptide or polynucleotide that purified to essential homogeneity such that it is the only species detected when examined using conventional methods for determining purity of such a molecule.

The term "naturally-occurring" is used to refer to a protein, nucleic acid molecule, cell, or other material that occurs in nature. For example, a polypeptide or polynucleotide sequence that is present in an organism, including in a virus. A naturally occurring material can be in its form as it exists in nature, and can be modified by the hand of man such that, for example, is in an isolated form.

The term "antibody" refers to a polypeptide substantially encoded by an immunoglobulin gene or immunoglobulin genes, or antigen-binding fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist as intact immunoglobulins and as well characterized antigen-binding fragments of an antibody, which can be produced by digestion with a peptidase or can using recombinant DNA methods. Such antigen-binding fragments of an antibody include, for example, Fv, Fab' and F(ab)'2 fragments. The term "antibody," as used herein, includes antibody fragments either produced by the modification of whole antibodies or those synthesized de novo using recombinant DNA methodologies. The term "immunoassay" refers to an assay that utilizes an antibody to specifically bind an analyte. An immunoassay is characterized by the use of specific binding properties of a particular antibody to isolate, target, and/or quantify the analyte.

The term "identical," when used in reference to two or more polynucleotide sequences or two or more polypeptide sequences, refers to the residues in the sequences that are the same when aligned for maximum correspondence. When percentage of sequence identity is used in reference to a polypeptide, it is recognized that one or more residue positions that are not otherwise identical can differ by a conservative amino acid substitution, in which a first amino acid residue is substituted for another amino acid residue having similar chemical properties such as a similar charge or hydrophobic or hydrophilic character and, therefore, does not change the functional properties of the polypeptide. Where polypeptide sequences differ in conservative substitutions, the percent sequence identity can be adjusted upwards to correct for the conservative nature of the substitution. Such an adjustment can be made, for example, by scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions can be calculated using, for example, the algorithms discussed in Meyers and Miller, Comp. Appl. Biol. Sci. 4:11-17, 1988; Smith and Waterman, Adv. Appl. Math. 2:482, 1981; Needleman and Wunsch, J. Mol. Biol. 48:443, 1970; Pearson and Lipman, Proc. Natl. Acad. Sci., USA 85:2444 (1988); Higgins and Sharp, Gene 73:237-244, 1988; Higgins and Sharp, CABIOS 5:151-153; 1989; Corpet et al., Nucl. Acids Res. 16:10881-10890, 1988; Huang, et al., Comp. Appl. Biol. Sci. 8:155-165, 1992; Pearson et al., Meth. Mol. Biol., 24:307-331, 1994, each of which is incorporated by reference herein. Alignment also can be performed by simple visual inspection and manual alignment of sequences.

The term "conservatively modified variation," when used in reference to a particular polynucleotide sequence, refers to different polynucleotide sequences that encode identical or essentially identical amino acid sequences, or where the polynucleotide does not encode an amino acid sequence, to essentially identical sequences. Because of the degeneracy of the genetic code, a large number of functionally identical polynucleotides encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleotide sequence variations are "silent variations," which can be considered a species of "conservatively modified variations." As such, it will be recognized that each polynucleotide sequence disclosed herein as encoding a fluorescent protein variant also describes every possible silent variation. It will also be recognized that each codon in a polynucleotide, except AUG, which is ordinarily the only codon for methionine, and UUG, which is ordinarily the only codon for tryptophan, can be modified to yield a functionally identical molecule by standard techniques. Accordingly, each silent variation of a polynucleotide that does not change the sequence of the encoded polypeptide is implicitly described herein. Furthermore, it will be recognized that individual substitutions, deletions or additions that alter, add or delete a single amino acid or a small percentage of amino acids (typically less than 5%, and generally less than 1%) in an encoded sequence can be considered conservatively modified variations, provided alteration results in the substitution of an amino acid with a chemically similar amino acid. Conservative amino acid substitutions providing functionally similar amino acids may include the following six groups, each of which contains amino acids that are considered conservative substitutes for each another.

1) Alanine (Ala, A), Serine (Ser, S), Threonine (Thr, T);
2) Aspartic acid (Asp, D), Glutamic acid (Glu, E);
3) Asparagine (Asn, N), Glutamine (Gln, Q);
4) Arginine (Arg, R), Lysine (Lys, K):
5) Isoleucine (Ile, I), Leucine (Leu, L), Methionine (Met, M), Valine (Val, V); and
6) Phenylalanine (Phe, F), Tyrosine (Tyr, Y), Tryptophan (Trp, W).

Two or more amino acid sequences or two or more nucleotide sequences are considered to be "substantially identical" or "substantially similar" if the amino acid sequences or the nucleotide sequences share at least 80% sequence identity with each other, or with a reference sequence over a given comparison window. Thus, substantially similar sequences include those having, for example, at least 85% sequence identity, at least 90% sequence identity, at least 95% sequence identity, or at least 99% sequence identity.

A subject nucleotide sequence is considered "substantially complementary" to a reference nucleotide sequence if the complement of the subject nucleotide sequence is substantially identical to the reference nucleotide sequence.

Fluorescent molecules are useful in fluorescence resonance energy transfer, FRET, which involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should be as high as possible to maximize RO, which represents the distance at which energy transfer efficiency is 50%. However, the excitation spectra of the donor and acceptor should overlap as little as possible so that a wavelength region can be found at which the donor can be excited efficiently without directly exciting the acceptor because fluorescence arising from direct excitation of the acceptor can be difficult to distinguish from fluorescence arising from FRET. Similarly, the emission spectra of the donor and acceptor should overlap as little as possible so that the two emissions can be clearly distinguished. High fluorescence quantum yield of the acceptor moiety is desirable if the emission from the acceptor is to be measured either as the sole readout or as part of an emission ratio. One factor to be considered in choosing the donor and acceptor pair is the efficiency of fluorescence resonance energy transfer between them. Preferably, the efficiency of FRET between the donor and acceptor is at least 10%, more preferably at least 50% and even more preferably at least 80%.

The term "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between a wild type or parental fluorescent protein and a spectral variant, or a mutant thereof, is useful. A measurable difference can be determined by determining the amount of any quantitative fluorescent property, e.g., the amount of fluorescence at a particular wavelength, or the integral of fluorescence over the emission spectrum. Determining ratios of excitation amplitude or emission amplitude at two different wavelengths ("excitation amplitude ratioing" and "emission amplitude ratioing," respectively) are particularly advantageous because the ratioing process provides an internal reference and cancels out variations in the absolute brightness of the excitation source, the sensitivity of the detector, and light scattering or quenching by the sample. As used herein, the term "fluorescent protein" refers to any protein that can fluoresce when excited with an appropriate electromagnetic radiation, except that chemically tagged proteins, wherein the fluorescence is due to the chemical tag, and polypeptides that fluoresce only due to the presence of certain amino acids such as tryptophan or tyrosine, whose emission peaks at ultraviolet wavelengths (i.e., less that about 400 nm) are not considered fluorescent proteins for purposes of implementations of the systems and methods discussed herein. In general, a fluorescent protein useful for preparing a composition of implementations of the systems discussed herein or for use in an implementation of a method discussed herein is a protein that derives its fluorescence from autocatalytically forming a chromophore. A fluorescent protein can contain amino acid sequences that are naturally occurring or that have been engineered (i.e., variants or mutants). When used in reference to a fluorescent protein, the term "mutant" or "variant" refers to a protein that is different from a reference protein.

The term "blue fluorescent protein" is used broadly herein to refer to a protein that fluoresces blue light. The term "blue fluorescent protein," or "BFP" is used in the broadest sense and specifically covers mTagBFP, secBFP2, and blue fluorescent proteins from any species, as well as variants thereof as long as they retain the ability to fluoresce blue light.

The term "mutant" or "variant" is used herein in reference to a fluorescent protein that contains a mutation with respect to a corresponding wild type or parental fluorescent protein. In addition, reference is made herein to a "spectral variant" or "spectral mutant" of a fluorescent protein to indicate a mutant fluorescent protein that has a different fluorescence characteristic with respect to the corresponding wild type fluorescent protein.

Throughout this disclosure, various aspects of implementations of the systems and methods discussed herein can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

In some aspects of the systems and methods discussed herein, software executing the instructions provided herein may be stored on a non-transitory computer-readable medium, wherein the software performs some or all of the steps of implementations of the methods discussed herein when executed on a processor.

Aspects of the systems and methods discussed herein relate to algorithms executed in computer software. Though certain embodiments may be described as written in particular programming languages, or executed on particular operating systems or computing platforms, it is understood that implementations of the systems and methods discussed herein are not limited to any particular computing language, platform, or combination thereof. Software executing the algorithms described herein may be written, compiled, or interpreted in any programming language, including but not limited to C, C++, C#, Objective-C, Java, JavaScript, Python, PHP, Perl, Ruby, or Visual Basic. It is further understood that elements of the systems and methods discussed herein may be executed on any acceptable computing platform, including but not limited to a server, a cloud instance, a workstation, a thin client, a mobile device, an embedded microcontroller, a television, or any other suitable computing device.

Parts of implementations of the systems discussed herein are described as software running on a computing device. Though software described herein may be disclosed as operating on one particular computing device (e.g., a dedicated server or a workstation), software may be intrinsically portable and software running on a dedicated server may also be run, for the purposes of implementations of the systems and methods discussed herein, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device.

Similarly, parts of implementations of the systems discussed herein are described as communicating over a variety of wireless or wired computer networks. For the purposes of implementations of the systems and methods discussed herein, the words "network," "networked" and "networking" are understood to encompass wired Ethernet, fiber optic connections, wireless connections including any of the various 802.11 standards, cellular WAN infrastructures such as 3G, 4G/LTE, or 5G networks, Bluetooth®, Bluetooth® Low Energy (BLE) or Zigbee® communication links, or any other method by which one electronic device is capable of communicating with another. In some embodiments, elements of the networked portion of implementations of the systems discussed herein may be implemented over a Virtual Private Network (VPN).

Aspects of implementations of the systems and methods discussed herein relate to a machine learning algorithm, machine learning engine, or neural network. A neural network may be trained based on various attributes of a protein, for example atomic environments of amino acids within known proteins, and may output a proposed change to one or more amino acids in the protein based on the attributes. In some embodiments, attributes may include atom types, electrostatics, beta factors, solvent accessibility, secondary structure, aromaticity, or polarity. The resulting amino acids may then be judged according to one or more quality metrics, and the weights of the attributes may be optimized to maximize the quality metrics. In this manner, a neural network can be trained to predict and optimize for any quality metric that can be experimentally measured. Examples of quality metrics that a neural network can be trained on include wild type amino acid accuracy, known stabilizing/destabilizing positions, accuracy of amino acid groups, and any other suitable type of quality metric that can be measured. In some embodiments, the neural network may have multi-task functionality and allow for simultaneous prediction and optimization of multiple quality metrics.

In embodiments that implement such a neural network, a query may be performed in various ways. A query may request the neural network to identify amino acids within a given protein to increase a desirable parameter, for example protein stability, which may be embodied thermally through melt curves or chemically with guanidine or urea denaturation. A neural network of implementations of the systems and methods discussed herein may identify one or more amino acid residues of a protein whose predicted identity (as evaluated by the neural network) differs from its native identity, thereby indicating that an improved protein may be generated by mutating the native amino acid residue to the predicted amino acid residue. As contemplated herein, a predicted amino acid residue may be any natural or unnatural (e.g., artificial or synthetic) amino acid.

In some embodiments, the neural network may be updated by training the neural network using a value of the desirable parameter associated with an input amino acid sequence or residue. Updating the neural network in this manner may improve the ability of the neural network in proposing optimal amino acid residues. In some embodiments, training the neural network may include using a value of the desirable parameter associated with a protein mutated at a predicted amino acid residue. For example, in some embodiments, training the neural network may include predicting a value of the desirable parameter for the proposed amino acid, comparing the predicted value to a corresponding value of a parameter associated with a known amino acid, and training the neural network based on a result of the comparison. If the predicted value is the same or substantially similar to the known value, then the neural network may be minimally updated or not updated at all. If the predicted value differs from that of the known amino acid, then the neural network may be substantially updated to better correct for this discrepancy. Regardless of how the neural network is retrained, the retrained neural network may be used to propose additional amino acids.

Although the techniques of the present application are in the context of increasing protein stability, it should be appreciated that this is a non-limiting application of these techniques as they can be applied to other types of protein parameters or attributes, for example half-life, activity, degradation resistance, solubility, thermostability, post-translational modifications, expanded pH tolerance, decreased maturation time, nucleic acid binding, protein-protein interactions, hydrophobicity, or combinations thereof. Depending on the type of data used to train the neural network, the neural network can be optimized for different types of proteins, protein-protein interactions, and/or attributes of a protein. In this manner, a neural network can be trained to improve identification of an amino acid sequence, which can also be referred to as a peptide, for a protein. Querying the neural network may include inputting an initial amino acid sequence for a protein. The neural network may have been previously trained using different amino acid sequences. The query to the neural network may be for a proposed amino acid sequence for a protein of a higher stability than the initial amino acid sequence. A proposed amino acid sequence indicating a specific amino acid for each residue of the proposed amino acid sequence may be received from the neural network.

The techniques described herein associated with iteratively querying a neural network by inputting a sequence having a discrete representation, receiving an output from the neural network that has a continuous representation, and discretizing the output before successively providing it as an input to the neural network, can be applied to other machine learning applications. Such techniques may be particularly useful in applications where a final output having a discrete representation is desired. Such techniques can be generalized for identifying a series of discrete attributes by applying a model generated by a neural network trained using data relating the discrete attributes to a characteristic of a series of the discrete attributes. In the context of identifying an amino acid in a sequence, the discrete attributes may include different amino acids.

In some embodiments, the model may receive as an input an initial series having a discrete attribute located at each position of the series, including, but not limited, to data resulting from molecular simulations. Each of the discrete attributes within the initial series is one of a plurality of discrete attributes. Querying the neural network may include inputting the initial series of discrete attributes and generating an output series of discrete attributes having a level of a characteristic that differs from a level of the characteristic for the initial series. In response to querying the neural network, an output series and values associated with different discrete attributes for each position of the output series may be received from the neural network. For each position of the series, the values for each discrete attribute may correspond to predictions of the neural network regarding levels of the characteristic if the discrete attribute is selected for the position and form a continuous value data set. The values may range across the discrete attributes for a position, and may be used in identifying a discrete version of the output series. In some embodiments, identifying the discrete version of the output series may include selecting, for each position of the series, the discrete attribute having the highest value from among the values for the different discrete attributes for the position. A proposed series of discrete attributes may be received as an output of identifying the discrete version.

In some embodiments, an iterative process is formed by querying the neural network for an output series, receiving the output series, and identifying a discrete version of the output series. An additional iteration of the iterative process may include inputting the discrete version of the output series from an immediately prior iteration. The iterative process may stop when a current output series matches a prior output series from the immediately prior iteration.

In some embodiments, a proposed amino acid sequence having desired values for multiple quality metrics (e.g., values higher than values for another sequence) is identified, rather than a desired value for a single quality metric, including for training a neural network to identify an amino acid sequence with multiple quality metrics. Such techniques may be particularly useful in applications where identification of a proposed amino acid sequence for a protein having different characteristics is desired. In implementations of such techniques, the training data may include data associated with the different characteristics for each of the amino acid sequences used to train a neural network. A model generated by training the neural network may have one or more parameters corresponding to different combinations of the characteristics. In some embodiments, a parameter may represent a weight between a first characteristic and a second characteristic, which may be used to balance a likelihood that a proposed amino acid sequence has the first characteristic in comparison to the second characteristic. In some embodiments, training the neural network includes assigning scores for different characteristics, and the scores may be used to estimate values for parameters of the model that are used to predict a proposed amino acid sequence. Training data in some such embodiments may include amino acid sequences associated atomic microenvironments, which when used to train a neural network generates a model used to predict a proposed amino acid sequence. Training the neural network may involve assigning scores, and a value for the parameter may be estimated using the scores.

Biological applications for convolutional neural networks are relatively scarce. Rather than being analyzed as amino acid sequences, proteins, are increasingly being evaluated in their crystallized form to solve their three-dimensional structure. One aspect of implementations of the methods discussed herein involves training a 3D convolutional neural network that characterizes chemical environments unique to each of the 20 amino acids. The same neural network can then predict the amino acid best fitting a given environment. The neural network described herein has been trained on 1.6 million amino acid environments across 19,000 phylogenetically distant protein structures. Following training, this network's in sample accuracy is 80.0% and out of sample accuracy is 72.5%, a roughly 20 to 30% improvement on the state of the art (approximately 40% out of sample accuracy).

Sites with large discrepancies between the expected amino acid and observed amino acid present targets to engineer protein features like stability and folding maturation. The systems and methods described herein experimentally characterized three biological cases—a beta—lactamase antibiotic marker, a coral derived blue fluorescent protein, and phosphomannose isomerase from the yeast *Candida albicans*—where predictions from the neural network demonstrate increased protein function and stability in vivo. These results forecast new biological tools at the intersection of AI and molecular biology.

In one embodiment, implementations of the methods discussed herein utilize a neural network, for example implementations of the neural network published by Torng and Altman, referenced above. Implementations of the systems and methods discussed herein improve substantially on the published neural network design, as the experimental results discussed below show. The original Torng and Altman sets contained 3696 training and 194 test protein families, resulting in 32,760 training and 1601 test structures.

Implementations of the systems and methods discussed herein build on the Torng and Altman framework to address the problem of protein stabilization. In a basic example, crystal structures of a protein are treated like a 3D image. In any given image there are a many observations of individual amino acids and their atomic environments. Some methods center a consistent frame of reference on one of these amino acids. From this vantage, oxygen, nitrogen, sulfur, and carbon atoms are separated inside a 20×20×20 angstrom box and all atoms associated with the central amino acid are removed. This set of environments and the amino acid fitting in the environment may then be used as an annotated training set for a 3D convolutional neural network. With this trained neural network, experimentally introduced destabilizing mutations can be detected.

Implementations of the systems and methods discussed herein improve on the basic model to identify novel stabilizing mutations. The improvements described herein render the quality of predictions sufficient for not only justifying known destabilizing mutations, but also identifying unknown destabilizing residues and suggesting a stabilizing mutation.

In some implementations, the systems and methods discussed herein allow for identification of wild-type amino acids located in favorable environments on the input protein. Such implementations may narrow the sequence space of residues with very low wild-type probabilities. The improvements provided by implementations of the systems and methods discussed herein over the state of the art can be described as several discrete improvements which, when combined, form a significantly improved model for identifying candidate protein residues for overall improved utility.

FIG. 1A is a diagram of an implementation of a computer-implemented neural network for increasing synthesized protein characteristics. Some characteristics of protein that an engineer may desire to alter are maturation kinetics, thermal stability, $K_m$, $K_{cat}$, dependence on cations or anions for proper folding, and pH tolerance. At 101, a protein may be translated into microenvironments for each residue in the protein and a three dimensional model of the protein and its microenvironment is generated. Some methods for generating three-dimensional models include fragment assembly, when an unknown protein model is built from a pool of candidate fragments taken from known protein structures; segment matching, when known protein segments are matched to the amino acid sequence; or comparative protein modeling based on satisfaction of spatial restraints, when a known protein model is selected ("the template"), the residues of the amino acid sequences are mapped to the residues in the template sequence ("aligning"), restraints on various distances, angles, and dihedral angles in the sequence are derived from the alignment with the template structure, and violations of restraints are minimalized, among other methods. When the three-dimensional model of the protein crystal structure is generated, a corresponding microenvironment associated with the structure is generated.

In some embodiments, the three dimensional model may merely illustrate or represent the protein without the microenvironment. The three-dimensional model may be mapped to a three-dimensional array in some implementations. In one example, the coordinates of the three dimensional model are stored in a three-dimensional array. In some embodiments, a three-dimensional image may be generated from the three-dimensional model and the three-dimensional image may be mapped into a three-dimensional array. The image data in the array may be referred to as a voxelized matrix. As a pixel may represent an addressable element of an image in two-dimensional space, a voxel represents an addressable element in three-dimensional space.

In some implementations, features of the image may be extracted via three-dimensional convolution and max pooling layers. Three-dimensional filters in the three-dimensional convolutional layers search for recurrent spatial patterns that best capture the local biochemical features to separate the 20 amino acid microenvironments. Max Pooling layers perform down-sampling to the input to increase translational invariances of the network. The convolutional neural network architecture is discussed further below.

A first convolution layer 121 detects low level features via a filter. Convolutional neural networks use convolution to highlight features in a data set. In a convolution layer of a convolutional neural network, a filter is applied to the three-dimensional array to generate a feature map. In the convolutional layer, the filter slides over the inputs and the element by element dot product of the filter and the input is stored as a feature map. In some embodiments, a 3×3×3 filter may be applied to the three-dimensional image.

The feature map from the convolved filter and image is shown by 102. In some embodiments, a frame of reference may be created around a central amino acid in the image and features may be extracted around that central amino acid. The feature map created from the convolution of the image and the filter summarizes the presence of the filter-specific feature in the image. Increasing the number of filters applied to the image increases the number of features that can be tracked. In 102, 100 filters were applied to create an 18×18×18 feature map. In other implementations, other numbers of filters may be employed. The resulting feature maps may subsequently be passed through an activation function to account for nonlinear patterns in the features.

In some implementations, a rectifier linear function, having the formula $f(x)=\max(0,x)$ may be applied to the feature maps as the activation function. The rectifier linear activation function behaves linearly for positive values, making this function easy to optimize and subsequently allows the neural network to achieve high prediction accuracy. The rectifier linear activation function also outputs zero for any negative input, meaning it is not a true linear function. Thus, the output of a convolution layer in a convolutional neural network is a feature map, where the values in the feature map may be passed through a rectifier linear activation function.

A second convolutional layer is illustrated at 122. Increasing the number of convolutional layers may increase the complexity of the features that may be tracked. The convolutional layer at 122 incorporates another 100 filters to track features. In some embodiments, the filters are the same as in the first convolutional layer to ensure the accuracy of the tracked feature. In alternate embodiments, different filters may be incorporated in the second convolutional layer. In some embodiments, atoms associated with the central amino acid may be removed via filters.

In some implementations, a smaller data set of dimension 16×16×16 is indicated by 103 (although in other implementations, other dimensions may be utilized, or a greater or fewer number of filters applied). The dot product in the convolution at the second convolutional layer reduces the size of the data set. Data set 103 comprises a feature map that has tracked complex features from the original protein image 101.

In some implementations, a first pooling layer with dimensions 2×2×2 may be implemented at 123. A pooling layer may be implemented to down-sample the data. A pooling window may be applied to the feature map. In some embodiments, the pooling layer outputs the maximum value of the data in the window, down-sampling the data in the window. Max pooling highlights the most prominent feature in the pooling window. In other embodiments, the pooling layer outputs the average value of the data in the window.

The down-sampled data at 104 represents 200 independent 8×8×8 arrays. Down-sampling data allows the neural network to retain relevant information. While having an abundance of data may be advantageous because it allows the network to fine tune the accuracy of its weights, as discussed further below, large amounts of data may cause the neural network to spend significant time processing. Down-sampling data may be important in neural networks to reduce the computations necessary in the network. Although shown with pooling layer 123 with dimensions 2×2×2 and down-sampled data with dimensions 8×8×8, in other implementations, other sizes of pooling windows and down-sampled data may be utilized.

In some implementations, a subsequent convolutional layer 124 uses 200 independent 2×2×2 filters to then re-process the down-sampled data and highlight features in a new feature map. A smaller filter, 2×2×2 as opposed to 3×3×3 is implemented in the convolutional layer at 124 to account for the down-sampled data. The depth of the convolutional filters should be the same as the depth of the data to successfully perform dot product matrix multiplication. In other implementations, other sizes or dimensions of filters may be utilized, as discussed above.

The feature map from the convolved layer 124 and image is shown in 105. The feature map created from the convolution of the down-sampled data and the filter summarizes the presence of the filter-specific feature in the image. In the implementation illustrated at 105, there are 200 independent 7×7×7 arrays. The dot product from the convolution further reduces the size of the data.

Convolution layer 125 may extract more complex features using additional filters, such as by using 400 independent 2×2×2 filters from the lower resolution data set 105 as illustrated. Increasing the number of filters applied to the image increases the number of features that can be tracked. As this data has been down-sampled from pooling layer 123 and reduced in size substantially, more filters may be applied in this convolution layer to extract and highlight the features of the image of protein 101 without requiring overwhelming processing or memory requirements.

The feature map from the convolved layer 125 is shown in 106. The feature map created from the convolution of the down-sampled data and the filter summarizes the presence of the filter-specific feature in the image. In the implementation illustrated at 106, there are 400 independent 6×6×6 arrays, although other numbers or sizes of arrays may be utilized in various implementations. The dot product from the convolution further reduces the size of the data.

In some implementations, a second pooling layer with dimension 2×2×2 (or any other appropriate dimension size) is implemented at 126 to down-sample the data further. In some embodiments, the same type of pooling layer may be implemented in the second pooling layer as was implemented in the first pooling layer. The type of pooling layer determines the pooling window that is used to down-sample the data. For example, a max pooling layer can be implemented at 123 and 126. In other embodiments, different pooling layers may be implemented in the convolutional neural network. For example, a max pooling layer may be implemented at 123 while an average pooling layer may be implemented at 126. Max pooling layers highlight the most prominent feature in the pooling window, while average pooling layers output the average value of the data in the window.

In the illustrated implementation, the down-sampled data at 107 represents 400 independent 3×3×3 arrays, although other numbers or dimensions of arrays may be utilized. While having lots of data may be advantageous because it allows the network to fine tune the accuracy of its weights, as discussed further below, large amounts of data may cause the neural network to spend significant time processing. Down-sampling data may be useful in neural networks to reduce the computations necessary in the network.

Upon reducing the size of the data, the data may be further flattened in some implementations, meaning the data may be arranged into a one-dimensional vector. The data is flattened for purposes of matrix multiplication that occurs in the fully connected layers. The fully connected layer 127 may accordingly receive a flattened one-dimensional vector of length 10800 (e.g., from the 400×3×3×3 arrays of step 107, though the vector may have different lengths in other implementations). In the convolutional neural network fully connected layers, each number in the one-dimensional vector is applied to a neuron. The neuron sums the inputs and applies the activation function. In some embodiments, the activation function is the rectifier linear function. In alternate embodiments, the activation function may be the hyperbolic tangent or sigmoid function.

In the implementation illustrated, the first fully connected layer 127 outputs a one-dimensional vector at 108 of length 10800 (although other lengths may be utilized, as discussed above). The vector output by the fully connected layer represents a vector of real numbers. In some embodiments, the real numbers may be output and classified. In other embodiments, the real numbers may further be input into subsequent fully connected layers to improve the accuracy of the convolutional neural network.

In the present embodiment, the output of the first fully connected layer 108 is input into a second fully connected layer, indicated by 128. The output of the first fully connected layer 108 is already a one-dimensional vector so it does not need to be flattened before it is input into subsequent fully connected layers. In some embodiments, additional fully connected layers are implemented to improve the accuracy of the neural network. The number of additional fully connected layers may be limited by the processing power of the computer running the neural network. Alternatively, the addition of fully connected layers may be limited by insignificant increases in the accuracy compared to increases in the computation time to process the additional fully connected layers.

In the illustrated implementation, the second fully connected layer 128 outputs a one-dimensional vector of length 1000 at 109 (though other lengths may be utilized). The vector output by the fully connected layer represents a vector of real numbers. In some embodiments, the real numbers may be output and classified. In other embodiments, the real numbers may further be input into subsequent fully connected layers to improve the accuracy of the convolutional neural network.

At 129, in some implementations, the output of the fully connected layer 109 is input into a softmax classifier. The softmax classifier uses a softmax function, or a normalized exponential function, to transform an input of real numbers into a normalized probability distribution over predicted output classes. In alternate embodiments, a sigmoid function may be used to classify the output of the convolutional neural network. Sigmoid functions may be used if there is one class. A softmax function is a multi-class sigmoid function.

At 110, the output of the softmax layer is the probability of each of the 20 identified amino acids to improve a characteristic of the target protein (although a greater or lesser number of amino acids may be utilized in other implementations). This output may be input into additional convolutional neural networks such that the additional convolutional neural networks can perform different queries given the predicted amino acid sequence, or the output 110 may be used directly as the predicted amino acids that improve a characteristic of the target protein.

Figure 1B:
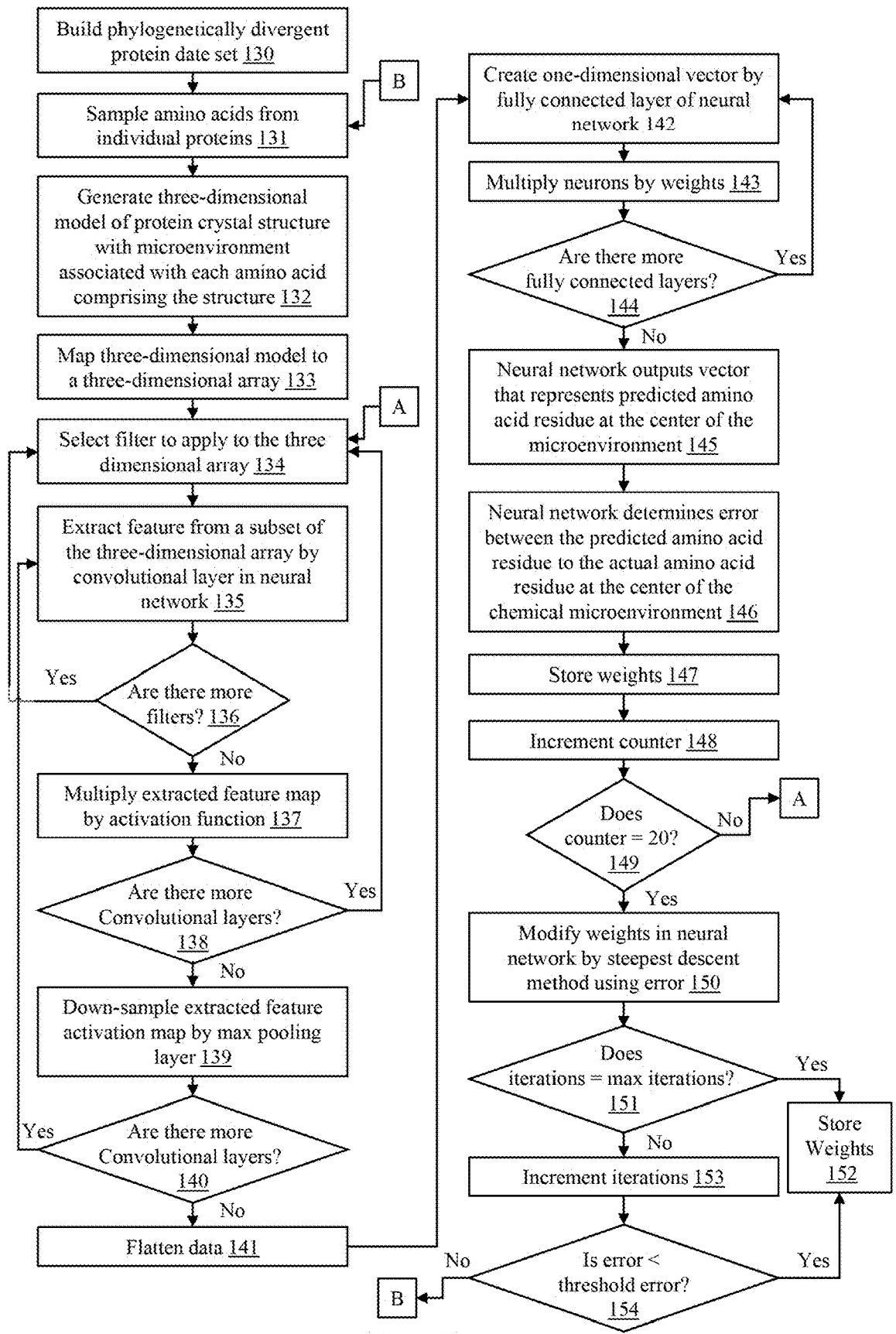
FIG. 1B is a flow chart of an implementation of a method for determining an amino acid residue at the center of a microenvironment.

FIG. 1B is a flow chart of an implementation of a method for determining an amino acid residue at the center of a microenvironment. A neural network may be trained on known input/output pairs such that the neural network can learn how to classify an output given a certain input. Once the neural network has learned how to classify known input/output pairs, the neural network can operate on unknown inputs to predict what the classified output should be. In the present embodiment, the neural network is trained to predict an amino acid at the center of a microenvironment. During testing, the neural network may be provided with an amino acid sequence, analyze the microenvironments surrounding the amino acids, and predict an amino acid residue that differs from the natural amino acid residue. The neural network's predicted amino acid indicates that an improved protein may be generated by mutating the natural amino acid residue to the predicted amino acid residue.

At step 130, in some implementations, a diverse protein sample set may be compiled or built that will be used to train the neural network. The more diverse the sample set is, the more robust the neural network can be in its classifications. For example, a neural network will attempt to classify input/output pairs during a first iteration of learning. If, during a next iteration of learning, the input/output pairs are similar to the learned input/output pair of the first iteration, the neural network may artificially perform higher than it should perform merely because the data is similar, and not because the neural network is robust. If a diverse input/output pair is subsequently input to the network for the third iteration, the classification error will likely be much higher than it would be if the first two input/output pairs were diverse. The similarity of the first two input/output pairs might cause the neural network to fine tuning itself to learning the similar input/output pairs of the first two iterations. This may be called "overtraining" the network.

Alternatively, if the second iteration of training used a distinct input/output pair compared to the input/output pair of the first iteration, the neural network will be forced to be able to classify a broader range of input/output pairs. During testing, the outputs are not known so it is ideal for the network to be able to classify a broad range of input/output pairs.

Accordingly, in some implementations of step 130, a training data set for a neural network is built from proteins that are all phylogenetically divergent over a certain threshold. In various embodiments, the data set is built from proteins that are at least 20%, 30%, 40%, or 50% phylogenetically divergent. Such filtering increases efficiency by removing very similar/duplicate proteins that may occur many times in the training set. Such an improvement may reduce a bias present in the current state of the art towards oversampled proteins.

In some embodiments, the individual proteins in the training dataset were modified by adding hydrogen atoms to those Protein DataBase (PDB) structures that lacked annotations. In one embodiment, the addition of hydrogen atoms is accomplished using a software converter, for example pdb2pgr. In another embodiment, atoms are further segregated by the bonding capabilities of each atom and the inclusion of other atoms like phosphorus in DNA backbones.

In some embodiments, the individual proteins in the training set were modified by adding biophysical channels to the protein model, taking into account additional characteristics of the protein, including but not limited to partial charge, beta factors, secondary structure, aromaticity, and polarity.

In some embodiments, training data may be removed where high- and low-resolution models for the same protein may coexist in a protein database. According to some implementations of the methods discussed herein, all genes with an associated structure with a resolution below a threshold may be grouped together in groups having a sequence similarity above a certain percentage threshold. As used herein, "resolution" refers to the resolvability of an electron density map of a molecule, typically measured in angstroms (Å). A molecular model with "lower" resolution is of higher quality than a molecular model with "higher" resolution, because the electron density map is resolvable to a lower distance between points, meaning that more features of the molecular structure are visible. In one example, all genes with an associated structure and a resolution below 2.5 Å and a sequence similarity of at least 50% are grouped together, and the available structure with the lowest resolution is selected for use in a training model, with higher-resolution (lower quality) molecular models removed.

Figure 2A:
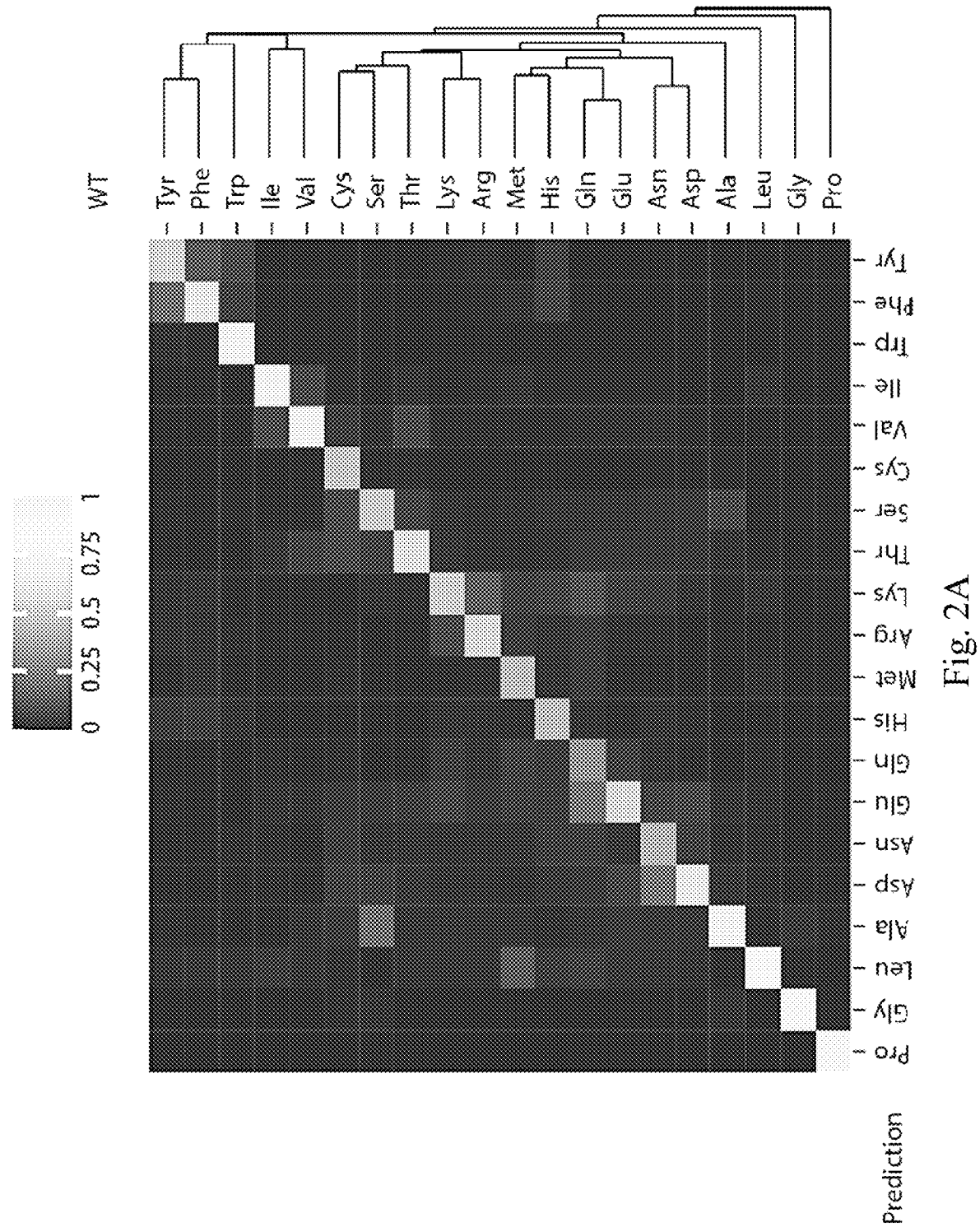
FIG. 2A is a graph of experimental results of an implementation of a method and system for increasing synthesized protein characteristics.

In some embodiments, amino acid sampling was normalized relative to cysteine in its abundance in the PDB as opposed to equal representation of all 20 amino acids. In one embodiment, amino acid sampling may be normalized relative to natural occurrence. In one embodiment, amino acid sampling may be normalized relative to natural occurrence within a given species. Cysteine amino acids were modified in the data sample because cysteine can artificially be assigned a high probability at any given location. Cysteine is the rarest amino acid observed in the PDB, thus, it is possible that the more abundant amino acids were undersampled, and the diversity of protein microenvironments that might occupy was being incompletely represented. Modifying the cysteine amino acids in the data sample led to a significant increase in wild-type accuracy. On a per amino acid basis, the accuracy ranges from 96.7% to 32.8% (see FIG. 2A).

In step 131, amino acids in a protein may be sampled randomly from the amino acid sequence. In one embodiment, up to 50% of the amino acids in a protein were sampled unless the protein was large, in which case no more than 100 amino acids were sampled from an individual protein. In another embodiment, the upper limit was 200 amino acids per individual protein. The disclosed sampling method removes a bias in the data set towards residues at the outside of a protein.

In step 132, a three-dimensional model of protein crystal structures, along with microenvironments associated with each amino acid comprising the structure, may be created. For example, some methods for generating the three-dimensional models include fragment assembly, when an unknown protein model is built from a pool of candidate fragments taken from known protein structures; segment matching, when known protein segments are matched to the amino acid sequence; or comparative protein modeling based on satisfaction of spatial restraints, when a known protein model is selected ("the template"), the residues of the amino acid sequences are mapped to the residues in the template sequence ("aligning"), restraints on various distances, angels, and dihedral angels in the sequence are derived from the alignment with the template structure, and violations of restraints are minimized, among other methods. When the three-dimensional model of the protein crystal structure is generated, microenvironments associated with each amino acid comprising the structure is also generated. One difficulty with existing protein structure databases is that as new proteins get added, different methods are used to create the crystallographic structures. Different methods of creating three-dimensional structures may add different biases or artifacts that can affect the accuracy of the models. Rebuilding structures using the latest, same version of the same method ensures that the training structures vary in chemical composition rather than in artifacts or errors presents in older versions.

In step 133, the generated three-dimensional model from step 132 may be mapped into a three dimensional array. In one example, the coordinates of the three dimensional model are stored in a three-dimensional array. In some embodiments, a three-dimensional image may be generated from the three-dimensional model and the three-dimensional image may be mapped into a three-dimensional array. The image data in the array may be called a voxelized matrix. As a pixel represents an addressable element of an image in two-dimensional space, a voxel represents an addressable element in three-dimensional space.

In step 134, the image is input into a convolution layer in the convolutional neural network. Convolutional layers detect features in images via filters. Filters are designed to detect the presence of certain features in an image. In a simplified example, high-pass filters detect the presence of high frequency signals. The output of the high-pass filter are the parts of the signal that have high frequency. Similarly, image filters can be designed to track certain features in an image. The more filters that are applied to the image, the more features that can be tracked.

In step 135, the image is convolved with the filter in the convolutional layer to extract a filter-specific feature in an image. In the convolutional layer, the filter slides over the inputs and the element by element dot product of the filter and the input is stored as a feature map.

The decision in 136 depends on whether or not there are more filters. As discussed above, more filters implemented may mean more features that can be tracked in the image. Each filter is convolved with the image independently to create an independent feature map. If more filters are to be convolved with the image, steps 134 and 135 may be repeated. If all of the filters have been convolved with the image, then the process proceeds to step 137. In some embodiments, the feature maps may be concatenated together to create a feature map that is as deep as the number of filters applied to the image. In other embodiments, the feature maps may be processed one at a time.

In step 137, an activation function is applied to the feature maps in the convolutional layer of the convolutional neural network. The activation function allows the neural network to detect nonlinear patterns in the extracted feature maps. A rectifier linear function, having the formula $f(x)=\max(0,x)$ may be applied to the feature maps. The rectifier linear activation function behaves linearly for positive values, making this function easy to optimize and subsequently allow the neural network to achieve higher accuracy. The rectifier linear activation function also outputs zero for any negative input, meaning it is not a true linear function. Thus, the output of a convolution layer in a convolutional neural network is a feature map, where the values in the feature map have been passed through a rectifier linear activation function.

The decision in 138 depends on whether or not there are more convolutional layers. Increasing the number of convolutional layers may increase the complexity of the features that may be tracked. If there are additional convolutional layers, a new filter may be applied to the image and the process may repeat steps 134-138. In some embodiments, the filters may be the same as in the first convolutional layer to ensure the accuracy of the tracked feature. In alternate embodiments, different filters may be incorporated in the second convolutional layer. If there are not more convolutional layers, then the process proceeds to step 139.

In step 139, a pooling layer down-samples the data. A pooling window may be applied to the feature map. In some embodiments, the pooling layer outputs the maximum value of the data in the window, down-sampling the data in the window. Max pooling highlights the most prominent feature in the pooling window. In other embodiments, the pooling layer outputs the average value of the data in the window.

The decision in 140 depends on whether or not there are more convolutional layers. Increasing the number of convolutional layers may increase the complexity of the features that may be tracked. If there are additional convolutional layers, a new filter may be applied to the image and the process may repeat steps 134-140. In some embodiments, the filters are the same as in the first convolutional layer to ensure the accuracy of the tracked feature. In alternate embodiments, different filters may be incorporated in the second convolutional layer. Accordingly, the repeated iterations of steps 134-136, 134-138, and 134-140 provide flexibility and increased complexity of tracked features. If there are not more convolutional layers, then the process proceeds to step 141.

In step 141, in some implementations, the down-sampled data is flattened. This means that the data is arranged into a one-dimensional vector. The data is flattened for purposes of matrix multiplication that occurs in the fully connected layers.

In step 142, in some implementations, the flattened one-dimensional vector is input into a fully connected layer of the neural network. In the convolutional neural network fully connected layers, each number in the one-dimensional vector is applied to a neuron as an input. The neuron sums the inputs and applies the activation function. In some embodiments, the activation function is the rectifier linear function. In alternate embodiments, the activation function may be the hyperbolic tangent or sigmoid function.

In some embodiments, the output of the first set of neurons in the fully connected layer may be input to another set of neurons via weights. Each subsequent set of neurons may be referred to as a "hidden layer" of neurons. The number of hidden layers in the fully connected may be pruned. In other words, the number of hidden layers in the neural network may adaptively change as the neuron network learns how to classify the outputs.

In step 143, in some implementations, the neurons that comprise the fully connected network are connected to other neurons by weights. The weights are adjusted to strengthen the effect of some neurons and weaken the effect of other neurons. The adjustment of each neuron's strength allows the neural network to better classify outputs. The weights connecting the neurons are adjusted while the neural network is learning how to classify the input, or "training." In some embodiments, the number of neurons in the neural network may be pruned. In other words, the number of neurons that are active in the neural network adaptively changes as the neural network learns how to classify the output.

The decision in 144 depends on whether or not there are additional fully connected layers. In some embodiments, the output of one fully connected layer may become the input to a second fully connected layer. In some embodiments, additional fully connected layers are implemented to improve the accuracy of the neural network. The number of additional fully connected layers may be limited by the processing power of the computer running the neural network. Alternatively, the addition of fully connected layers may be limited by insignificant increases in accuracy compared to increase in computational time to process the additional fully connected layers. In alternate embodiments, the output of one fully connected layer may be sufficient to classify the image. If there are additional fully connected layers, steps 142 and 143 are repeated such that the input vector is supplied to neurons which are connected to each other via weights. If there are not additional fully connected layers, the process proceeds to step 145.

At step 145, in some implementations, the fully connected layer outputs a vector of real numbers. In some embodiments, the real numbers may be output and classified. In alternate embodiments, the output of the fully connected layer is input into a softmax classifier. The softmax classifier uses a softmax function, or a normalized exponential function, to transform an input of real numbers into a normalized probability distribution over predicted output classes. In other embodiments, a sigmoid function may be used to classify the output of the convolutional neural network. Sigmoid functions may be used if there is one class. A softmax function is a multi-class sigmoid function. In some embodiments, the output of the neural network represents a predicted amino acid residue at the center of the chemical microenvironment.

For example, the neural network may output a vector with a length of 20, comprising 20 real numbers. The vector has a length of 20 because of the 20 possible amino acids that may exist at the center of the microenvironment. The real numbers in the vector are passed through a softmax classifier, such that the values in the vector represent the likelihood of the amino acids existing at the center of the microenvironment.

In step 146, in some implementations, the predicted amino acid residue is compared to the natural amino acid at the center of the chemical environment. For example, the true amino acid vector may be a vector of length 20, where a single '1' indicates the natural amino acid at the center of the chemical environment and the other values in the vector hold '0'.

This type of learning in a neural network, learning that compares known input/output pairs during training, is called supervised learning. The differences between the predicted values and known values may be determined, and the information is back-propagated through the neural network. The weights may be subsequently modified by the error signal. This method of training the neural network is called the back-propagation method.

In step 147, in some implementations, the weights are updated via the steepest descent method. Equation 1 below illustrates how the weights are adjusted at each iteration n.

$$w_{ji}(n+1) = w_{ji}(n) + \Delta w_{ji} \quad (1)$$

In Equation 1 above, $w_{ji}$ represents the weight that connects neuron i to neuron j.

The steepest descent method is an optimization technique that minimizes an objective function. In other words, the steepest descent method is able to adjust unknown parameters in the direction of steepest descent. During training, the value of the weights that optimizes the neural network's classification accuracy is unknown. Thus, the weights are the unknown parameters that are adjusted in the direction of steepest descent.

In some embodiments, the objective function may be the cross-entropy error function. Minimizing the cross-entropy error function represents minimizing the differences between the probability distribution of the predicted amino acid vector and the probability distribution of the natural amino acid vector. In other embodiments, the objective function may be the square error function. Minimizing the square error objective function represents minimizing the instantaneous error of each neuron.

During each training iteration, the weights are adjusted to get closer to their optimal value. Depending on the location of the neuron in the network, a different formula is used to determine how the weights are adjusted with respect to the objective function. Equation 2 below illustrates how the weight between neuron i and neuron j is adjusted with respect to the cross-entropy error function.

$$\Delta w_{ji} = -\frac{\partial \varepsilon(n)}{\partial w_{ji}(n)} \quad (2)$$

If the weights are too small, meaning the output of the neuron may not be having a significant effect on the classification, there will be a positive change in the weight because of the negative slope of the weight when a small weight is compared to the optimal weight, and the negative sign in the equation. If the weights are too large, there will be a negative change in the weight because of the positive slope of the weight when a large weight is compared to the optimal weight, and the negative sign in the equation. Thus, the weights train themselves to get closer to the optimal value. The modification of the weights may be temporarily stored, indicated by step 147.

In some embodiments, every time the modification of the weights is determined, the weights may be adjusted. This type of training may be called on-line or incremental training. One advantage to incremental training includes the neural network's ability to track small changes in the inputs. In some embodiments, the weights may be modified after the neural network has received a batch of input/output pairs. This type of training may be called batch training. One advantage to batch training includes the neural network's faster convergence to optimized weight values. In the present embodiments, a neural network was trained on 1.6 million amino acid and microenvironment pairings. In the present embodiment, batch sizes of 20 were used. In step 148, a counter is incremented. The neural network completes one round of batch training when the counter reaches 20. In other words, when the neural network evaluates itself based on 20 input/output pairs, one round of training is completed.

The decision in 149 depends on whether the present batch of training samples has been completed. If the number of training samples required to satisfy one batch is attained, the network continues to step 150. As discussed above, 20 input/output pairs are required for one batch of training. If the number of samples required to satisfying one batch has not been attained, the neural network repeats steps 134-149.

In step 150, the weight modifications that were temporarily stored in step 147 are summed. The values of the weights are modified according to the summed modifications such that a new batch of 20 input/output pairs will be evaluated using the newly modified weight values.

The decision in 151 depends on whether the maximum number of training iterations has been reached. One training iteration is completed when one round of batch training is completed. In some circumstances, the weights may never reach their optimal value because the weights will keep oscillating around their optimal value. Thus, in some embodiments a maximum number of iterations can be set to prevent the neural network from training the network indefinitely.

If the maximum number of iterations has not been reached, the neural network may be permitted to train the network again using another input/output pair from the data sample created in step 130. The iteration counter is increased at step 153, after the neural network has completed one batch of training.

If the maximum number of iterations has been reached, the neural network may store the value of the weights. Step 152 illustrates storing the value of the weights. These weights will be stored in memory because they are the weights that have been trained by the network and will subsequently be used when testing the neural network.

If the number of iterations has not been reached, the error between the predicted amino acid residue and the known natural amino acid residue may be evaluated. This evaluation is performed at step 154. In some circumstances, the error between the predicted values and the known natural values is so small that the error may be deemed acceptable and the neural network does not need to continue training. In these circumstances the value of the weights that yielded such small error rates may be stored and subsequently used in testing. In some embodiments, the neural network must maintain a small error rate for several iterations to ensure that the neural network did not learn how to predict one output very well or accidentally predict one output very well. Requiring the network to maintain a small error over several iterations increases the likelihood that the network is properly classifying a diverse range of inputs. If the error between the predicted and known values is still too large, the neural network may continue training itself and repeat steps 131-154. In many implementations, during repeat iterations of steps 131-154, the neural network will use a new data set to train the neural network.

Figure 1C:
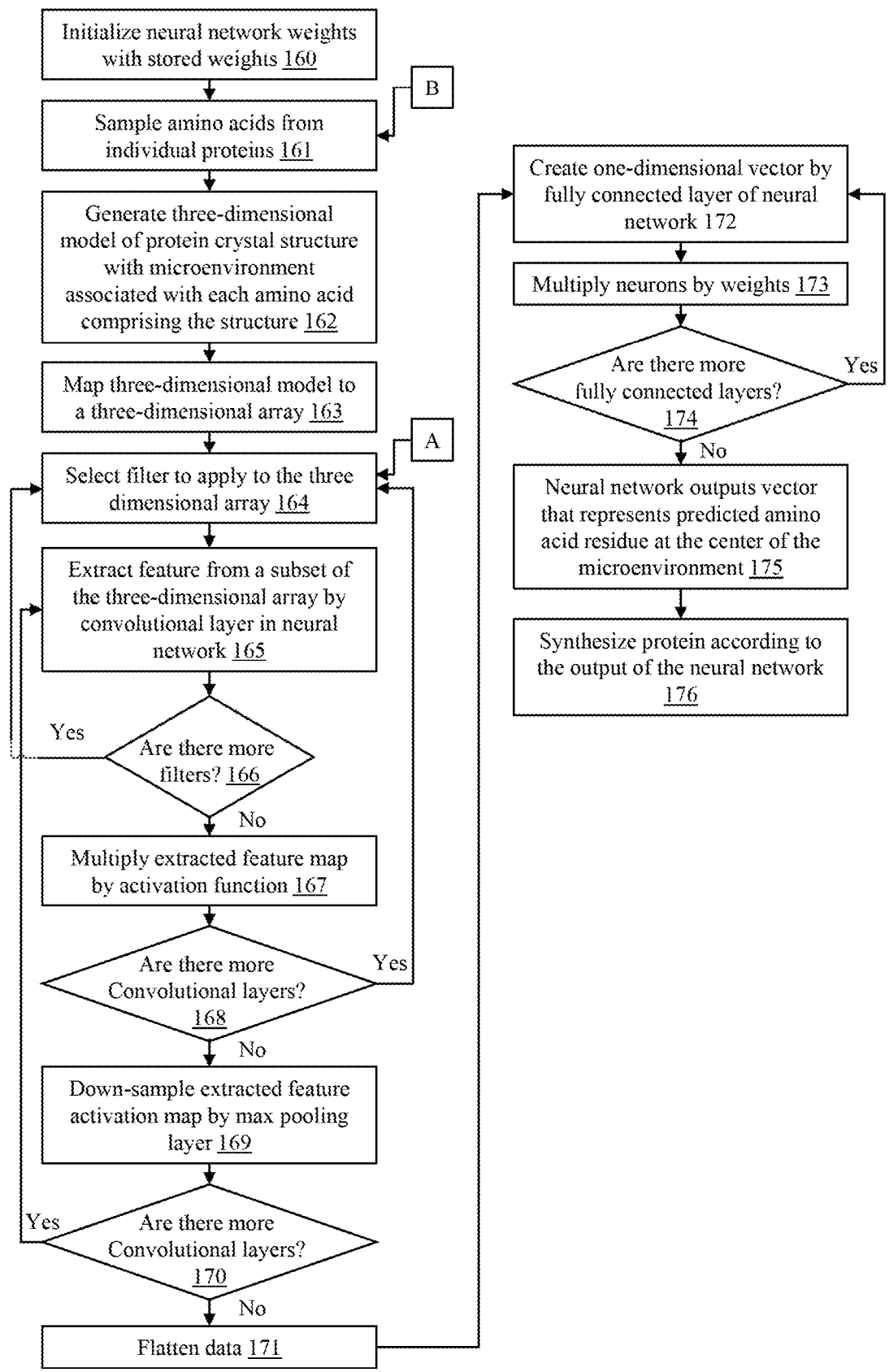
FIG. 1C is a flow chart of an implementation of a method for increasing synthesized protein characteristics during testing.

FIG. 1C is a flow chart of an implementation of a method for increasing synthesized protein characteristics during testing. In step 160, the weights that were stored from the training scenario are set as the weights in the fully connected layer in step 172. These weights are used when an unknown input needs to be classified because the weights have been trained via a broad and diverse set of inputs such that the weights should likely be able to classify the unknown input accurately.

In step 161, in some implementations, an unknown protein is sampled randomly. In one embodiment, up to 50% of the amino acids in a protein are sampled unless the protein is large, in which case no more than 100 amino acids were sampled from an individual protein. In another embodiment, the upper limit is 200 amino acids per individual protein. The disclosed sampling method removes a bias in the data set towards residues at the outside of a protein.

In step 162, a three-dimensional model of protein crystal structures, along with microenvironments associated with each amino acid comprising the structure, may be created. Some methods for generating the three-dimensional models include fragment assembly, when an unknown protein model is built from a pool of candidate fragments taken from known protein structures; segment matching, when known protein segments are matched to the amino acid sequence; or comparative protein modeling based on satisfaction of spatial restraints, when a known protein model is selected ("the template"), the residues of the amino acid sequences are mapped to the residues in the template sequence ("aligning"), restraints on various distances, angels, and dihedral angels in the sequence are derived from the alignment with the template structure, and violations of restraints are minimalized, among other methods. When the three-dimensional model of the protein crystal structure is generated, a microenvironment associated with each amino acid comprising the structure is also generated. One difficulty with existing protein structure databases is that as new proteins get added, different methods are used to create the crystallographic structures. Different methods of creating three-dimensional structures may add different biases or artifacts that can affect the accuracy of the models. Rebuilding structures using the latest, same version of the same method ensures that the training structures vary in chemical composition rather than in artifacts or errors presents in older versions.

In step 163, the generated three-dimensional model from step 162 may be mapped into a three-dimensional array. In one example, the coordinates of the three-dimensional model are stored in a three-dimensional array. In some embodiments, a three-dimensional image may be generated from the three-dimensional model and the three-dimensional image may be mapped into a three-dimensional array. The image data in the array may be called a voxelized matrix. As a pixel represents an addressable element of an image in two-dimensional space, a voxel represents an addressable element in three-dimensional space.

In step 164, the image may be input into a convolution layer in the convolutional neural network. Convolution layers detect features in images via filters. Filters are designed to detect the presence of certain features in an image. In a simplified example, high-pass filters detect the presence of high frequency signals. The output of the high-pass filter are the parts of the signal that have high frequency. Similarly, image filters can be designed to track certain features in an image. The more filters that are applied to the image, the more features that may be tracked.

In step 165, the image is convolved with the filter in the convolutional layer to extract a filter-specific feature in an image. In the convolutional layer, the filter slides over the inputs and the element by element dot product of the filter and the input is stored as a feature map.

The decision in 166 depends on whether or not there are more filters. As discussed above, the more filters implemented means the more features that may be tracked in the image. Each filter is convolved with the image independently to create an independent feature map. If more filters are to be convolved with the image, steps 164 and 165 may be repeat. If all of the filters have been convolved with the image, then the process proceeds to step 167. In some embodiments, the feature maps may be concatenated together to create a feature map that is as deep as the number of filters applied to the image. In other embodiments, the feature maps may be processed one at a time.

In step 167, in some implementations, an activation function is applied to the feature maps in the convolutional layer of the convolutional neural network. The activation function allows the neural network to detect nonlinear patterns in the extracted feature maps. A rectifier linear function, having the formula $f(x)=\max(0,x)$ may be applied to the feature maps as the activation function. The rectifier linear activation function behaves linearly for positive values, making this function easy to optimize and subsequently allows the neural network to achieve high prediction accuracy. The rectifier linear activation function also outputs zero for any negative input, meaning it is not a true linear function. Thus, the output of a convolution layer in a convolutional neural network is a feature map, where the values in the feature map may be passed through a rectifier linear activation function.

The decision in 168 depends on whether or not there are more convolutional layers. Increasing the number of convolutional layers may increase the complexity of the features that may be tracked. If there are additional convolutional layers, a new filter is applied to the image and steps 164-168 may be repeated. In some embodiments, the filters are the same as in the first convolutional layer to ensure the accuracy of the tracked feature. In alternate embodiments, different filters may be incorporated in the second convolutional layer. If there are not more convolutional layers, then the process proceeds to step 169.

In step 169, a pooling layer down-samples the data. A pooling window may be applied to the feature map. In some embodiments, the pooling layer outputs the maximum value of the data in the window, down-sampling the data in the window. Max pooling highlights the most prominent feature in the pooling window. In other embodiments, the pooling layer outputs the average value of the data in the window.

The decision in 170 depends on whether or not there are more convolutional layers. Increasing the number of convolutional layers may increase the complexity of the features that may be tracked. If there are additional convolutional layers, a new filter is applied to the image and steps 164-170 may be repeated. In some embodiments, the filters are the same as in the first convolutional layer to ensure the accuracy of the tracked feature. In alternate embodiments, different filters may be incorporated in the second convolutional layer. If there are not more convolutional layers, then the process proceeds to step 171.

In step 171, in some implementations, the down-sampled data is flattened. This means that the data is arranged into a one-dimensional vector. The data is flattened for purposes of matrix multiplication that occurs in the fully connected layers.

In step 172, in some implementations, the flattened one-dimensional vector is input into a fully connected layer of the neural network. In the convolutional neural network fully connected layers, each number in the one-dimensional vector is applied to a neuron. The neuron sums the inputs and applies the activation function. In some embodiments, the activation function is the rectifier linear function. In alternate embodiments, the activation function may be the hyperbolic tangent or sigmoid function.

In step 173, in some implementations, the neurons that comprise the fully connected network are multiplied by weights. The weights in the fully connected network are the weights that were initialized in step 160. These weights are used when an unknown input is evaluated because the weights have been trained via a broad and diverse set of inputs such that the weights should likely be able to classify the unknown input accurately.

The decision in 174 depends on whether or not there are additional fully connected layers. In some embodiments, the output of one fully connected layer may become the input to a second fully connected layer. In some embodiments, additional fully connected layers are implemented to improve the accuracy of the neural network. The number of additional fully connected layers may be limited by the processing power of the computer running the neural network. Alternatively, the addition of fully connected layers may be limited by insignificant increases in accuracy compared to increases in the computational time to process the additional fully connected layers. In alternate embodiments, the output of one fully connected layer may be sufficient to classify the image. If there are additional fully connected layers, steps 172 and 173 are repeated such that the input vector is supplied to neurons which are connected to each other via weights. If there are not additional fully connected layers, the process proceeds to step 175.

At step 175, the fully connected layer outputs a vector of real numbers. In some embodiments, the real numbers may be output and classified. In alternate embodiments, the output of the fully connected layer is input into a softmax classifier. The softmax classifier uses a softmax function, or a normalized exponential function, to transform an input of real numbers into a normalized probability distribution over predicted output classes. In other embodiments, a sigmoid function may be used to classify the output of the convolutional neural network. Sigmoid functions may be used if there is one class. A softmax function is a multi-class sigmoid function. In some embodiments, the output of the neural network represents a predicted candidate residue and amino acid residue to improve a quality metric of a protein.

In step 176, a synthesized protein may be generated according to the output of the neural network. The synthesized protein may be generated by the computing device executing the neural network, by another computing device in communication with the computing device executing the neural network, by a third party manufacturer or laboratory, or another entity making substitutions according to the candidate and predicted amino acid residues identified by the neural network. For example, in some embodiments, the synthesized protein may be obtained by an entity making one or more substitution according to the predicted amino acid residues and candidate residues identified by the neural network and/or at the direction of the neural network or computing device executing the neural network. In some embodiments, the neural network may predict an amino acid residue that is the same as the natural amino acid residue. In other embodiments, the neural network may predict an amino acid residue that is different from the natural amino acid residue. The neural network's predicted amino acid indicates than an improved protein may be generated by mutating the natural amino acid residue to the predicted amino acid residue. Thus, a synthesized protein may be generated according to the output of the neural network.

Figure 1D:
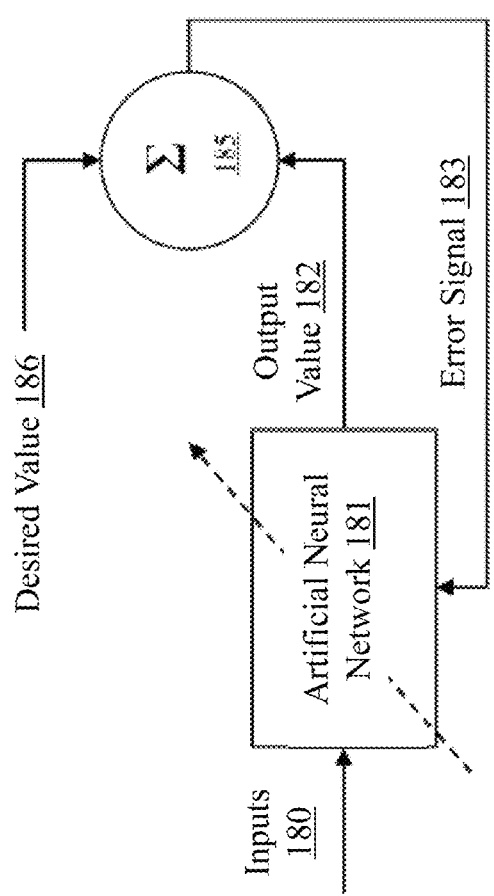
FIG. 1D is a block diagram of an implementation of a neural network for increasing synthesized protein characteristics during training.

FIG. 1D is a block diagram of a neural network during training, according to some implementations. Inputs are supplied to the neural network at 180. As discussed above, a neural network is capable of accepting various inputs. In some embodiments, the neural network accepts an amino acid sequence or residue. In other embodiments, the neural network may receive a series of amino acids have discrete attributes located at each position of the series.

In the block diagram, 181 represents the neural network changing over time. As discussed above, during training, the neural network adaptively updates each iteration of new inputs/outputs. The neural network adaptively updates because the weights are updated depending on the error signal calculated by the difference between the predicted output and the known output.

In the block diagram, 182 represents the outputs that the neural network predicts will satisfy a query. For example, a neural network may be queried and trained to identify a particular amino acid residue that may be modified. In these circumstances, the output of the neural network may be an amino acid residue, wherein the amino acid residue may be used to synthesize a new protein with improved characteristics. In other embodiments, the output of the neural network may be an amino acid residue that may be used as a substitute, wherein the substitute may be used to synthesize a new protein with improved characteristics. In other embodiments, the neural network may be queried for a proposed amino acid sequence for a protein of a different parameter than an initial amino acid sequence. In these circumstances, the output of the neural network may be an amino acid sequence indicating a specific amino acid for each residue of the amino acid sequence.

In the block diagram, 186 represents the desired value. This type of training is called supervised training because to train the neural network, the inputs that correspond to the outputs must be known. During training, the neural network is asked to output results that are as close to possible to the desired value.

The desired value 186 and the output value from the neural network 182 are compared at 185. The difference between the output value and the desired value is determined and becomes an error signal 183 that is propagated back through the neural network so the neural network can learn from this error. As illustrated in Equations 1 and 2 above, the weights are updated based on the error signal.

Figure 1E:
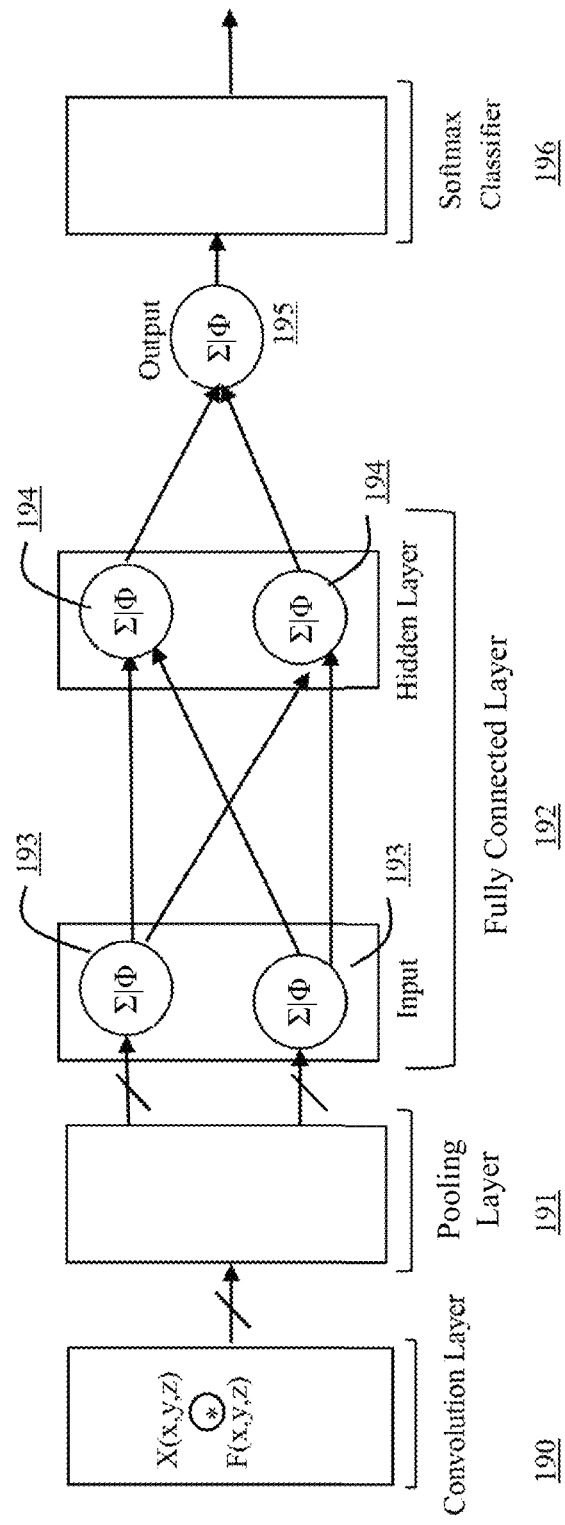
FIG. 1E is a block diagram of an implementation of a convolutional neural network for increasing synthesized protein characteristics.

FIG. 1E is a block diagram of a convolutional neural network, according to some implementations. In the block diagram, 190 represents a convolutional layer. Convolutional layers may detect features in images via filters. Filters are designed to detect the presence of certain features in an image. In a simplified example, high-pass filters detect the presence of high frequency signals. The output of the high-pass filter are the parts of the signal that have high frequency. Similarly, image filters can be designed to track certain features in an image. The more filters that are applied to the image, the more features that can be tracked.

In some implementations, an image is convolved with the filter in the convolutional layer to extract a filter-specific feature in an image. In the convolutional layer, the filter slides over the inputs and the element by element dot product of the filter and the input is stored as a feature map. An activation function is applied to the feature map in the convolutional layer of the convolutional neural network. The activation function allows the neural network to detect nonlinear patterns in the extracted feature maps. A rectifier linear function, having the formula $f(x)=\max(0,x)$ may be applied to the feature maps. The rectifier linear activation function behaves linearly for positive values, making this function easy to optimize and subsequently allow the neural network to achieve high prediction accuracy. The rectifier linear activation function also outputs zero for any negative input, meaning it is not a true linear function. Thus, the output of a convolution layer in a convolutional neural network is a feature map, where the values in the feature map have been passed through a rectifier linear activation function. In other embodiments, a sigmoid function or hyperbolic tangent function may be applied as activation functions.

The extracted feature maps that have been acted on by an activation function may subsequently be input into a pooling layer, as indicated by 191. The pooling layer down-samples the data. A pooling window may be applied to the feature map. In some embodiments, the pooling layer outputs the maximum value of the data in the window, down-sampling the data in the window. Max pooling highlights the most prominent feature in the pooling window.

The down-sampled pooling data may subsequently be flattened before being input into fully connected layers 192 of the convolutional neural network in some implementations.

In some embodiments, the fully connected layers may only have one set of neurons. In alternate embodiments, the fully connected layer may have a set of neurons in a first layer 193, and a set of neurons in subsequent hidden layers 194. The number of hidden layers in the fully connected may be pruned. In other words, the number of hidden layers in the neural network may adaptively chance as the neuron network learns how to classify the outputs.

In the fully connected layers, the neurons in each of the layers 193 and 194 are connected to each other. The neurons are connected by weights. During training, the weights are adjusted to strengthen the effect of some neurons and weaken the effect of other neurons. The adjustment of each neuron's strength allows the neural network to better classify outputs. In some embodiments, the number of neurons in the neural network may be pruned. In other words, the number of neurons that are active in the neural network adaptively changes as the neural network learns how to classify the output.

After training, the error between the predicted values and known values may be so small that the error may be deemed acceptable and the neural network does not need to continue training. In these circumstances the value of the weights that yielded such small error rates may be stored and subsequently used in testing. In some embodiments, the neural network must satisfy the small error rate for several iterations to ensure that the neural network did not learn how to predict one output very well or accidentally predict one output very well. Requiring the network to maintain a small error over several iterations increases the likelihood that the network is properly classifying a diverse range of inputs.

In the block diagram, 195 represents the output of the neural network. The output of the fully connected layer is a vector of real numbers. In some embodiments, the real numbers may be output and classified. In alternate embodiments, the output of the fully connected layer is input into a softmax classifier.

In the block diagram, 196 represents the softmax classifier layer. The softmax classifier uses a softmax function, or a normalized exponential function, to transform an input of real numbers into a normalized probability distribution over predicted output classes. In other embodiments, a sigmoid function may be used to classify the output of the convolutional neural network. Sigmoid functions may be used if there is one class. A softmax function is a multi-class sigmoid function. In some embodiments, the output of the neural network represents a predicted candidate residue and amino acid residue to improve a quality metric of a protein. In other embodiments, the output of the neural network may be an amino acid sequence indicating a specific amino acid for each residue of the amino acid sequence.

In some embodiments, problematic residues are identified, suggestions made for new residues, by combining predictions from multiple, independently trained neural networks. By identifying residues based on independently trained neural networks, biases due to idiosyncrasies that emerge while a neural network is training, and that are unique to any individual neural network, may be removed. The average of many independent neural networks eliminates quirks associated with any individual one.

Figure 2B:
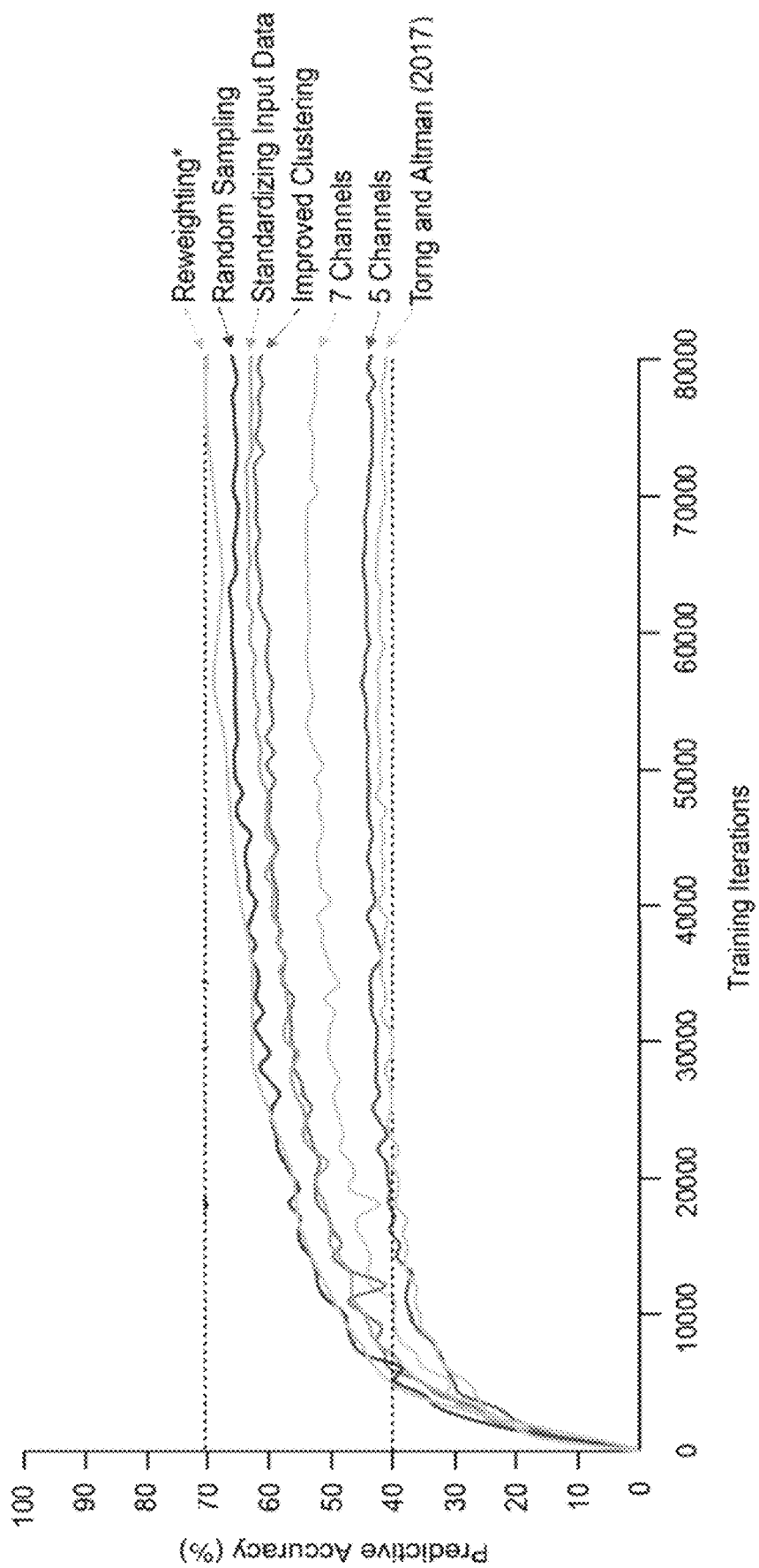
FIG. 2B is another graph of experimental results of an implementation of a method and system for increasing synthesized protein characteristics.

The various improvements to existing algorithms improved accuracy cumulatively. As shown in FIG. 2B, the various improvements, taken together, in one embodiment increased the model accuracy of the wild type amino acid prediction from about 40% to over 70% across all amino acids.

Engineered Proteins

Implementations of the systems and methods discussed herein further provide or identify compositions comprising engineered proteins comprising one or more mutations that modify a desired trait or property of the protein as compared to a trait or property of the native or parental protein. In one embodiment, the modified proteins generated or identified by implementations of the systems and methods discussed herein comprise one or more mutations at one or more amino acid residue predicted by the 3D convolutional neural network (3DCNN) predictive pipeline of implementations of the systems and methods discussed herein to confer a desired trait or property to the protein. The engineered proteins generated or identified by implementations of the systems and methods discussed herein which have been generated to include a mutation at a residue predicted from analysis by the 3DCNN predictive pipeline are referred to herein as 3DCNN-engineered proteins.

Exemplary traits or properties that can be modified in the 3DCNN-engineered proteins generated or identified by implementations of the systems and methods discussed herein, include, but are not limited to, stability, affinity, activity, half-life, a fluorescent property, and sensitivity to photobleaching.

The 3DCNN-engineered proteins generated or identified by implementations of the systems and methods discussed herein may be made using chemical methods. For example, 3DCNN-engineered proteins can be synthesized by solid phase techniques (Roberge J Y et al (1995) Science 269: 202-204), cleaved from the resin, and purified by preparative high performance liquid chromatography. Automated synthesis may be achieved, for example, using the ABI 431 A Peptide Synthesizer (Perkin Elmer) in accordance with the instructions provided by the manufacturer.

The 3DCNN-engineered proteins may alternatively be made by translation of an encoding nucleic acid sequence, by recombinant means or by cleavage from a longer protein sequence. The composition of a 3DCNN-engineered protein may be confirmed by amino acid analysis or sequencing.

The variants of the 3DCNN-engineered proteins generated or identified by implementations of the systems and methods discussed herein may be (i) one in which one or more of the amino acid residues are substituted with a conserved or non-conserved amino acid residue (preferably a conserved amino acid residue) and such substituted amino acid residue may or may not be one encoded by the genetic code, (ii) one in which there are one or more modified amino acid residues, e.g., residues that are modified by the attachment of substituent groups, (iii) fragments of the 3DCNN-engineered proteins and/or (iv) one in which the 3DCNN-engineered protein is fused with another protein or polypeptide. The fragments include polypeptides generated via proteolytic cleavage (including multi-site proteolysis) of an original 3DCNN-engineered protein sequence. Variants may be post-translationally, or chemically modified. Such variants are deemed to be within the scope of those skilled in the art from the teaching herein.

As known in the art the "similarity" between two polypeptides is determined by comparing the amino acid sequence and its conserved amino acid substitutes of one polypeptide to a sequence of a second polypeptide. Variants are defined to include polypeptide sequences different from the original sequence, different from the original sequence in less than 40% of residues per segment of interest, different from the original sequence in less than 25% of residues per segment of interest, different by less than 10% of residues per segment of interest, or different from the original protein sequence in just a few residues per segment of interest and at the same time sufficiently homologous to the original sequence to preserve the functionality of the original sequence and/or the ability to bind to ubiquitin or to a ubiquitylated protein. Implementations of the systems and methods discussed herein may be used to generate or identify amino acid sequences that are at least 60%, 65%, 70%, 72%, 74%, 76%, 78%, 80%, 90%, 91%, 92%, 93%, 94%, 95%, 96%, 97%, 98%, or 99% similar or identical to the original amino acid sequence. The identity between two amino acid sequences is preferably determined by using the BLASTP algorithm [BLAST Manual, Altschul, S., et al., NCBI NLM NIH Bethesda, Md. 20894, Altschul, S., et al., J. Mol. Biol. 215: 403-410 (1990)].

The 3DCNN-engineered proteins generated or identified by implementations of the systems and methods discussed herein can be post-translationally modified. For example, post-translational modifications that fall within the scope of implementations of the systems and methods discussed herein include signal peptide cleavage, glycosylation, acetylation, isoprenylation, proteolysis, myristoylation, protein folding and proteolytic processing, etc. Some modifications or processing events require introduction of additional biological machinery. For example, processing events, such as signal peptide cleavage and core glycosylation, are examined by adding canine microsomal membranes or Xenopus egg extracts (U.S. Pat. No. 6,103,489) to a standard translation reaction.

The 3DCNN-engineered proteins generated or identified by implementations of the systems and methods discussed herein may include unnatural amino acids formed by post-translational modification or by introducing unnatural amino acids during translation. A variety of approaches are available for introducing unnatural amino acids during protein translation. By way of example, special tRNAs, such as tRNAs which have suppressor properties, suppressor tRNAs, have been used in the process of site-directed non-native amino acid replacement (SNAAR). In SNAAR, a unique codon is required on the mRNA and the suppressor tRNA, acting to target a non-native amino acid to a unique site during the protein synthesis (described in WO90/05785). However, the suppressor tRNA must not be recognizable by the aminoacyl tRNA synthetases present in the protein translation system. In certain cases, a non-native amino acid can be formed after the tRNA molecule is aminoacylated using chemical reactions which specifically modify the native amino acid and do not significantly alter the functional activity of the aminoacylated tRNA. These reactions are referred to as post-aminoacylation modifications. For example, the epsilon-amino group of the lysine linked to its cognate tRNA (tRNALYs), could be modified with an amine specific photoaffinity label.

An 3DCNN-engineered protein generated or identified by implementations of the systems and methods discussed herein may be conjugated with other molecules, such as proteins, to prepare fusion proteins. This may be accomplished, for example, by the synthesis of N-terminal or C-terminal fusion proteins provided that the resulting fusion protein retains the functionality of the 3DCNN-engineered protein.

3DCNN-Engineered Protein Mimetics

In some embodiments, the subject compositions are peptidomimetics of the 3DCNN-engineered proteins. Peptidomimetics are compounds based on, or derived from, peptides and proteins. The peptidomimetics generated or identified by implementations of the systems and methods discussed herein typically can be obtained by structural modification of a known 3DCNN-engineered protein sequence using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into non-peptide compounds with the activity of the parent 3DCNN-engineered protein.

Moreover, as is apparent from the present disclosure, mimetopes of the subject 3DCNN-engineered proteins can be provided. Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic. For illustrative purposes, peptide analogs generated or identified by implementations of the systems and methods discussed herein can be generated using, for example, benzodiazepines (e.g., see Freidinger et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988, p 123), C-7 mimics (Huffman et al. in Peptides: Chemistry and Biology, G. R. Marshall ed., ESCOM Publisher: Leiden, Netherlands, 1988, p. 105), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), β-turn dipeptide cores (Nagai et al. (1985) Tetrahedron Lett 26:647; and Sato et al. (1986) J Chem Soc Perkin Trans 1:1231), O-aminoalcohols (Gordon et al. (1985) Biochem Biophys Res Commun 126:419; and Dann et al. (1986) Biochem Biophys Res Commun 134:71), diaminoketones (Natarajan et al. (1984) Biochem Biophys Res Commun 124:141), and methyleneamino-modified (Roark et al. in Peptides: Chemistry and Biology, G. R. Marshall ed., ESCOM Publisher: Leiden, Netherlands, 1988, p 134). Also, see generally, Session III: Analytic and synthetic methods, in in Peptides: Chemistry and Biology, G. R. Marshall ed., ESCOM Publisher: Leiden, Netherlands, 1988)

In addition to a variety of side chain replacements which can be carried out to generate the 3DCNN-engineered protein peptidomimetics, implementations of the systems and methods discussed herein specifically contemplate the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

Nucleic Acids

In one embodiment, implementations of the systems and methods discussed herein may be used to generate or identify an isolated nucleic acid comprising a nucleotide sequence encoding a 3DCNN-engineered protein.

The nucleotide sequences encoding a 3DCNN-engineered protein can alternatively comprise sequence variations with respect to the original nucleotide sequences, for example, substitutions, insertions and/or deletions of one or more nucleotides, with the condition that the resulting polynucleotide encodes a polypeptide according to implementations of the systems and methods discussed herein. Accordingly, implementations of the systems and methods discussed herein may be used to generate or identify nucleotide sequences that are substantially identical to the nucleotide sequences recited herein and encodes a 3DCNN-engineered protein.

In the sense used in this description, a nucleotide sequence is "substantially identical" to any of the nucleotide sequences describe herein when its nucleotide sequence has a degree of identity with respect to the nucleotide sequence of at least 60%, of at least 70%, at least 85%, at least 95%, at least 96%, at least 97%, at least 98% or at least 99%. A nucleotide sequence that is substantially homologous to a nucleotide sequence encoding a 3DCNN-engineered protein can typically be isolated from a producer organism of the polypeptide generated or identified by implementations of the systems and methods discussed herein based on the information contained in the nucleotide sequence by means of introducing conservative or non-conservative substitutions, for example. Other examples of possible modifications include the insertion of one or more nucleotides in the sequence, the addition of one or more nucleotides in any of the ends of the sequence, or the deletion of one or more nucleotides in any end or inside the sequence. The identity between two nucleotide sequences is preferably determined by using the BLASTN algorithm [BLAST Manual, Altschul, S., et al., NCBI NLM NIH Bethesda, Md. 20894, Altschul, S., et al., J. Mol. Biol. 215: 403-410 (1990)].

In another aspect, implementations of the systems and methods discussed herein may be used to generate or identify a construct, comprising a nucleotide sequence encoding a 3DCNN-engineered protein, or derivative thereof. In a particular embodiment, the construct is operatively bound to transcription, and optionally translation, control elements. The construct can incorporate an operatively bound regulatory sequence of the expression of the nucleotide sequence generated or identified by implementations of the systems and methods discussed herein, thus forming an expression cassette.

A 3DCNN-engineered protein or chimeric 3DCNN-engineered protein may be prepared using recombinant DNA methods. Accordingly, nucleic acid molecules which encode a 3DCNN-engineered protein or chimeric 3DCNN-engineered protein may be incorporated into an appropriate expression vector which ensures good expression of the 3DCNN-engineered protein or chimeric 3DCNN-engineered protein.

Therefore, in another aspect, implementations of the systems and methods discussed herein may be used to generate or identify a vector, comprising the nucleotide sequence or the construct generated or identified by implementations of the systems and methods discussed herein. The choice of the vector will depend on the host cell in which it is to be subsequently introduced. In a particular embodiment, the vector generated or identified by implementations of the systems and methods discussed herein is an expression vector. Suitable host cells include a wide variety of prokaryotic and eukaryotic host cells. In specific embodiments, the expression vector is selected from the group consisting of a viral vector, a bacterial vector and a mammalian cell vector. Prokaryote- and/or eukaryote-vector based systems can be employed for use with implementations of the systems and methods discussed herein to produce polynucleotides, or their cognate polypeptides. Many such systems are commercially and widely available.

Further, the expression vector may be provided to a cell in the form of a viral vector. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. (See, e.g., WO 01/96584; WO 01/29058; and U.S. Pat. No. 6,326,193.

Vectors suitable for the insertion of the polynucleotides are vectors derived from expression vectors in prokaryotes such as pUC18, pUC19, Bluescript and the derivatives thereof, mp18, mp19, pBR322, pMB9, ColE1, pCR1, RP4, phages and "shuttle" vectors such as pSA3 and pAT28, expression vectors in yeasts such as vectors of the type of 2 micron plasmids, integration plasmids, YEP vectors, centromere plasmids and the like, expression vectors in insect cells such as vectors of the pAC series and of the pVL, expression vectors in plants such as pIBI, pEarleyGate, pAVA, pCAMBIA, pGSA, pGWB, pMDC, pMY, pORE series and the like, and expression vectors in eukaryotic cells based on viral vectors (adenoviruses, viruses associated to adenoviruses such as retroviruses and, particularly, lentiviruses) as well as non-viral vectors such as pSilencer 4.1-CMV (Ambion), pcDNA3, pcDNA3.1/hyg, pHMCV/Zeo, pCR3.1, pEFI/His, pIND/GS, pRc/HCMV2, pSV40/Zeo2, pTRACER-HCMV, pUB6/V5-His, pVAX1, pZeoSV2, pCI, pSVL and PKSV-10, pBPV-1, pML2d and pTDT1.

By way of illustration, the vector in which the nucleic acid sequence is introduced can be a plasmid which is or is not integrated in the genome of a host cell when it is introduced in the cell. Illustrative, non-limiting examples of vectors in which the nucleotide sequence or the gene construct generated or identified by implementations of the systems and methods discussed herein can be inserted include a tet-on inducible vector for expression in eukaryote cells.

In a particular embodiment, the vector is a vector useful for transforming animal cells.

The recombinant expression vectors may also contain nucleic acid molecules which encode a portion which provides increased expression of the 3DCNN-engineered protein or chimeric 3DCNN-engineered protein; increased solubility of the 3DCNN-engineered protein or chimeric 3DCNN-engineered protein; and/or aid in the purification of the 3DCNN-engineered protein or chimeric 3DCNN-engineered protein by acting as a ligand in affinity purification. For example, a proteolytic cleavage site may be inserted in the 3DCNN-engineered protein to allow separation of the 3DCNN-engineered protein or chimeric 3DCNN-engineered protein from the fusion portion after purification of the fusion protein. Examples of fusion expression vectors include pGEX (Amrad Corp., Melbourne, Australia), pMAL (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Additional promoter elements, i.e., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202, 5,928, 906). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

A promoter sequence exemplified in the experimental examples presented herein is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, implementations of the systems and methods discussed herein are not limited to the use of constitutive promoters. Inducible promoters may also be generated or identified via implementations of the systems and methods discussed herein. The use of an inducible promoter generated or identified via such systems or methods provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, implementations of the systems and methods discussed herein may allow the use of a tissue specific promoter, which promoter is active only in a desired tissue. Tissue specific promoters include, but are not limited to, the HER-2 promoter and the PSA associated promoter sequences.

In one embodiment, the expression of the nucleic acid is externally controlled. For example, in one embodiment, the expression is externally controlled using a doxycycline Tet-On system or other inducible or repressible expression system.

The recombinant expression vectors may also contain a selectable marker gene which facilitates the selection of transformed or transfected host cells. Suitable selectable marker genes are genes encoding proteins such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. The selectable markers may be introduced on a separate vector from the nucleic acid of interest.

Reporter genes are used for identifying potentially transfected cells and for evaluating the functionality of regulatory sequences. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Exemplary reporter genes may include genes encoding luciferase, beta-galactosidase, chloramphenicol acetyl transferase, secreted alkaline phosphatase, or fluorescent proteins including, but not limited to, green fluorescent protein gene (see, e.g., Ui-Tei et al., 2000 FEBS Lett. 479:79-82).

In one embodiment, the 3DCNN-engineered protein generated or identified by implementations of the systems and methods discussed herein is a reporter gene and is included in a suitable expression system. For example, in one embodiment, the 3DCNN-engineered protein generated or identified by such systems or methods is a blue fluorescent protein having increased fluorescent activity. In such an embodiment, a nucleotide sequence encoding the 3DCNN-engineered protein generated or identified by implementations of the systems and methods discussed herein may be incorporated into an expression system to allow for detection of a heterologous protein sequence.

Recombinant expression vectors may be introduced into host cells to produce a recombinant cell. The cells can be prokaryotic or eukaryotic. The vector generated or identified by implementations of the systems and methods discussed herein can be used to transform eukaryotic cells such as yeast cells, *Saccharomyces cerevisiae*, or mammal cells for example epithelial kidney 293 cells or U2OS cells, or prokaryotic cells such as bacteria, *Escherichia coli* or *Bacillus subtilis*, for example. Nucleic acid can be introduced into a cell using conventional techniques such as calcium phosphate or calcium chloride co-precipitation, DEAE-dextran-mediated transfection, lipofectin, electroporation or microinjection. Suitable methods for transforming and transfecting host cells may be found in Sambrook et al. (Molecular Cloning: A Laboratory Manual, 2nd Edition, Cold Spring Harbor Laboratory press (1989)), and other laboratory textbooks.

For example, a 3DCNN-engineered protein or chimeric 3DCNN-engineered protein generated or identified by implementations of the systems and methods discussed herein may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

Modified Blue Fluorescent Proteins

In one embodiment, implementations of the systems and methods discussed herein may be used to identify or generate a secBFP2 variant protein. In certain aspects the composition relates to a secBFP2 variant protein comprising one or more mutations that enhance stability. In certain aspects the secBFP2 variant protein displays one or more of enhanced stability, enhanced fluorescence, enhanced half-life, and slower photobleaching, relative to wild-type secBFP2.

In some embodiments, the secBFP2 variant protein comprises secBFP2 comprising one or more mutations. For example, in some embodiments, the secBFP2 variant protein comprises secBFP2 comprising one or more mutations at one more residues selected from: T18, S28, Y96, S114, V124, T127, D151, N173, and R198, in relation to full-length wild-type secBFP2. In one embodiment, full-length wild-type secBFP2 comprises the amino acid sequence of:

(SEQ ID NO: 1)
SEELIKENMHMKLYMEGTVDNHHFKCTSEGEGKPYEGTQTMRIKVVEGGPL

PFAFDILATSFLYGSKTFIDHTQGIPDFFKQSFPEGFTWERVTTYEDGGVL

TATQDTSLQDGSLIYNVKIRGVDFTSNGPVMQKKTLGWEAFTETLYPADGG

LEGRNDMALKLVGGSHLIANAKTTYRSKKPAKNLKMPGVYYVDYRLERIKE

ANDETYVEQHEVAVARYSDLPSKLGHKLN*

In certain embodiments, the notation of the mutations within the secBFP2 variant protein described herein are relative to SEQ ID NO: 1. For example a secBFP2 variant protein comprising a mutation at T18 refers to secBFP2 but having a mutation at a residue that correlates with the threonine at position 18 of full-length wild-type secBFP2 (SEQ ID NO: 1).

In some embodiments, the secBFP2 variant protein comprises secBFP2 comprising one or more mutations selected from: T18X, S28X, Y96X, S114X, V124X, T127X, D151X, N173X, and R198X, in relation to full-length wild-type secBFP2, where X is any amino acid. In some embodiments, the secBFP2 variant protein comprises secBFP2 comprising one or more mutations selected from: T18W, T18V, T18E, S28A, Y96F, S114V, S114T, V124T, V124Y, V124W, T127P, T127L, T127R, T127D, D151G, N173T, N173H, N173R, N173S, R198V and R198L, in relation to full-length wild-type secBFP2.

In one embodiment, the secBFP2 variant protein comprises secBFP2 comprising a T18X mutation, where X is any amino acid. In one embodiment, the secBFP2 variant protein comprises secBFP2 comprising a T18W mutation, T18V mutation, or a T18E mutation, in relation to full-length wild-type secBFP2.

For example, in one embodiment, the secBFP2 variant protein comprises:

(SEQ ID NO: 2)
SEELIKENMHMKLVMEGWVDNHHFKCTSEGEGKPYEGTQTMRIKVVEGGPL

PFAFDILATSFLYGSKTFIDHTQGIPDFFKQSFPEGFTWERVTTYEDGGVL

TATQDTSLQDGSLIYNVKIRGVDFTSNGPVMQKKTLGWEAFTETLYPADGG

LEGRNDMALKLVGGSHLIANAKTTYRSKKPAKNLKMPGVYYVDYRLERIKE

ANDETYVEQHEVAVARYSDLPSKLGHKLN, or a variant or fragment thereof.

For example, in one embodiment, the secBFP2 variant protein comprises:

(SEQ ID NO: 3)
SEELIKENMHMKLYMEGVVDNHHFKCTSEGEGKPYEGTQTMRIKVVEGGPL

PFAFDILATSFLYGSKTFIDHTQGIPDFFKQSFPEGFTWERVTTYEDGGVL

TATQDTSLQDGSLIYNVKIRGVDFTSNGPVMQKKTLGWEAFTETLYPADGG

LEGRNDMALKLVGGSHLIANAKTTYRSKKPAKNLKMPGVYYVDYRLERIKE

ANDETYVEQHEVAVARYSDLPSKLGHKLN, or a variant or fragment thereof.

For example, in one embodiment, the secBFP2 variant protein comprises:

(SEQ ID NO: 4)
SEELIKENMHMKLYMEGEVDNHHFKCTSEGEGKPYEGTQTMRIKVVEGGPL

PFAFDILATSFLYGSKTFIDHTQGIPDFFKQSFPEGFTWERVTTYEDGGVL

TATQDTSLQDGSLIYNVKIRGVDFTSNGPVMQKKTLGWEAFTETLYPADGG

LEGRNDMALKLVGGSHLIANAKTTYRSKKPAKNLKMPGVYYVDYRLERIKE

ANDETYVEQHEVAVARYSDLPSKLGHKLN, or a variant or fragment thereof.

In one embodiment, the secBFP2 variant protein comprises secBFP2 comprising a S28X mutation, where X is any amino acid. In one embodiment, the secBFP2 variant protein comprises secBFP2 comprising a S28A mutation in relation to full-length wild-type secBFP2.

For example, in one embodiment, the secBFP2 variant protein comprises:

(SEQ ID NO: 5)
SEELIKENMHMKLYMEGTVDNHHFKCTAEGEGKPYEGTQTMRIKVVEGGPL

PFAFDILATSFLYGSKTFIDHTQGIPDFFKQSFPEGFTWERVTTYEDGGVL

TATQDTSLQDGSLIYNVKIRGVDFTSNGPVMQKKTLGWEAFTETLYPADGG

LEGRNDMALKLVGGSHLIANAKTTYRSKKPAKNLKMPGVYYVDYRLERIKE

ANDETYVEQHEVAVARYSDLPSKLGHKLN, or a variant or fragment thereof.

In one embodiment, the secBFP2 variant protein comprises secBFP2 comprising a Y96X mutation, where X is any amino acid. In one embodiment, the secBFP2 variant protein comprises secBFP2 comprising a Y96F mutation in relation to full-length wild-type secBFP2.

For example, in one embodiment, the secBFP2 variant protein comprises:

(SEQ ID NO: 6)
SEELIKENMHMKLYMEGTVDNHHFKCTSEGEGKPYEGTQTMRIKVVEGGPL

PFAFDILATSFLYGSKTFIDHTQGIPDFFKQSFPEGFTWERVTTFEDGGVL

TATQDTSLQDGSLIYNVKIRGVDFTSNGPVMQKKTLGWEAFTETLYPADGG

LEGRNDMALKLVGGSHLIANAKTTYRSKKPAKNLKMPGVYYVDYRLERIKE

ANDETYVEQHEVAVARYSDLPSKLGHKLN, or a variant or fragment thereof.

In one embodiment, the secBFP2 variant protein comprises secBFP2 comprising a S114X mutation, where X is any amino acid. In one embodiment, the secBFP2 variant protein comprises secBFP2 comprising a S114V mutation or a S114T mutation, in relation to full-length wild-type secBFP2.

For example, in one embodiment, the secBFP2 variant protein comprises:

(SEQ ID NO: 7)
SEELIKENMHMKLYMEGTVDNHHFKCTSEGEGKPYEGTQTMRIKVVEGGPL

PFAFDILATSFLYGSKTFIDHTQGIPDFFKQSFPEGFTWERVTTYEDGGVL

TATQDTSLQDGVLIYNVKIRGVDFTSNGPVMQKKTLGWEAFTETLYPADGG

LEGRNDMALKLVGGSHLIANAKTTYRSKKPAKNLKMPGVYYVDYRLERIKE

ANDETYVEQHEVAVARYSDLPSKLGHKLN, or a variant or fragment thereof.

For example, in one embodiment, the secBFP2 variant protein comprises:

(SEQ ID NO: 8)
SEELIKENMHMKLYMEGTVDNHHFKCTSEGEGKPYEGTQTMRIKVVEGGPL

PFAFDILATSFLYGSKTFIDHTQGIPDFFKQSFPEGFTWERVTTYEDGGVL

TATQDTSLQDGTLIYNVKIRGVDFTSNGPVMQKKTLGWEAFTETLYPADGG

LEGRNDMALKLVGGSHLIANAKTTYRSKKPAKNLKMPGVYYVDYRLERIKE

ANDETYVEQHEVAVARYSDLPSKLGHKLN, or a variant or fragment thereof.

In one embodiment, the secBFP2 variant protein comprises secBFP2 comprising a V124X mutation, where X is any amino acid. In one embodiment, the secBFP2 variant protein comprises secBFP2 comprising a V124T mutation, a V124Y mutation, or a V124W mutation, in relation to full-length wild-type secBFP2.

For example, in one embodiment, the secBFP2 variant protein comprises:

(SEQ ID NO: 9)
SEELIKENMHMKLYMEGTVDNHHFKCTSEGEGKPYEGTQTMRIKVVEGGPL

PFAFDILATSFLYGSKTFIDHTQGIPDFFKQSFPEGFTWERVTTYEDGGVL

TATQDTSLQDGSLIYNVKIRGTDFTSNGPVMQKKTLGWEAFTETLYPADGG

LEGRNDMALKLVGGSHLIANAKTTYRSKKPAKNLKMPGVYYVDYRLERIKE

ANDETYVEQHEVAVARYSDLPSKLGHKLN, or a variant or fragment thereof.

For example, in one embodiment, the secBFP2 variant protein comprises:

(SEQ ID NO: 10)
SEELIKENMHMKLYMEGTVDNHHFKCTSEGEGKPYEGTQTMRIKVVEGGPL

PFAFDILATSFLYGSKTFIDHTQGIPDFFKQSFPEGFTWERVTTYEDGGVL

TATQDTSLQDGSLIYNVKIRGYDFTSNGPVMQKKTLGWEAFTETLYPADGG

LEGRNDMALKLVGGSHLIANAKTTYRSKKPAKNLKMPGVYYVDYRLERIKE

ANDETYVEQHEVAVARYSDLPSKLGHKLN, or a variant or fragment thereof.

For example, in one embodiment, the secBFP2 variant protein comprises:

(SEQ ID NO: 11)
SEELIKENMHMKLYMEGTVDNHHFKCTSEGEGKPYEGTQTMRIKVVEGGPL

PFAFDILATSFLYGSKTFIDHTQGIPDFFKQSFPEGFTWERVTTYEDGGVL

TATQDTSLQDGSLIYNVKIRGWDFTSNGPVMQKKTLGWEAFTETLYPADGG

LEGRNDMALKLVGGSHLIANAKTTYRSKKPAKNLKMPGVYYVDYRLERIKE

ANDETYVEQHEVAVARYSDLPSKLGHKLN, or a variant or fragment thereof.

In one embodiment, the secBFP2 variant protein comprises secBFP2 comprising a T127X mutation, where X is any amino acid. In one embodiment, the secBFP2 variant protein comprises secBFP2 comprising a T127P mutation, a T127L mutation, a T127R mutation, or a T127D mutation, in relation to full-length wild-type secBFP2.

For example, in one embodiment, the secBFP2 variant protein comprises:

(SEQ ID NO: 12)
SEELIKENMHMKLYMEGTVDNHHFKCTSEGEGKPYEGTQTMRIKVVEGGPL
PFAFDILATSFLYGSKTFIDHTQGIPDFFKQSFPEGFTWERVTTYEDGGVL
TATQDTSLQDGSLIYNVKIRGVDFPSNGPVMQKKTLGWEAFTETLYPADGG
LEGRNDMALKLVGGSHLIANAKTTYRSKKPAKNLKMPGVYYVDYRLERIKE
ANDETYVEQHEVAVARYSDLPSKLGHKLN, or a variant or fragment thereof.

For example, in one embodiment, the secBFP2 variant protein comprises:

(SEQ ID NO: 13)
SEELIKENMHMKLYMEGTVDNHHFKCTSEGEGKPYEGTQTMRIKVVEGGPL
PFAFDILATSFLYGSKTFIDHTQGIPDFFKQSFPEGFTWERVTTYEDGGVL
TATQDTSLQDGSLIYNVKIRGVDFLSNGPVMQKKTLGWEAFTETLYPADGG
LEGRNDMALKLVGGSHLIANAKTTYRSKKPAKNLKMPGVYYVDYRLERIKE
ANDETYVEQHEVAVARYSDLPSKLGHKLN, or a variant or fragment thereof.

For example, in one embodiment, the secBFP2 variant protein comprises:

(SEQ ID NO: 14)
SEEUKENMHIMKLYMEGTVDINHHFKCTSEGEGKPYEGTQTMRIKVVEG
GPLPFAFDILATSFLYGSKTFIDHTQGIPDFFKQSFPECIFTWERVTTY
EDGGVUFATQDTSLQDGSLIYNVKIRGVDFRSNGPVMQKKTLGWEAFTE
TLYPADGGLEGRNDMALKLVGGSHLIANAKTTYRSKKPAKNLKMPGVYV
VDYRLERMEANDETYVEQHEVAVARYSDLPSKLGHKLN, or a variant or fragment thereof.

For example, in one embodiment, the secBFP2 variant protein comprises:

(SEQ ID NO: 15)
SEELIKENMHMKLYMEGTVDINTIEFICCTSEGEGKPYEGTQMIRIKVV
EGGPLPFAFDILATSFLYGSKTFIDIHTQGIPDFFKQSFPEGFTWERVT
TYEDGGVLTATQDTSLQDGSLIYNVKIRGVDFDSNGPVMQKKTLGWEAF
TETLYPADGGLEGRNDMALKLVGGSFILIANAKTTYRSKKPAKNLKMPG
VYYVDYRLERIKEANDETYVEQHEVAVARYSDLPSKLGHKLN, or a variant or fragment thereof.

For example, in one embodiment, the secBFP2 variant protein comprises:

(SEQ ID NO: 16)
SEELIKENMHMKLYMEGTNIDINIIHFKCTSEGEGKPYEGTQMIRIKVV
EGGPLPFAFDILATSFLYGSKTFIDFHTQGIPDITKQSITEGFTWERVI
TYEDGGVLTATQDTSLQDGSLIYNYKIRGVDFTSNGPVMQKKTLGWEAF
TELYPAGGGLEGRNDMALKLVGGSHLIANAKFTYRSKKPAKNLKNIPGV
YYVDYRLERIKEANDETYVEQHEVAVARYSDLPSKLGHKILN, or a variant or fragment thereof.

In one embodiment, the secBFP2 variant protein comprises secBFP2 comprising a N173X mutation, where X is any amino acid. In one embodiment, the secBFP2 variant protein comprises secBFP2 comprising a N173T mutation, a N173H mutation, a N173R mutation, or a N173S mutation, in relation to full-length wild-type secBFP2.

For example, in one embodiment, the secBFP2 variant protein comprises:

(SEQ ID NO: 17)
SEELIKENMHMKLYMEGTVDNHHFKCTSEGEGKPYEGTQTMRIKVVEGG
PLPFAFDMATSFLYGSKTFIDHTQGIPDFFKQSFPEGFTWERVTTYEDG
GVLTATQDTSLQDGSLIYNVKIRGVDFISNGPVMQKKTLGWEAFTETLY
PADGGLEGRNDMALKLVGGSHLIATAKTTYRSKKPNLKMPGVYYVDYRL
ERIKEANDETYVEQITEVAVARYSDLPSKLGHKLN, or a variant or fragment thereof.

For example, in one embodiment, the secBFP2 variant protein comprises:

(SEQ ID NO: 18)
SEEUKENMEFMKLYNTEGTVDNHHFKCTSEGEGKPYEGTQTMRIKVVEG
GPLPFAFDILATSFLYGSKTHDHTQGIPDFFKQSFPEGFTWERVTTYED
GGVUFATQDTSLQDGSLIYNVKIRGVDFTSNGPVMQKKTLGWEAFTETL
YPADGGLEGRNDMALKUVGGSHLIAHAKTTYRSKKPAKNLKMPGVYYVD
YRLERIKEANDETYVEQHEVAVARYSDLPSKLGHKLN, or a variant or fragment thereof.

For example, in one embodiment, the secBFP2 variant protein comprises:

(SEQ ID NO: 19)
SEELIKENNIFINIKLYMEGINIDINTIHFKCTSEGEGKPYEGTQTNIR
IKVVEGGPLPFAFDILATSFLYGSKTFIDHTQGIPDFFKQSFPEGFTWE
RVTTYEDGGVLTATQDTSLQDGSLIYNVKIRGVDFTSNGPVMQKKTLGW
ENFTETLYPADGGLEGRNDMALKLVGGSHLIARAKTTYRSKKPAKNLKM
PGVYYVDYRLERIKEANDETYVEQHEVAVARYSDLPSKLGHKLN, or a variant or fragment thereof.

For example, in one embodiment, the secBFP2 variant protein comprises:

(SEQ ID NO: 20)
SEELIKENMHMKLYMEGTVDNHFIFKCTSEGEGKPYEGTQTMRIKVVEG
GPLPFAFDILATSFLYGSKTFIDHTQGWDFFKQSFPEGFTWERVTTNTD
GGVLTATQDTSLQDGSLIYNVKIRGVDFTSNGPVMQKKTLGWEAFTETL

-continued
YPADGGLEGRNDMALKLVGGSHLIA<u>S</u>AKTTYRSKKPNLKMPGVYYVDYR

LERIKEANDETYVEQHEVAVARYSDLPSKLGHKLN, or a variant or fragment thereof.

In one embodiment, the secBFP2 variant protein comprises secBFP2 comprising a R198X mutation, where X is any amino acid. In one embodiment, the secBFP2 variant protein comprises secBFP2 comprising a R198V mutation or a R198L mutation, in relation to full-length wild-type secBFP2.

For example, in one embodiment, the secBFP2 variant protein comprises:

(SEQ ID NO: 21)
SEELIKENMHMKLYMEGTVDNHHFKCTSEGEGKPYEGTQTMRIKVVEGG

PLPFAFDILATSFLYGSKTFIDHTQGIPDFFKQSFPEGFTWERVTIYED

GGVLTATQDTSLQDGSLIYNVMRGVDFTSNGPVMQKKTLGWEAFTETLY

PADGGLEGRNDMALKLVGGSHLIANAKTTYRSKKPAKNLKMPGVYYVDY

<u>V</u>LERIKEANDETYVEQHEVAVARYSDLPSKLGHKLN, or a variant or fragment thereof.

For example, in one embodiment, the secBFP2 variant protein comprises:

(SEQ ID NO: 22)
SEELAKENMIIMIKLYMEGTVDNHHFKCTSEGEGKPYEGFQTMRIKVVE

GGPLPFAFDILATSFLYGSKTFIDHTQGWDFFKQSFPEGFTWERVTTYE

DGGVLTATQDTSLQDGSLIYNVKIRGVDFTSNGPVMQKKILGWEAFTEI

LYPADGGLEGRNDMALKLVGGSHLIANAKTTYRSKKPAKNLJKMPGVYY

VDY<u>L</u>LERIKEANDETYVEQHEVAVARYSDLPSKLGHKLN, or a variant or fragment thereof.

In one embodiment, the secBFP2 variant protein comprises secBFP2 comprising a one or more, two or more, three or more, four or more, five or more, six or more, seven or more, eight or more, or all nine of the mutations of T18X, S28X, Y96X, S114X, V124X, T127X, D151X, N173X, and R198X in relation to full-length wild-type secBFP2, where X is any amino acid. In one embodiment, the secBFP2 variant protein comprises secBFP2 comprising a one or more, two or more, three or more, four or more, five or more, six or more, seven or more, eight or more, or nine or more of T18W, T18V, T18E, S28A, Y96F, S114V, S114T, V124T, V124Y, V124W, T127P, T127L, T127R, T127D, D151G, N173T, N173H, N173R, N173S, R198V and R198L, in relation to full-length wild-type secBFP2.

In one embodiment, the secBFP2 variant protein comprises secBFP2 comprising the mutations of T18X, S28X, S114X, V124X, T127X, D151X, N173X, and R198X, in relation to full-length wild-type secBFP2, where X is any amino acid. In one embodiment, the secBFP2 variant protein comprises secBFP2 comprising the mutations of T18W, S28A, S114V, V124T, T127P, D151G, N173T, and R198L, in relation to full-length wild-type secBFP2.

For example, in one embodiment, the secBFP2 variant protein comprises:

(SEQ ID NO: 23)
SEELIKENMHMKLYMEG<u>W</u>VDNHHFKCT<u>A</u>EGEGKFVEGTQTMRIKVVEGG

PLPFAFDILATSFLYGSKTHDHTQGIPDFFKQSFPEGFTWERVTTYEDG

GVLTATQDTSLQDG<u>V</u>LIYNVKIRG<u>T</u>DF<u>P</u>SNGPVMQKKTLGWEAFTETLY

PA<u>G</u>GGLEGRNDMALKLVGGSHLIA<u>T</u>AKTTYRSKKPAKNLKMPGVYYVDY

<u>LL</u>EREKEANDETYVEQHEVAVARYSDLPSKLGHKLN, or a variant or fragment thereof.

In one embodiment, the secBFP2 variant protein comprises secBFP2 comprising the mutations of S28X, S114X, T127X, and N173X in relation to full-length wild-type secBFP2, where X is any amino acid. In one embodiment, the secBFP2 variant protein comprises secBFP2 comprising the mutations of S28A, S114T, T127L, and N173H, in relation to full-length wild-type secBFP2.

For example, in one embodiment, the secBFP2 variant protein comprises:

(SEQ ID NO: 24)
SEMKENMITMKLYMEGTVDNHHFKCT<u>A</u>EGEGKPYEGTQTMRIKVVEGGP

LPFAFDILATSFLYGSKTFIDHTQGIPDFFKQSFPEGFTWERVTTYEDG

GVLTATQDTSLQDG<u>T</u>LIYNVKIRGYDF<u>L</u>SNGPNTIMKKTLGWEAFTETL

YPADGGLEGRNDMALKLVGGSEILIA<u>H</u>AKITYRSKKPAKNLKMPGVYYV

DYRLERIKEANDETYVEQHEVAVARYSDLPSKLGHKLN, or a variant or fragment thereof.

In one embodiment, the secBFP2 variant protein comprises secBFP2 comprising the mutations of S28X and S114X in relation to full-length wild-type secBFP2, where X is any amino acid. In one embodiment, the secBFP2 variant protein comprises secBFP2 comprising the mutations of S28A and S114T, in relation to full-length wild-type secBFP2.

For example, in one embodiment, the secBFP2 variant protein comprises:

(SEQ ID NO: 25)
SEELIKENMHMKLYMEGTVDNHHFKCT<u>A</u>EGEGKPYEGTQMIRIKVVEGG

PLPFAFDILATSFLYGSKTFIDHTQGIPDFFKQSFPEGFTWERVTIYED

GGNVLTATQDTSLQDG<u>T</u>LIYNVMRGVDFTSNGPVMQKKTLGWEAFTETL

YPADGGLEGRNDMALKLVGGSHLIANAKTTYRSKKPAKNLKMPGAIYYV

DYRILERIKEANDETYVEQHEVAVARYSDLPSKLGHKLN, or a variant or fragment thereof.

In one embodiment, the secBFP2 variant protein comprises secBFP2 comprising the mutations of S28X, S114X, and N173X in relation to full-length wild-type secBFP2, where X is any amino acid. In one embodiment, the secBFP2 variant protein comprises secBFP2 comprising the mutations of S28A, S114T, and N173H, in relation to full-length wild-type secBFP2.

For example, in one embodiment, the secBFP2 variant protein comprises:

(SEQ ID NO: 26)
SEELIKENMHMKLYMEGTVDNHHFKCT<u>A</u>EGEGKPYEGTQTMRIKVVEGG

PLPFAFDILATSFLYGSKTFIDHTQGIPDFFKQSFPEGFTWERVTTYED

```
GGVLTATQDTSLQDGTLIYNVKIRGNINTSNGPVMQKKTLGWEAFTETL

YPADGGLEGRINTAIALKLVGGSHLIAHAKTTYRSKKPAKNLKMPEGVY

YVRLERIKEANDETYVEQHEVAVARYSDLPSKLGHKLN,
``` or a variant or fragment thereof.

In one embodiment, the secBFP2 variant protein comprises secBFP2 comprising the mutations of S28X, Y96X, S114X, and N173X in relation to full-length wild-type secBFP2, where X is any amino acid. In one embodiment, the secBFP2 variant protein comprises secBFP2 comprising the mutations of S28A, Y96F, S114T, and N173H, in relation to full-length wild-type secBFP2.

For example, in one embodiment, the secBFP2 variant protein comprises:

```
                                    (SEQ ID NO: 27)
SEELIKENMHMKLYMEGTVDNHHFKCTAEGEGKPYEGTQMRIKVVEGGP

LPFAFDILATSFLYGSKTFIDHTQGIPDFFKQSFPEGFTWERVTTFEDG

GVLTATQDTSLQDGTLIYNVKIRGVDFTSNGPVMQKKTLGWEAFTETLY

PADGGLEGRNDMALKLVGGSHLIAHAKTTYRSKKPAKNLKMPGVYYVDY

RLERIKEANDETYVEQHEVAVARYSDLPSKLGHKLN,
``` or a variant or fragment thereof.

In one embodiment, the secBFP2 variant protein comprises secBFP2 comprising the mutations of S28X, Y96X, S114X, T127X, and N173X in relation to full-length wild-type secBFP2, where X is any amino acid. In one embodiment, the secBFP2 variant protein comprises secBFP2 comprising the mutations of S28A, Y96F, S114T, T127L, and N173H, in relation to full-length wild-type secBFP2.

For example, in one embodiment, the secBFP2 variant protein comprises:

```
                                    (SEQ ID NO: 28)
SEELIKENMHMKLYMEGTVDNHHFKCTAEGEGKPYEGTWISARIKVVEG

GPLPFAFDILATSFLYGSKTFIDHTQGIPDIFFKQSFPEGFTWERVTTF

EDGGVLTATQDTSLQDGTLIYNVKIRGVDFLSNGPVMQKKTLGWEAFTE

FLYPADGGLEGRNDMALKUVQGSHLIAHAKTTYRSKKPAKNLKMPGVYY

VDYRLERIKEANDETYVEQHEVAVARYSDLPSKLGHKLN,
``` or a variant or fragment thereof.

In one embodiment, compositions generated or identified by implementations of the systems and methods discussed herein include an isolated nucleic acid molecule comprising a nucleotide sequence encoding a secBFP2 variant protein. In various embodiments, the nucleic acid molecule comprises a sequence encoding for at least one amino acid sequence as set forth in SEQ ID NO:2 through SEQ ID NO:28, or a variant or fragment thereof.

A fusion protein, which includes a fluorescent protein variant operatively linked to one or more polypeptides of interest also is provided. The polypeptides of the fusion protein can be linked through peptide bonds, or the fluorescent protein variant can be linked to the polypeptide of interest through a linker molecule. In one embodiment, the fusion protein is expressed from a recombinant nucleic acid molecule containing a polynucleotide encoding a fluorescent protein variant operatively linked to one or more polynucleotides encoding one or more polypeptides of interest.

A polypeptide of interest can be any polypeptide, including, for example, a peptide tag such as a polyhistidine peptide, or a cellular polypeptide such as an enzyme, a G-protein, a growth factor receptor, or a transcription factor; and can be one of two or more proteins that can associate to form a complex. In one embodiment, the fusion protein is a tandem fluorescent protein variant construct, which includes a donor fluorescent protein variant, an acceptor fluorescent protein variant, and a peptide linker moiety coupling said donor and said acceptor, wherein cyclized amino acids of the donor emit light characteristic of said donor, and wherein the donor and the acceptor exhibit fluorescence resonance energy transfer when the donor is excited, and the linker moiety does not substantially emit light to excite the donor. As such, a fusion protein generated or identified by implementations of the systems and methods discussed herein can include two or more operatively linked fluorescent protein variants, which can be linked directly or indirectly, and can further comprise one or more polypeptides of interest.

Kits

In some implementations, kits may be provided to facilitate and/or standardize use of compositions provided or identified by implementations of the systems and methods discussed herein, as well as facilitate the methods discussed herein. Materials and reagents to carry out these various methods can be provided in kits to facilitate execution of the methods. As used herein, the term "kit" is used in reference to a combination of articles that facilitate a process, assay, analysis or manipulation.

Kits can contain chemical reagents (e.g., polypeptides or polynucleotides) as well as other components. In addition, kits discussed herein can also include, for example but not limited to, apparatus and reagents for sample collection and/or purification, apparatus and reagents for product collection and/or purification, reagents for bacterial cell transformation, reagents for eukaryotic cell transfection, previously transformed or transfected host cells, sample tubes, holders, trays, racks, dishes, plates, instructions to the kit user, solutions, buffers or other chemical reagents, suitable samples to be used for standardization, normalization, and/or control samples. Kits can also be packaged for convenient storage and safe shipping, for example, in a box having a lid.

In some embodiments, for example, kits discussed herein can provide a fluorescent protein generated or identified by implementations of the systems and methods discussed herein, a polynucleotide vector (e.g., a plasmid) encoding a fluorescent protein generated or identified by implementations of the systems and methods discussed herein, bacterial cell strains suitable for propagating the vector, and reagents for purification of expressed fusion proteins. In some embodiments, a kit as discussed herein can provide the reagents necessary to conduct mutagenesis of an Anthozoan fluorescent protein in order to generate a protein variant having a reduced propensity to oligomerize.

A kit can contain one or more compositions generated or identified by implementations of the systems and methods discussed herein, for example, one or a plurality of fluorescent protein variants, which can be a portion of a fusion protein, or one or a plurality of polynucleotides that encode the polypeptides. The fluorescent protein variant can be a mutated fluorescent protein having a reduced propensity to oligomerize, such as a non-oligomerizing monomer, or can be a tandem dimer fluorescent protein and, where the kit comprises a plurality of fluorescent protein variants, the plurality can be a plurality of the mutated fluorescent protein variants, or of the tandem dimer fluorescent proteins, or a combination thereof.

A kit as discussed herein also can contain one or a plurality of recombinant nucleic acid molecules, which encode, in part, fluorescent protein variants, which can be the same or different, and can further include, for example, an operatively linked second polynucleotide containing or encoding a restriction endonuclease recognition site or a recombinase recognition site, or any polypeptide of interest. In addition, the kit can contain instructions for using the components of the kit, particularly the compositions generated or identified by implementations of the systems and methods discussed herein that are contained in the kit.

Such kits can be particularly useful where they provide a plurality of different fluorescent protein variants because the artisan can conveniently select one or more proteins having the fluorescent properties desired for a particular application. Similarly, a kit containing a plurality of polynucleotides encoding different fluorescent protein variants provides numerous advantages. For example, the polynucleotides can be engineered to contain convenient restriction endonuclease or recombinase recognition sites, thus facilitating operative linkage of the polynucleotide to a regulatory element or to a polynucleotide encoding a polypeptide of interest or, if desired, for operatively linking two or more the polynucleotides encoding the fluorescent protein variants to each other.

Uses of Fluorescent Protein Variants

A fluorescent protein variant generated or identified by implementations of the systems and methods discussed herein is useful in any method that employs a fluorescent protein. Thus, the fluorescent protein variants, including the monomeric, dimeric, and tandem dimer fluorescent proteins, are useful as fluorescent markers in the many ways fluorescent markers already are used, including, for example, coupling fluorescent protein variants to antibodies, polynucleotides or other receptors for use in detection assays such as immunoassays or hybridization assays, or to track the movement of proteins in cells. For intracellular tracking studies, a first (or other) polynucleotide encoding the fluorescent protein variant is fused to a second (or other) polynucleotide encoding a protein of interest and the construct, if desired, can be inserted into an expression vector. Upon expression inside the cell, the protein of interest can be localized based on fluorescence, without concern that localization of the protein is an artifact caused by oligomerization of the fluorescent protein component of the fusion protein. In one embodiment of this method, two proteins of interest independently are fused with two fluorescent protein variants that have different fluorescent characteristics.

The fluorescent protein variants generated or identified by implementations of the systems and methods discussed herein are useful in systems to detect induction of transcription. For example, a nucleotide sequence encoding a non-oligomerizing monomeric, dimeric or tandem dimeric fluorescent protein can be fused to a promoter or other expression control sequence of interest, which can be contained in an expression vector, the construct can be transfected into a cell, and induction of the promoter (or other regulatory element) can be measured by detecting the presence or amount of fluorescence, thereby allowing a means to observe the responsiveness of a signaling pathway from receptor to promoter.

A fluorescent protein variant generated or identified by implementations of the systems and methods discussed herein also is useful in applications involving FRET, which can detect events as a function of the movement of fluorescent donors and acceptors towards or away from each other. One or both of the donor/acceptor pair can be a fluorescent protein variant. Such a donor/acceptor pair provides a wide separation between the excitation and emission peaks of the donor, and provides good overlap between the donor emission spectrum and the acceptor excitation spectrum.

FRET can be used to detect cleavage of a substrate having the donor and acceptor coupled to the substrate on opposite sides of the cleavage site. Upon cleavage of the substrate, the donor/acceptor pair physically separate, eliminating FRET. Such an assay can be performed, for example, by contacting the substrate with a sample, and determining a qualitative or quantitative change in FRET (see, for example, U.S. Pat. No. 5,741,657, which is incorporated herein by reference). A fluorescent protein variant donor/acceptor pair also can be part of a fusion protein coupled by a peptide having a proteolytic cleavage site (see, for example, U.S. Pat. No. 5,981,200, which is incorporated herein by reference). FRET also can be used to detect changes in potential across a membrane. For example, a donor and acceptor can be placed on opposite sides of a membrane such that one translates across the membrane in response to a voltage change, thereby producing a measurable FRET (see, for example, U.S. Pat. No. 5,661,035, which is incorporated herein by reference).

In other embodiments, a fluorescent protein generated or identified by implementations of the systems and methods discussed herein is useful for making fluorescent sensors for protein kinase and phosphatase activities or indicators for small ions and molecules such as $Ca^{2+}$, $Zn^{2+}$, cyclic 3', 5'-adenosine monophosphate, and cyclic 3', 5'-guanosine monophosphate.

Fluorescence in a sample generally is measured using a fluorimeter, wherein excitation radiation from an excitation source having a first wavelength, passes through excitation optics, which cause the excitation radiation to excite the sample. In response, a fluorescent protein variant in the sample emits radiation having a wavelength that is different from the excitation wavelength. Collection optics then collect the emission from the sample. The device can include a temperature controller to maintain the sample at a specific temperature while it is being scanned, and can have a multi-axis translation stage, which moves a microtiter plate holding a plurality of samples in order to position different wells to be exposed. The multi-axis translation stage, temperature controller, auto-focusing feature, and electronics associated with imaging and data collection can be managed by an appropriately programmed digital computer, which also can transform the data collected during the assay into another format for presentation. This process can be miniaturized and automated to enable screening many thousands of compounds in a high throughput format. Some methods of performing assays on fluorescent materials include Lakowicz, "Principles of Fluorescence Spectroscopy" (Plenum Press 1983); Herman, "Resonance energy transfer microscopy" In "Fluorescence Microscopy of Living Cells in Culture" Part B, Meth. Cell Biol. 30:219-243 (ed. Taylor and Wang; Academic Press 1989); Turro, "Modern Molecular Photochemistry" (Benjamin/Cummings Publ. Co., Inc. 1978), pp. 296-361, each of which is incorporated herein by reference.

Accordingly, the present disclosure also provides implementations of a method for identifying the presence of a molecule in a sample. Such a method can be performed, for example, by linking a fluorescent protein variant generated or identified by implementations of the systems and methods discussed hereinto the molecule and detecting fluorescence due to the fluorescent protein variant in a sample suspected of containing the molecule. The molecule to be detected can be a polypeptide, a polynucleotide, or any other molecule, including, for example, an antibody, an enzyme, or a receptor, and the fluorescent protein variant can be a tandem dimer fluorescent protein.

The sample to be examined can be any sample, including a biological sample, an environmental sample, or any other sample for which it is desired to determine whether a particular molecule is present therein. Preferably, the sample includes a cell or an extract thereof. The cell can be obtained from a vertebrate, including a mammal such as a human, or from an invertebrate, and can be a cell from a plant or an animal. The cell can be obtained from a culture of such cells, for example, a cell line, or can be isolated from an organism. As such, the cell can be contained in a tissue sample, which can be obtained from an organism by any means commonly used to obtain a tissue sample, for example, by biopsy of a human. Where the method is performed using an intact living cell or a freshly isolated tissue or organ sample, the presence of a molecule of interest in living cells can be identified, thus providing a means to determine, for example, the intracellular compartmentalization of the molecule. The use of the fluorescent protein variants generated or identified by implementations of the systems and methods discussed herein for such a purpose provides a substantial advantage in that the likelihood of aberrant identification or localization due to oligomerization the fluorescent protein is greatly minimized.

A fluorescent protein variant can be linked to the molecule directly or indirectly, using any linkage that is stable under the conditions to which the protein-molecule complex is to be exposed. Thus, the fluorescent protein and molecule can be linked via a chemical reaction between reactive groups present on the protein and molecule, or the linkage can be mediated by linker moiety, which contains reactive groups specific for the fluorescent protein and the molecule. It will be recognized that the appropriate conditions for linking the fluorescent protein variant and the molecule are selected depending, for example, on the chemical nature of the molecule and the type of linkage desired. Where the molecule of interest is a polypeptide, a convenient means for linking a fluorescent protein variant and the molecule is by expressing them as a fusion protein from a recombinant nucleic acid molecule, which comprises a polynucleotide encoding, for example, a tandem dimer fluorescent protein operatively linked to a polynucleotide encoding the polypeptide molecule.

A method of identifying an agent or condition that regulates the activity of an expression control sequence also is provided. Such a method can be performed, for example, by exposing a recombinant nucleic acid molecule, which includes a polynucleotide encoding a fluorescent protein variant operatively linked to an expression control sequence, to an agent or condition suspected of being able to regulate expression of a polynucleotide from the expression control sequence and detecting fluorescence of the fluorescent protein variant due to such exposure. Such a method is useful, for example, for identifying chemical or biological agents, including cellular proteins, that can regulate expression from the expression control sequence, including cellular factors involved in the tissue specific expression from the regulatory element. As such, the expression control sequence can be a transcription regulatory element such as a promoter, enhancer, silencer, intron splicing recognition site, polyadenylation site, or the like; or a translation regulatory element such as a ribosome binding site.

The fluorescent protein variants generated or identified by implementations of the systems and methods discussed herein also are useful in a method of identifying a specific interaction of a first molecule and a second molecule. Such a method can be performed, for example, by contacting the first molecule, which is linked to a donor first fluorescent protein variant, and the second molecule, which is linked to an acceptor second fluorescent protein variant, under conditions that allow a specific interaction of the first molecule and second molecule; exciting the donor; and detecting fluorescence or luminescence resonance energy transfer from the donor to the acceptor, thereby identifying a specific interaction of the first molecule and the second molecule. The conditions for such an interaction can be any conditions under which is expected or suspected that the molecules can specifically interact. In particular, where the molecules to be examined are cellular molecules, the conditions generally are physiological conditions. As such, the method can be performed in vitro using conditions of buffer, pH, ionic strength, and the like, that mimic physiological conditions, or the method can be performed in a cell or using a cell extract.

Luminescence resonance energy transfer entails energy transfer from a chemiluminescent, bioluminescent, lanthanide, or transition metal donor to the red fluorescent protein moiety. The longer wavelengths of excitation of red fluorescent proteins permit energy transfer from a greater variety of donors and over greater distances than possible with green fluorescent protein variants. Also, the longer wavelengths of emission is more efficiently detected by solid-state photodetectors and is particularly valuable for in vivo applications where red light penetrates tissue far better than shorter wavelengths. Chemiluminescent donors include but are not limited to luminol derivatives and peroxyoxalate systems. Bioluminescent donors include but are not limited to aequorin, obelin, firefly luciferase, *Renilla* luciferase, bacterial luciferase, and variants thereof. Lanthanide donors include but are not limited to terbium chelates containing ultraviolet-absorbing sensitizer chromophores linked to multiple liganding groups to shield the metal ion from solvent water. Transition metal donors include but are not limited to ruthenium and osmium chelates of oligopyridine ligands. Chemiluminescent and bioluminescent donors need no excitation light but are energized by addition of substrates, whereas the metal-based systems need excitation light but offer longer excited state lifetimes, facilitating time-gated detection to discriminate against unwanted background fluorescence and scattering.

The first and second molecules can be cellular proteins that are being investigated to determine whether the proteins specifically interact, or to confirm such an interaction. Such first and second cellular proteins can be the same, where they are being examined, for example, for an ability to oligomerize, or they can be different where the proteins are being examined as specific binding partners involved, for example, in an intracellular pathway. The first and second molecules also can be a polynucleotide and a polypeptide, for example, a polynucleotide known or to be examined for transcription regulatory element activity and a polypeptide known or being tested for transcription factor activity. For example, the first molecule can comprise a plurality of nucleotide sequences, which can be random or can be variants of a known sequence, that are to be tested for transcription regulatory element activity, and the second molecule can be a transcription factor, such a method being useful for identifying novel transcription regulatory elements having desirable activities.

The present disclosure also provides implementations of a method for determining whether a sample contains an enzyme. Such a method can be performed, for example, by contacting a sample with a tandem fluorescent protein variant generated or identified by implementations of the systems and methods discussed herein; exciting the donor, and determining a fluorescence property in the sample, wherein the presence of an enzyme in the sample results in a change in the degree of fluorescence resonance energy transfer. Similarly, the present disclosure provides implementations of a method for determining the activity of an enzyme in a cell. Such a method can be performed, for example, providing a cell that expresses a tandem fluorescent protein variant construct, wherein the peptide linker moiety comprises a cleavage recognition amino acid sequence specific for the enzyme coupling the donor and the acceptor; exciting said donor, and determining the degree of fluorescence resonance energy transfer in the cell, wherein the presence of enzyme activity in the cell results in a change in the degree of fluorescence resonance energy transfer.

EXPERIMENTAL EXAMPLES

Implementations of the systems and methods discussed herein are further described in detail by reference to the following experimental examples. These examples are provided for purposes of illustration only, and are not intended to be limiting unless otherwise specified. Thus, the systems and methods discussed herein should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize implementations of the systems and methods discussed herein. The following working examples therefore, specifically point out the exemplary embodiments of the systems and methods discussed herein, and are not to be construed as limiting in any way the remainder of the disclosure.

Example 1: Protein Engineering Using Neural Networks

To empirically validate the neural network, three different model proteins were chosen, each representing a distinct protein engineering challenge. The first validation model protein was tem-1 beta lactamase in large part because 1) the susceptibility to the antibiotic is directly related to the overall stability of the protein and 2) the protein has been well-characterized in illuminating both stabilizing and destabilizing mutations. Next, stability was improved to repurpose the metalloprotein phosphomannose isomerase into a reporter for incorporation of the noncanonical amino acid, L-DOPA. However, the poor stability of the enzyme prevents its use to act as a reporter. The final protein case is an improvement to a blue fluorescent protein variant, secBFP2. Though blue fluorescent proteins have been well characterized, rapid photobleaching, slow maturation and folding, and relatively dim fluorescence prevent more widespread use.

First, the true negative rate of the neural network was assessed by isolating the analysis to residues where the wild type amino acid has been experimentally validated as the best residue at the position. This was tested using previously published mutational scans in tem-1 β-lactamase where the effect of each individual amino acid change was quantitated with organismal fitness. Of the 263 positions tested in tem-1, 136 sites had a relative fitness value less than zero (i.e., sites that could not tolerate mutations away from the wild type residue without a cost to organismal fitness). This collection of 136 sites constituted the complete collection of true negatives in tem-1 beta lactamase and for each discrete change made to the neural network, the true negative sensitivity was benchmarked. The final version accurately identified 92.6% of the 136 true negatives, nearly a 30% increase over the initial models. Thus, the developed model has an increased ability to identify sites within a protein that are not amenable to mutation.

Figure 3A:
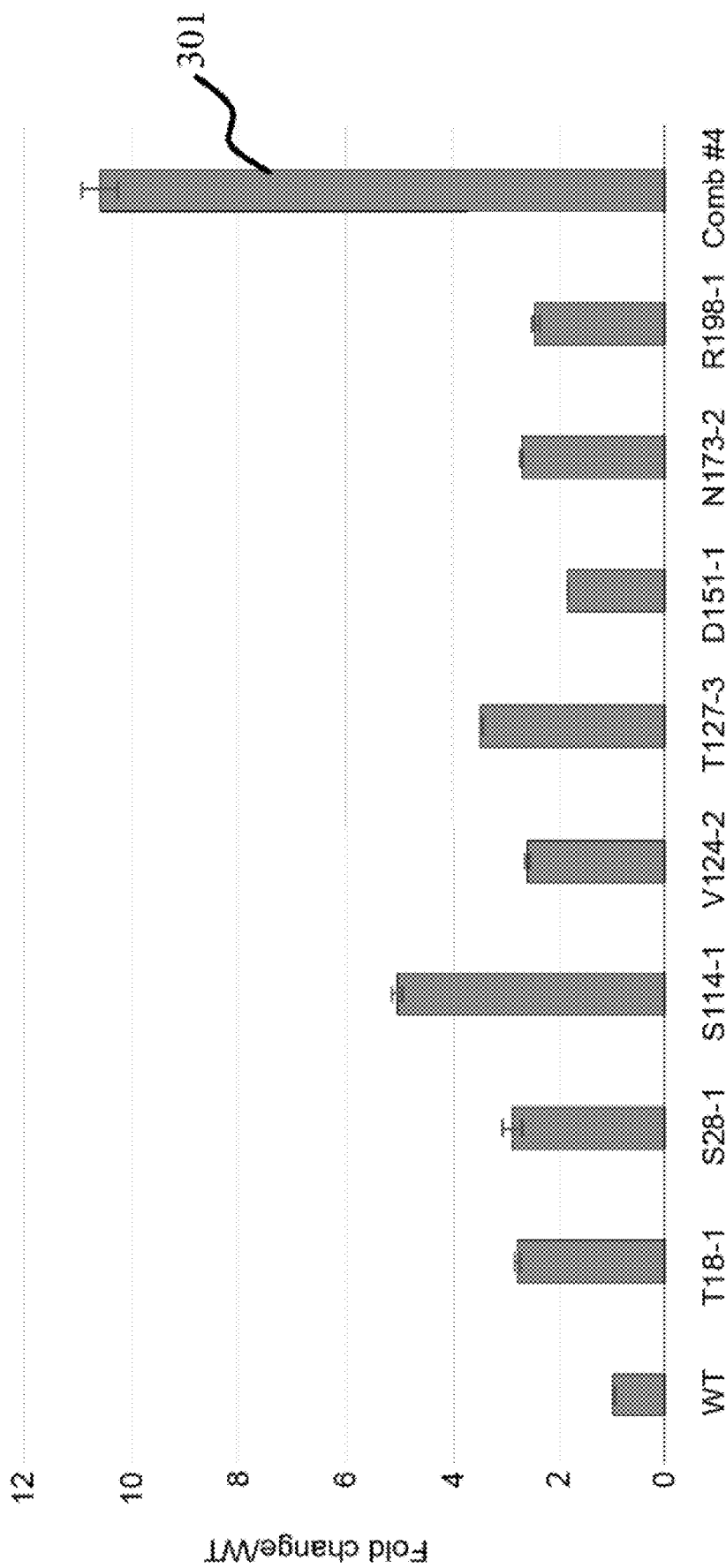
FIG. 3A is another graph of experimental results of an implementation of a method and system for increasing synthesized protein characteristics.
Figure 3B:
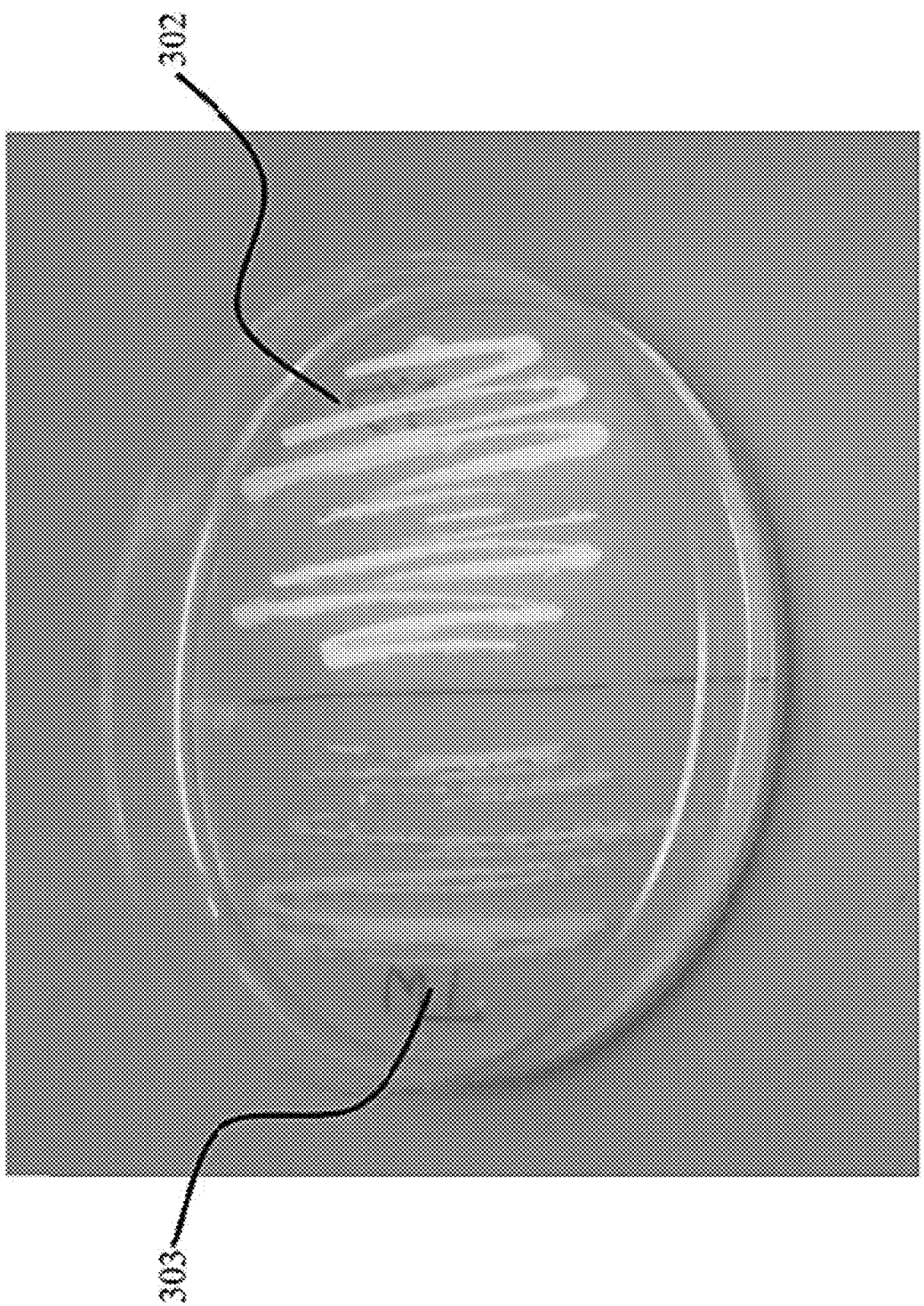
FIG. 3B is a photograph of a protein synthesized using modifications suggested by an implementation of a system for increasing synthesized protein characteristics.

The results of the experiment are shown in FIG. 3A and FIG. 3B. FIG. 3A shows a bar graph of sites predicted by the neural network to improve BFP fluorescence, and by how much. The rightmost bar 301 shows the improvement in fluorescence observed by implementing a particular combination of amino acid substitutions to the wild type protein, each suggested individually by the neural network. A visual representation of the improvement is shown in FIG. 3B. The modified blue fluorescent protein 302 glows far brighter than the wild type blue fluorescent protein 303.

Figure 4A:
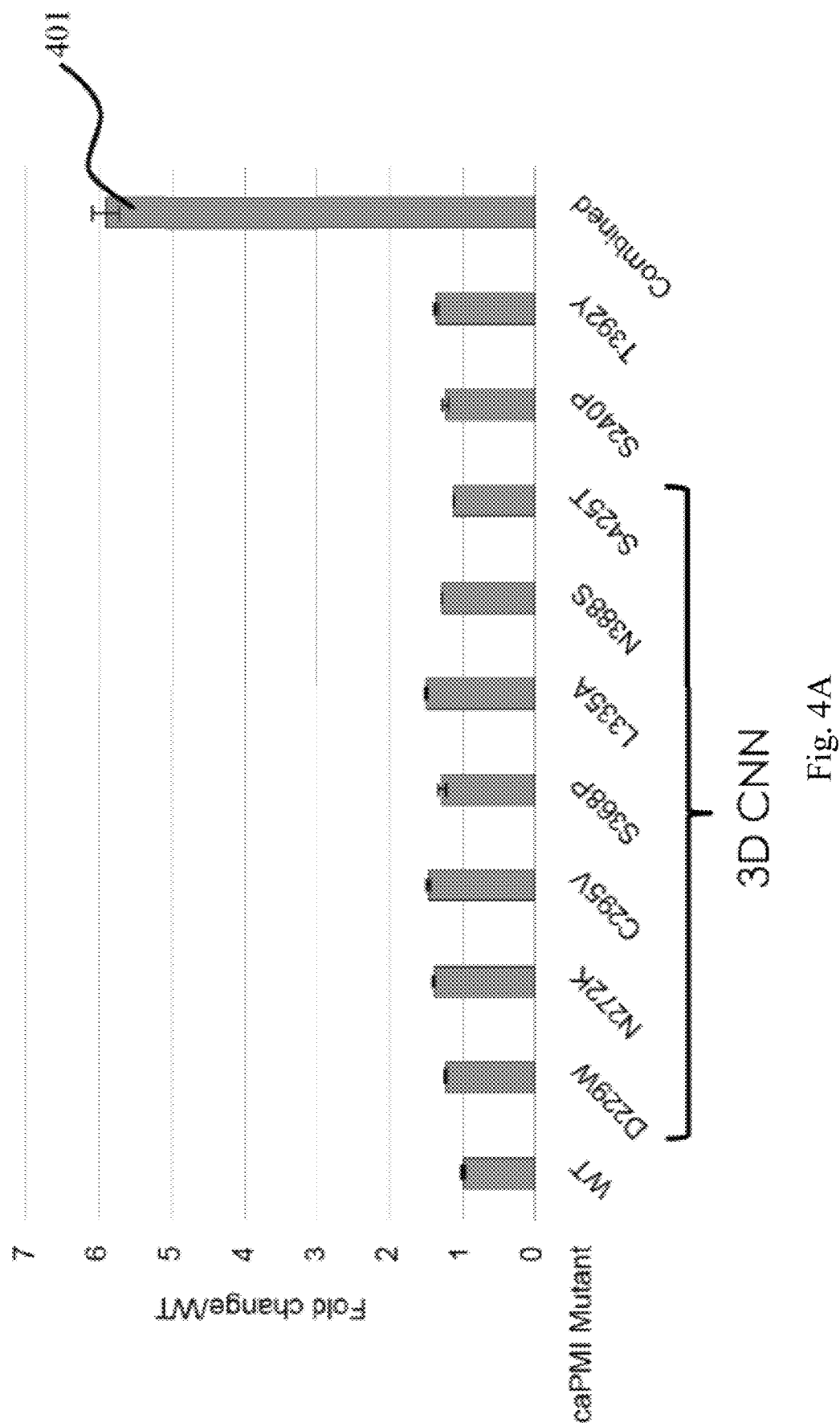
FIG. 4A is another graph of experimental results of an implementation of a method and system for increasing synthesized protein characteristics.
Figure 4B:
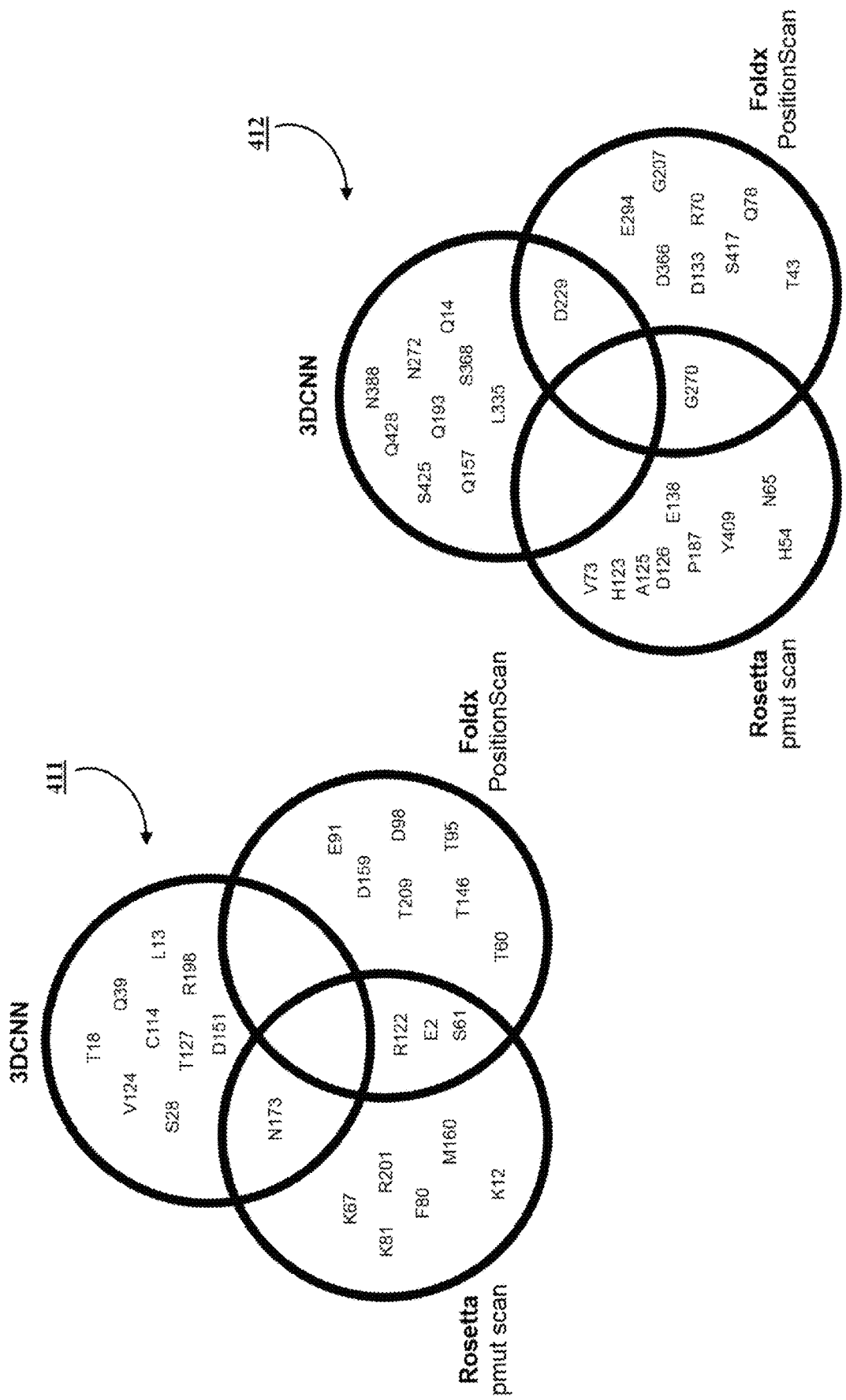
FIG. 4B is a diagram of suggested protein modifications suggested by an implementation of a system for increasing synthesized protein characteristics.

Additional results are shown in FIG. 4A and FIG. 4B. The bar graph in FIG. 4B shows the neural network proposed improvements to phosphomannose isomerase (PMI). The individual stabilizing mutations each provide a 15% to 50% increase over the wild type, but when used in combination (bar 401), the improvements are additive, leading to a significant improvement in stability of nearly 600%.

The Venn diagrams 411 (blue fluorescent protein, pdb: 3m24) and 412 (phosphomannose isomerase, pdb: 1pmi) in FIG. 4B illustrate that the neural network predicts unique candidate residues not identified by other computational protein stabilization techniques (Foldx PositionScan and Rosetta pmut scan).

Figure 5:
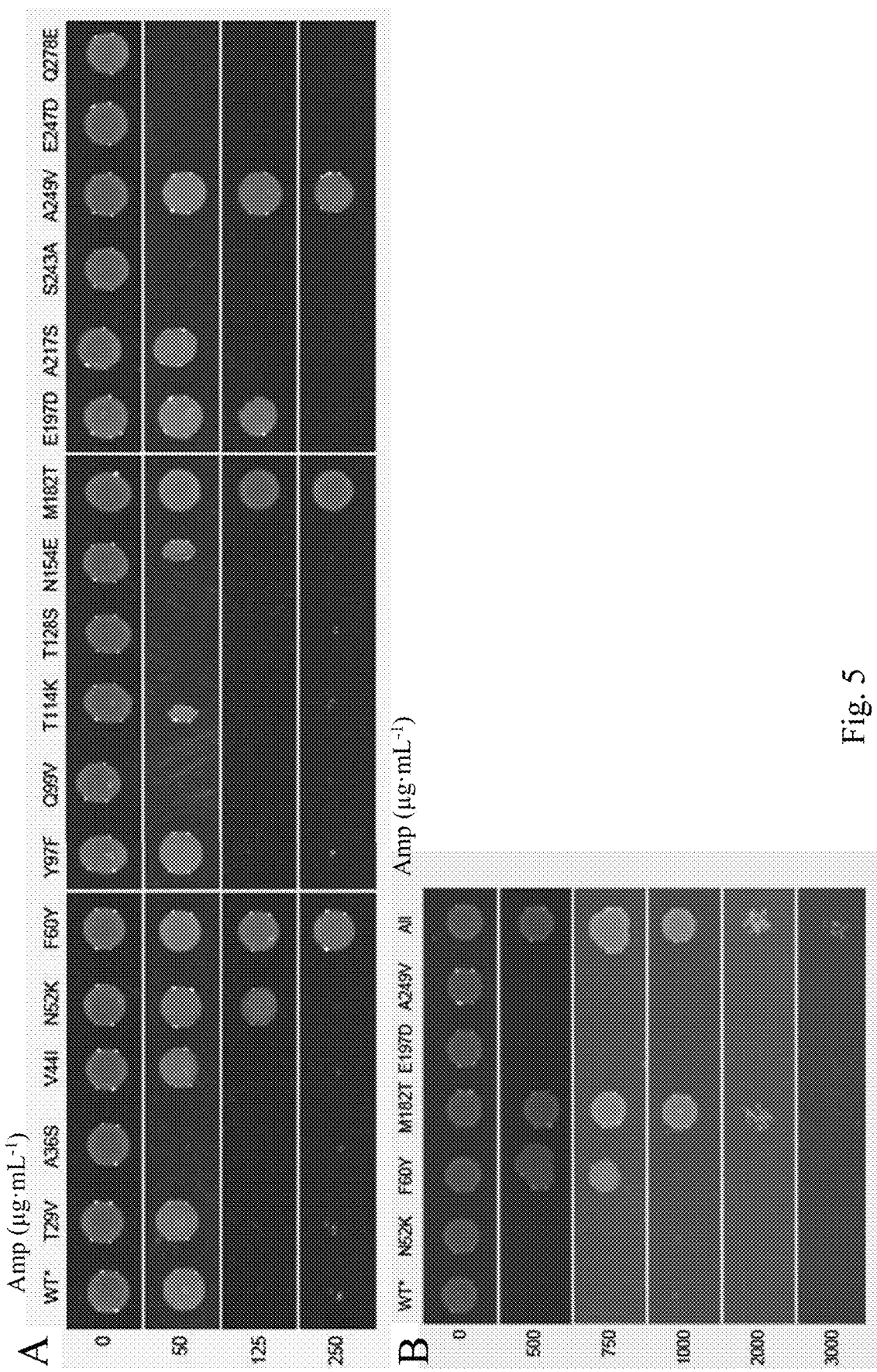
FIG. 5 is a set of photographs of experimental results of an implementation of a system for increasing synthesized protein characteristics.

FIG. 5 illustrates that the TEM-1 β-lactamase variants identified by the neural network enabled E. coli growth at higher ampicillin concentrations than the ancestral protein. E. coli expressing singly mutagenized β-lactamase mutants N52K, F60Y, M182T, E197D or A249V could each grow on ampicillin concentrations at or greater than 125 ug/mL; a concentration at which E. coli expressing the ancestral enzyme, labelled 'WT,' could not grow. E. coli expressing a single enzyme variant containing all five of these mutations (N52K, F60Y, M182T, E197D and A249V, labelled 'All') could grow at 3000 ug/mL ampicillin concentrations. In other words, the neural network improved a phenotype associated with catalysis, in the present embodiment a phenotype that allows E. coli to exhibit greater resistance to an antibiotic, ampicillin.

Figure 6:
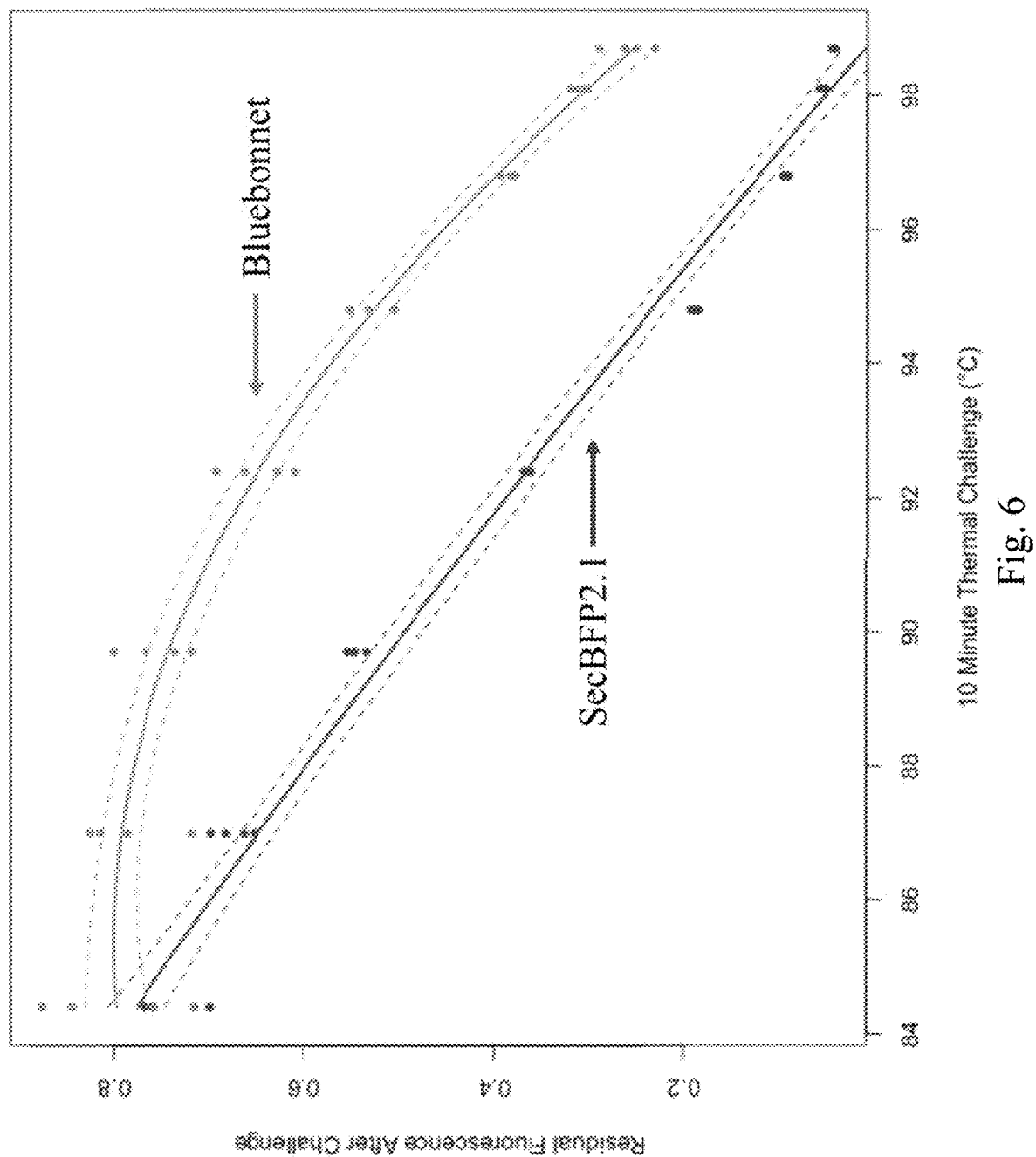
FIGS. 6 and 7 are graphs of experimental results of implementations of a system for increasing synthesized protein characteristics.

FIG. 6 shows that the neural network improved the thermal stability of a blue fluorescent protein. In one example, residual fluorescence—after a 10 minute thermal challenge—was less for the ancestral protein, SecBFP2.1, than for the derived protein, Bluebonnet. Purified blue fluorescent proteins were diluted to 0.01 mg/mL in PBS pH 7.4 and 100 uL aliquots were heat treated for 10 minutes in PCR strips on a thermal gradient using a thermal cycler. The fluorescence of thermally challenged variants and controls incubated at room temperature were assayed using excitation and emission wavelengths of 402 nm and 457 nm, respectively. Fluorescence readings were normalized to the mean of solutions incubated at room temperature (e.g., a measurement of 0.8 indicates that a heat treated protein retained 80% of its untreated fluorescence). As shown in FIG. 6, Bluebonnet exhibited greater thermal stability versus SecBFP2.1 across an entire range of temperatures, from about 84° C. to about 100° C.—for example, retaining over 20% of its untreated fluorescence when no fluorescence is retained by the ancestral protein after a 10-minute thermal challenge at 100° C.

Figure 7:
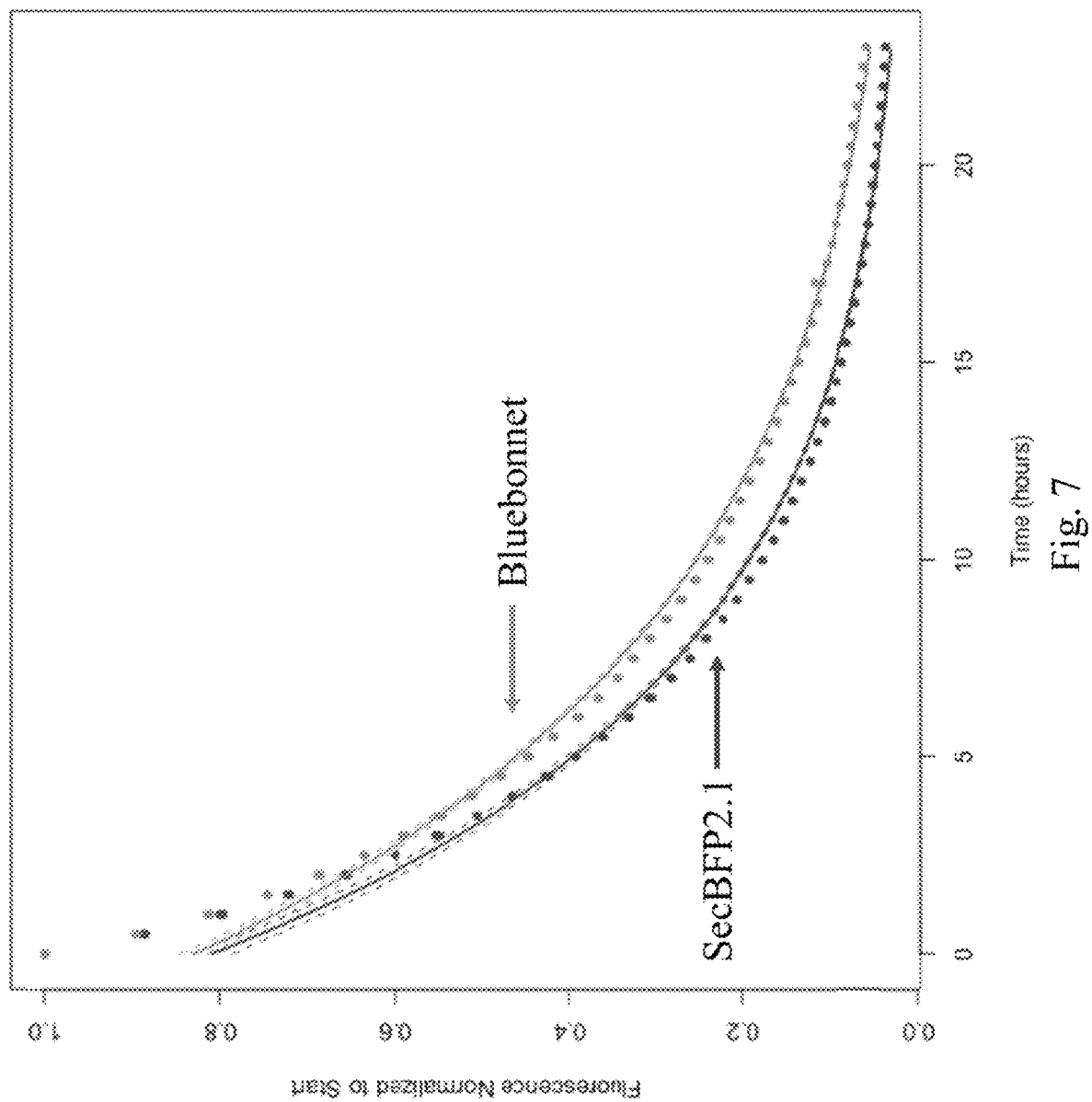

FIG. 7 shows that the neural network improved the chemical stability of a blue fluorescent protein. In another example, the fluorescence half-life in a guanidinium melt was less for the ancestral protein, SecBFP2.1, than for the derived protein, Bluebonnet. Purified blue fluorescent proteins were diluted to 0.01 mg/mL in 6 M guanidinium hydrochloride. 100 uL aliquots in triplicate were added to wells of a 96-well clear-bottom black-walled plate and incubated at 25° C. for 23 hours. These purified fluorescent proteins were assayed at 30 minute intervals using excitation and emission wavelengths of 402 nm and 457 nm, respectively. Plates were agitated preceding each measurement. Fluorescence values measured at time zero were used to normalize fluorescence through the remainder of the assay (e.g., a measurement of 0.8 indicates that the protein retained 80% of its initial fluorescence). As shown in FIG. 7, Bluebonnet exhibited greater chemical stability than SecBFP2.1 across all time points greater than time=0 up to about time=24 hours.

Example 2: Bluebonnet, a Brighter Blue Fluorescent Protein

Figure 8:
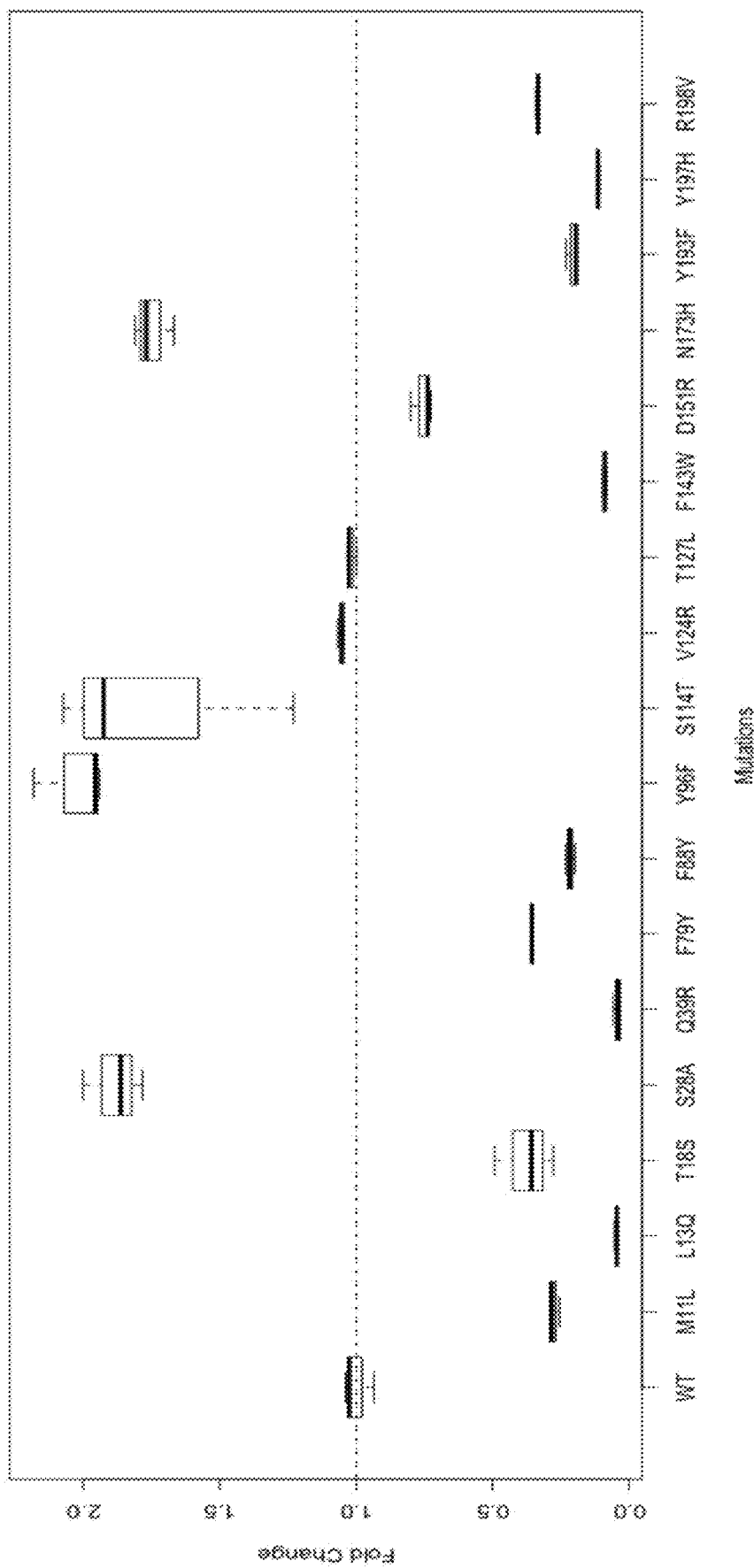
FIG. 8 is a graph demonstrating the fold change in fluorescence of seventeen blue fluorescent protein variants relative to the wild type protein.
Figure 9:
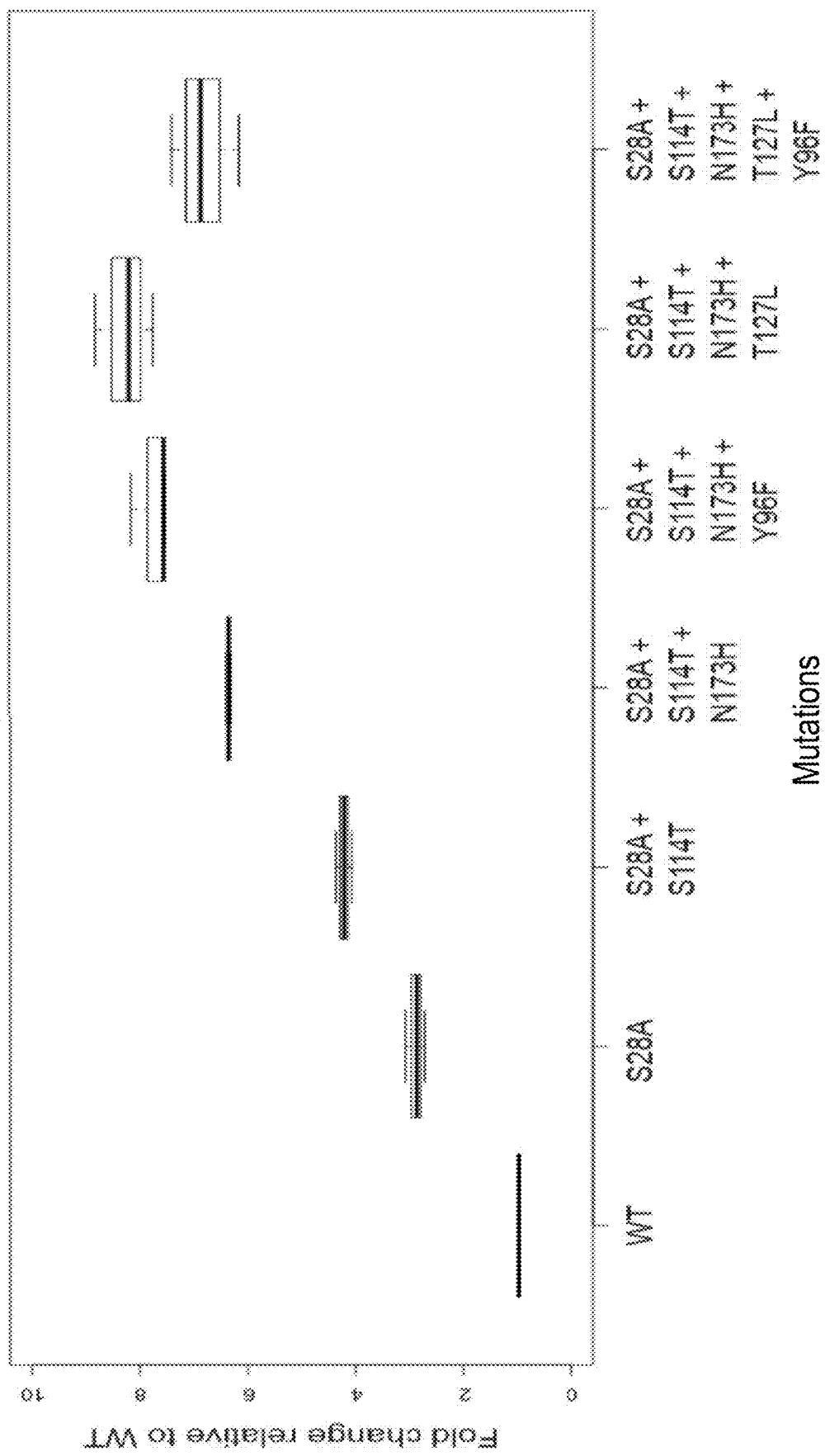
FIG. 9 is a graph demonstrating the fold change in fluorescence of blue fluorescent protein variants relative to the wild type protein.
Figure 10:
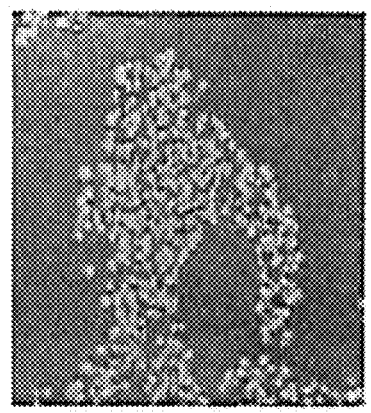
FIG. 10 provides exemplary images of the fluorescence of the blue fluorescent protein variant "bluebonnet," which comprises S28A, S114T, N173H and T127L mutations, as compared to the parental protein and other blue fluorescent proteins.
Figure 10:
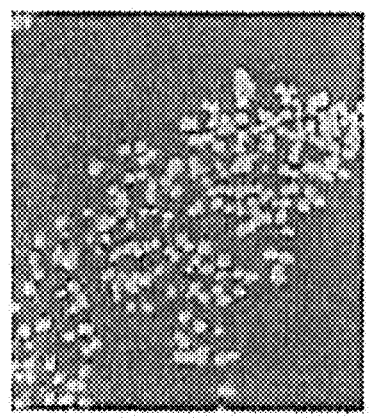
Figure 10:
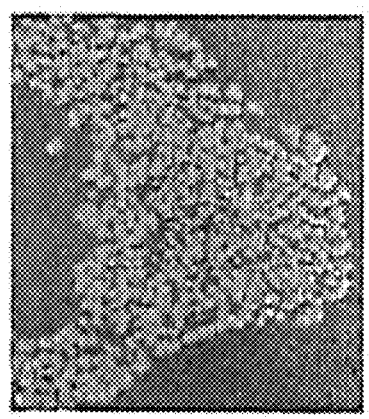
Figure 10:

When looking at how and where proteins move throughout a cell, scientists need specialized genetic tools. One of these tools is a family of proteins that fluoresce under UV light, i.e. fluorescent proteins. Blue fluorescent protein (BFP, pdb: 3m24) is a derivative of the much more commonly used red fluorescent protein but suffers from poor in vivo activity. The 3D convolutional neural network pipeline was used to predict variants of BFP that would result in increased fluorescence when expressed within E. coli cells. FIG. 8 provides data demonstrating that seventeen neural network predictions were tested for the ability to increase fluorescence (shown normalized to wild-type). FIG. 9 provides data demonstrating that when the beneficial mutations were combined, an increase of >8 fold fluorescence over wild-type was observed. FIG. 10 shows that the increase in fluorescence of the Bluebonnet blue fluorescent protein, which comprises the combination of S28A, S114T, T127L and N173H mutations, is visible when compared to the parental strain as well as other blue fluorescent proteins.

System Diagram of Computers

Figure 11A:
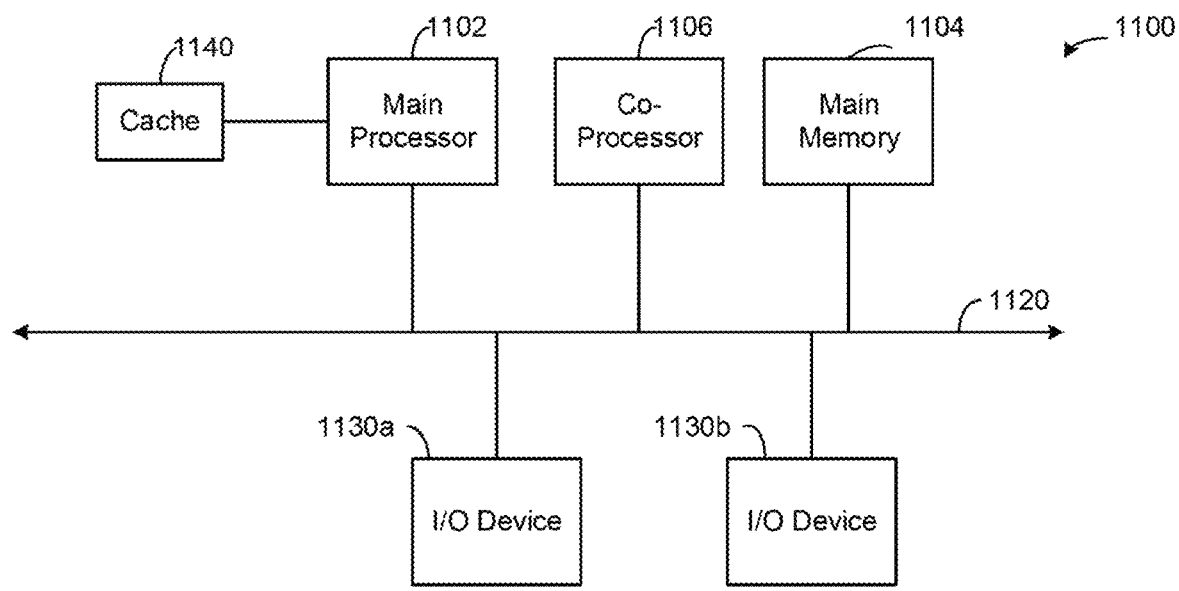
FIGS. 11A and 11B are block diagrams depicting implementations of systems for increasing synthesized protein characteristics.
Figure 11B:
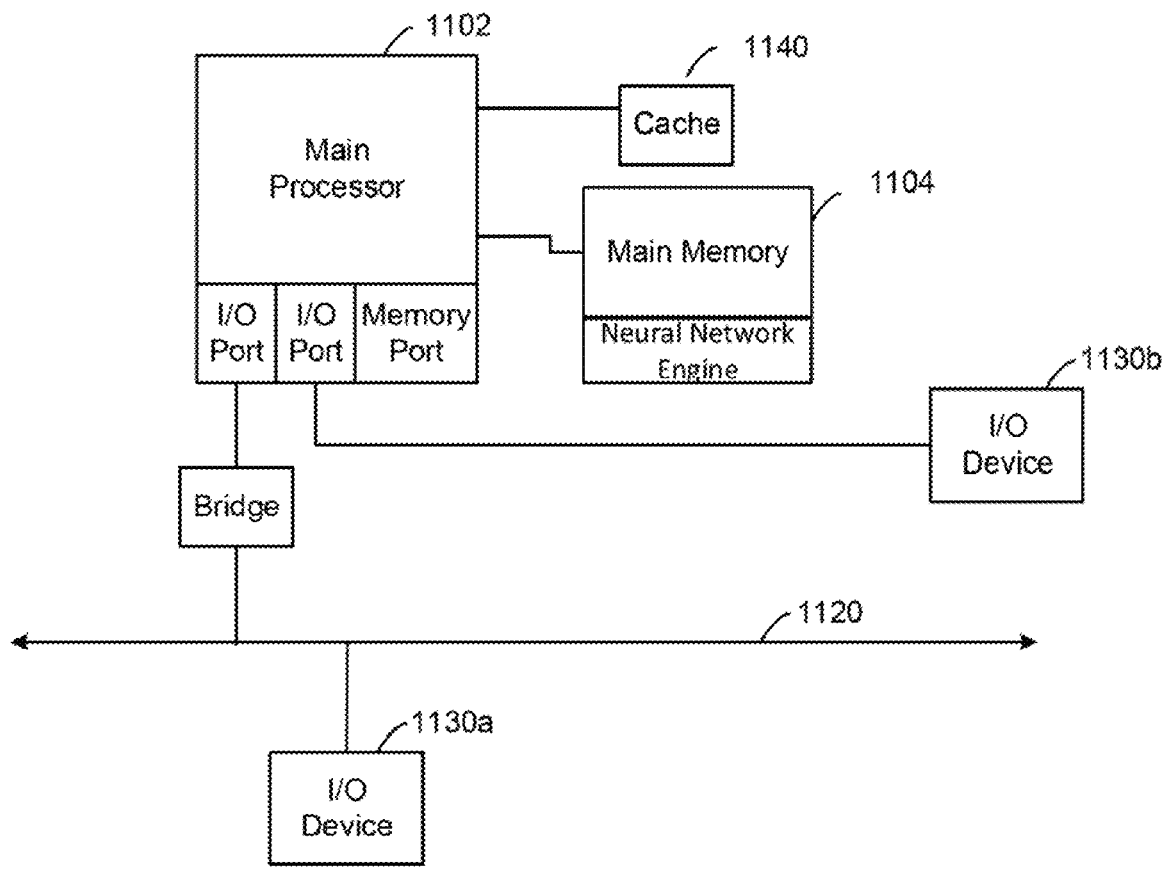

FIGS. 11A and 11B are block diagrams depicting embodiments of computers useful in connection with implementations of the systems and methods discussed herein. FIGS. 11A and 11B depict block diagrams of a typical computer 1100. As shown in FIGS. 11A and 11B, computer 1100 includes a central processing unit 1102 and a main memory unit 1104. Computer 1100 may also include other optional elements, such as one or more input/output devices 130a-130n (generally referred to using reference numeral 1130), a co-processor 1106, and a cache memory 1140 in communication with the central processing unit 1102 and co-processor 1106.

The central processing unit 1102 is any logic circuitry that responds to and processes instructions fetched from the main memory unit 1104. In many embodiments, the central processing unit is provided by a microprocessor unit, such as those manufactured by Intel Corporation of Mountain View, Calif.: those manufactured by Motorola Corporation of Schaumburg, Ill.; those manufactured by International Business Machines of White Plains, N.Y.; or those manufactured by Advanced Micro Devices of Sunnyvale, Calif.

Similarly, the co-processor 1106 is any logic circuitry that responds to and processes instructions fetched from the main memory unit 1104. In some embodiments, the co-processor 1106 may include a tensor processing unit ("TPU") which is an Artificial Intelligence application-specific integrated circuit, such as those manufactured by Google of Mountain View, Calif.

Main memory unit 1104 may be one or more memory chips capable of storing data and allowing any storage location to be directly accessed by a microprocessor in the main processor 1102 or the co-processor 1106, such as Static random access memory (SRAM), Burst SRAM or SynchBurst SRAM (BSRAM), Dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDEC SRAM, PC100 SDRAM, Double Data Rate SDRAM (DDR SDRAM), Enhanced SDRAM (ESDRAM), SyncLink DRAM (SLDRAM), Direct Rambus DRAM (DRDRAM), or Ferroelectric RAM (FRAM).

In the embodiment shown in FIG. 11A, the processor 1102 communicates with main memory 1104 via a system bus 1120 (described in more detail below). Similarly, the co-processor 1106 communicates with main memory 1104 via the system bus 1120. FIG. 11B depicts an embodiment of a computer system 1100 in which the processor 1102 communicates directly with main memory 1104 via a memory port. For example, in FIG. 11B, the main memory 1104 may be DRDRAM. In some embodiments, a neural network engine may reside within the main memory as the main memory may be responsible for storing the value of the trained weights.

FIGS. 11A and 11B depict embodiments in which the main processor 1102 communicates directly with cache memory 1140 via a secondary bus, sometimes referred to as a "backside" bus. In some embodiments, the co-processor 1106 may communicate directly with cache memory 1140 via the secondary bus. In other embodiments, the main processor 1102 communicates with cache memory 1140 using the system bus 1120. In other embodiments, the co-processor 1106 may communicate with cache memory 1140 using the system bus 1120. Cache memory 1140 typically has a faster response time than main memory 1104 and is typically provided by SRAM, BSRAM, or EDRAM. In some embodiments, the co-processor may comprise a tensor processing unit (TPU) or other co-processor, such an application-specific integrated circuit (ASIC) for performing calculations related to the neural network (which may be faster or more efficient than performing such calculations on the primary processor 1102).

In the embodiment shown in FIG. 11A, the processor 1102 and co-processor 1106 communicate with various I/O devices 1130 via a local system bus 1120. Various busses may be used to connect the central processing unit 1102 and co-processor 1106 to the I/O devices 1130, including a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display, the processor 1102 and/or co-processor 1106 may use an Advanced Graphics Port (AGP) to communicate with the display. FIG. 11B depicts an embodiment of a computer system 1100 in which the main processor 1102 communicates directly with I/O device 1130b via HyperTransport, Rapid I/O, or InfiniBand. FIG.

11B also depicts an embodiment in which local busses and direct communication are mixed: the processor 1102 communicates with I/O device 1130*a* using a local interconnect bus while communicating with I/O device 1130*b* directly.

A wide variety of I/O devices 1130 may be present in the computer system 1100. Input devices include keyboards, mice, trackpads, trackballs, microphones, and drawing tablets. Output devices include video displays, speakers, inkjet printers, laser printers, and dye-sublimation printers. An I/O device may also provide mass storage for the computer system 1100 such as a hard disk drive, a floppy disk drive for receiving floppy disks such as 3.5-inch, 5.25-inch disks or ZIP disks, a CD-ROM drive, a CD-R/RW drive, a DVD-ROM drive, tape drives of various formats, and USB storage devices such as the USB Flash Drive line of devices manufactured by Twintech Industry, Inc. of Los Alamitos, Calif., and the iPod Shuffle line of devices manufactured by Apple Computer, Inc., of Cupertino, Calif.

In further embodiments, an I/O device 1130 may be a bridge between the system bus 1120 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a HIPPI bus, a Super HIPPI bus, a SerialPlus bus, a SCI/LAMP bus, a FibreChannel bus, or a Serial Attached small computer system interface bus.

General-purpose desktop computers of the sort depicted in FIGS. 11A and 11B typically operate under the control of operating systems, which control scheduling of tasks and access to system resources. Typical operating systems include: MICROSOFT WINDOWS, manufactured by Microsoft Corp. of Redmond, Wash.; MacOS, manufactured by Apple Computer of Cupertino, Calif.; OS/2, manufactured by International Business Machines of Armonk, N.Y.; and Linux, a freely-available operating system distributed by Caldera Corp. of Salt Lake City, Utah, among others.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A computer-implemented method of training a neural network to improve a characteristic of a protein, comprising:
    collecting a set of amino acid sequences from a database;
    compiling a set of three-dimensional crystallographic structures having chemical environments for the set of amino acids;
    translating the three-dimensional crystallographic structures into voxelized matrices;
    training a neural network with a subset of the voxelized matrices;
    identifying, with the neural network, a candidate residue to mutate in a target protein; and
    identifying, with the neural network, a predicted amino acid residue to substitute for the candidate residue, to produce a mutated protein;
    wherein the mutated protein includes a novel stabilizing mutation and demonstrates an improvement in a characteristic over the target protein.

2. The computer-implemented method of claim 1, further comprising adding a spatial arrangement of a feature selected from the group consisting of hydrogen location, partial charges, beta factors, secondary structure, aromaticity, electron density and polarity to at least one of the three-dimensional crystallographic structures.

3. The computer-implemented method of claim 1, further comprising adjusting the set of amino acid sequences to reflect their natural frequencies.

4. The computer-implemented method of claim 1, further comprising sampling at least 50% of the amino acids in the set of amino acid sequences from a random location in the sequence.

5. The computer-implemented method of claim 1, further comprising training a second independent neural network with a second subset of three-dimensional crystallographic structures, and identifying the candidate and predicted amino acid residues based on the results of both neural networks.

6. The method of claim 1, wherein the characteristic is stability, maturation, or folding.

7. A system for improving a characteristic of a protein, comprising a processor and a non-transitory computer-readable medium with instructions stored thereon, that when executed by the processor perform steps comprising:
    providing a target protein comprising a sequence of amino acids;
    providing a set of three-dimensional models surrounding an amino acid and a set of protein characteristic values for each three dimensional model;
    estimating a set of parameters at various points in each three dimensional model;
    training a neural network with the three dimensional models, the parameters, and the protein characteristic values;
    identifying, with the neural network, a candidate residue to mutate in the target protein; and
    identifying, with the neural network, a predicted amino acid residue to substitute for the candidate residue, producing a mutated protein;
    wherein the mutated protein includes a novel stabilizing mutation and demonstrates an improvement in the characteristic over the target protein.

8. The system of claim 7, wherein the protein characteristic is stability.

9. The system of claim 7, wherein the steps include recompiling at least one amino acid sequence to produce an updated three-dimensional model.

10. The system of claim 9, wherein the steps include adding a spatial arrangement of a feature to at least one amino acid sequence before recompilation.

11. The method of claim 1, wherein translating the three-dimensional crystallographic structure into voxelized matrices comprises mapping coordinates associated with the three-dimensional crystallographic structure into a three-dimensional array.

12. The method of claim 1, wherein the subset of voxelized matrices comprises matrices of a training data set built from proteins that are phylogenetically divergent over a threshold.

13. The method of claim 1, wherein the subset of voxelized matrices comprises matrices of a training data set built from proteins with added hydrogen atoms to protein structures.

14. The method of claim 1, wherein the subset of voxelized matrices comprises matrices of a training set built from proteins with added biophysical channels.

15. The method of claim 1, further comprising:
    removing from the subset of voxelized matrices, proteins satisfying a high-resolution threshold, wherein the high-resolution threshold indicates that an electron density map based on the three-dimensional crystallographic structure is resolvable to a threshold distance between points of the electron density map.

16. The method of claim 1, further comprising:
    creating a frame of reference around a central amino acid; and
    extracting features around the central amino acid.

17. A system for improving a characteristic of a protein, comprising a processor and a non-transitory computer-readable medium with instructions stored thereon, that when executed by the processor perform steps comprising:
    collecting a set of amino acid sequences from a database;
    compiling a set of three-dimensional crystallographic structures having chemical environments for the set of amino acids;
    translating the three-dimensional crystallographic structures into voxelized matrices;
    training a neural network with a subset of the voxelized matrices;
    identifying, with the neural network, a candidate residue to mutate in a target protein; and
    identifying, with the neural network, a predicted amino acid residue to substitute for the candidate residue, to produce a mutated protein;
    wherein the mutated protein includes a novel stabilizing mutation and demonstrates an improvement in a characteristic over the target protein.

18. The system of claim 17, wherein the subset of voxelized matrices comprises matrices of a training data set built from proteins that are phylogenetically divergent over a threshold.

19. The system of claim 17, wherein the subset of voxelized matrices comprises matrices of a training data set built from proteins with added hydrogen atoms to protein structures.

20. The system of claim 17, wherein the subset of voxelized matrices comprises matrices of a training set built from proteins with added biophysical channels.

21. The method of claim 1, wherein the mutated protein comprises a phosphomannose isomerase and the novel stabilizing mutation is selected from the group consisting of D229W, N272K, C295V, S368P, L335A, N388S, S425T and combinations thereof.

22. The system of claim 7, wherein the mutated protein comprises a phosphomannose isomerase and the novel stabilizing mutation is selected from the group consisting of D229W, N272K, C295V, S368P, L335A, N388S, S425T and combinations thereof.

23. The system of claim 17, wherein the mutated protein comprises a phosphomannose isomerase and the novel stabilizing mutation is selected from the group consisting of D229W, N272K, C295V, S368P, L335A, N388S, S425T and combinations thereof.

24. The method of claim 1, wherein the mutated protein comprises a blue fluorescent protein and the novel stabilizing mutation is selected from the group consisting of S28A, Y96F, S114T, V124R, T127L, N173H and combinations thereof.

25. The system of claim 7, wherein the mutated protein comprises a blue fluorescent protein and the novel stabilizing mutation is selected from the group consisting of S28A, Y96F, S114T, V124R, T127L, N173H and combinations thereof.

26. The system of claim 17, wherein the mutated protein comprises a blue fluorescent protein and the novel stabilizing mutation is selected from the group consisting of S28A, Y96F, S114T, V124R, T127L, N173H and combinations thereof.

* * * * *

```
                          SEQUENCE LISTING

<160> NUMBER OF SEQ ID NOS: 28

<210> SEQ ID NO 1
<211> LENGTH: 233
<212> TYPE: PRT
<213> ORGANISM: Artificial Sequence
<220> FEATURE:
<223> OTHER INFORMATION: Wild-type secBFP2

<400> SEQUENCE: 1

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
                20                  25                  30

Lys Pro Tyr Glu Gly Thr Gln Thr Met Arg Ile Lys Val Val Glu Gly
            35                  40                  45

Gly Pro Leu Pro Phe Ala Phe Asp Ile Leu Ala Thr Ser Phe Leu Tyr
        50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
                100                 105                 110

Gly Ser Leu Ile Tyr Asn Val Lys Ile Arg Gly Val Asp Phe Thr Ser
            115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
                180                 185                 190

Tyr Tyr Val Asp Tyr Arg Leu Glu Arg Ile Lys Glu Ala Asn Asp Glu
```

```
            195                 200                 205
Thr Tyr Val Glu Gln His Glu Val Ala Val Ala Arg Tyr Ser Asp Leu
    210                 215                 220

Pro Ser Lys Leu Gly His Lys Leu Asn
225                 230

<210> SEQ ID NO 2
<211> LENGTH: 233
<212> TYPE: PRT
<213> ORGANISM: Artificial Sequence
<220> FEATURE:
<223> OTHER INFORMATION: secBFP2 comprising a T18W mutation

<400> SEQUENCE: 2

Ser Glu Glu Leu Ile Lys Glu Asn Met His Met Lys Leu Tyr Met Glu
1               5                   10                  15

Gly Trp Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Ser Leu Ile Tyr Asn Val Lys Ile Arg Gly Val Asp Phe Thr Ser
        115                 120                 125

Asn Gly Pro Val Met Gln Lys Lys Thr Leu Gly Trp Glu Ala Phe Thr
130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
        195                 200                 205

Thr Tyr Val Glu Gln His Glu Val Ala Val Ala Arg Tyr Ser Asp Leu
    210                 215                 220

Pro Ser Lys Leu Gly His Lys Leu Asn
225                 230

<210> SEQ ID NO 3
<211> LENGTH: 233
<212> TYPE: PRT
<213> ORGANISM: Artificial Sequence
<220> FEATURE:
<223> OTHER INFORMATION: secBFP2 comprising a T18V mutation

<400> SEQUENCE: 3

Ser Glu Glu Leu Ile Lys Glu Asn Met His Met Lys Leu Tyr Met Glu
1               5                   10                  15

Gly Val Val Asp Asn His His Phe Lys Cys Thr Ser Glu Gly Glu Gly
            20                  25                  30
```

-continued

```
Lys Pro Tyr Glu Gly Thr Gln Thr Met Arg Ile Lys Val Val Glu Gly
             35                  40                  45

Gly Pro Leu Pro Phe Ala Phe Asp Ile Leu Ala Thr Ser Phe Leu Tyr
 50                  55                  60

Gly Ser Lys Thr Phe Ile Asp His Thr Gln Gly Ile Pro Asp Phe Phe
 65                  70                  75                  80

Lys Gln Ser Phe Pro Glu Gly Phe Thr Trp Glu Arg Val Thr Thr Tyr
                 85                  90                  95

Glu Asp Gly Gly Val Leu Thr Ala Gln Asp Thr Ser Leu Gln Asp
                100                 105                 110

Gly Ser Leu Ile Tyr Asn Val Lys Ile Arg Gly Val Asp Phe Thr Ser
                115                 120                 125

Asn Gly Pro Val Met Gln Lys Lys Thr Leu Gly Trp Glu Ala Phe Thr
130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
                180                 185                 190

Tyr Tyr Val Asp Tyr Arg Leu Glu Arg Ile Lys Glu Ala Asn Asp Glu
                195                 200                 205

Thr Tyr Val Glu Gln His Glu Val Ala Val Ala Arg Tyr Ser Asp Leu
                210                 215                 220

Pro Ser Lys Leu Gly His Lys Leu Asn
225                 230

<210> SEQ ID NO 4
<211> LENGTH: 233
<212> TYPE: PRT
<213> ORGANISM: Artificial Sequence
<220> FEATURE:
<223> OTHER INFORMATION: secBFP2 comprising a T18E mutation

<400> SEQUENCE: 4

Ser Glu Glu Leu Ile Lys Glu Asn Met His Met Lys Leu Tyr Met Glu
 1               5                  10                  15

Gly Glu Val Asp Asn His His Phe Lys Cys Thr Ser Glu Gly Glu Gly
                 20                  25                  30

Lys Pro Tyr Glu Gly Thr Gln Thr Met Arg Ile Lys Val Val Glu Gly
             35                  40                  45

Gly Pro Leu Pro Phe Ala Phe Asp Ile Leu Ala Thr Ser Phe Leu Tyr
 50                  55                  60

Gly Ser Lys Thr Phe Ile Asp His Thr Gln Gly Ile Pro Asp Phe Phe
 65                  70                  75                  80

Lys Gln Ser Phe Pro Glu Gly Phe Thr Trp Glu Arg Val Thr Thr Tyr
                 85                  90                  95

Glu Asp Gly Gly Val Leu Thr Ala Gln Asp Thr Ser Leu Gln Asp
                100                 105                 110

Gly Ser Leu Ile Tyr Asn Val Lys Ile Arg Gly Val Asp Phe Thr Ser
                115                 120                 125

Asn Gly Pro Val Met Gln Lys Lys Thr Leu Gly Trp Glu Ala Phe Thr
130                 135                 140

Glu Thr Leu Tyr Pro Ala Asp Gly Gly Leu Glu Gly Arg Asn Asp Met
145                 150                 155                 160
```

Ala Leu Lys Leu Val Gly Gly Ser His Leu Ile Ala Asn Ala Lys Thr
            165                 170                 175

Thr Tyr Arg Ser Lys Lys Pro Ala Lys Asn Leu Lys Met Pro Gly Val
        180                 185                 190

Tyr Tyr Val Asp Tyr Arg Leu Glu Arg Ile Lys Glu Ala Asn Asp Glu
            195                 200                 205

Thr Tyr Val Glu Gln His Glu Val Ala Val Ala Arg Tyr Ser Asp Leu
        210                 215                 220

Pro Ser Lys Leu Gly His Lys Leu Asn
225                 230

<210> SEQ ID NO 5
<211> LENGTH: 233
<212> TYPE: PRT
<213> ORGANISM: Artificial Sequence
<220> FEATURE:
<223> OTHER INFORMATION: secBFP2 comprising a S28A mutation

<400> SEQUENCE: 5

Ser Glu Glu Leu Ile Lys Glu Asn Met His Met Lys Leu Tyr Met Glu
1               5                   10                  15

Gly Thr Val Asp Asn His His Phe Lys Cys Thr Ala Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Ser Leu Ile Tyr Asn Val Lys Ile Arg Gly Val Asp Phe Thr Ser
        115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
            165                 170                 175

Thr Tyr Arg Ser Lys Lys Pro Ala Lys Asn Leu Lys Met Pro Gly Val
        180                 185                 190

Tyr Tyr Val Asp Tyr Arg Leu Glu Arg Ile Lys Glu Ala Asn Asp Glu
            195                 200                 205

Thr Tyr Val Glu Gln His Glu Val Ala Val Ala Arg Tyr Ser Asp Leu
        210                 215                 220

Pro Ser Lys Leu Gly His Lys Leu Asn
225                 230

<210> SEQ ID NO 6
<211> LENGTH: 233
<212> TYPE: PRT
<213> ORGANISM: Artificial Sequence
<220> FEATURE:
<223> OTHER INFORMATION: secBFP2 comprising a Y96F mutation

<400> SEQUENCE: 6

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
                20                  25                  30

Lys Pro Tyr Glu Gly Thr Gln Thr Met Arg Ile Lys Val Val Glu Gly
            35                  40                  45

Gly Pro Leu Pro Phe Ala Phe Asp Ile Leu Ala Thr Ser Phe Leu Tyr
        50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Phe
                85                  90                  95

Glu Asp Gly Gly Val Leu Thr Ala Thr Gln Asp Thr Ser Leu Gln Asp
            100                 105                 110

Gly Ser Leu Ile Tyr Asn Val Lys Ile Arg Gly Val Asp Phe Thr Ser
        115                 120                 125

Asn Gly Pro Val Met Gln Lys Lys Thr Leu Gly Trp Glu Ala Phe Thr
130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
        195                 200                 205

Thr Tyr Val Glu Gln His Glu Val Ala Val Ala Arg Tyr Ser Asp Leu
210                 215                 220

Pro Ser Lys Leu Gly His Lys Leu Asn
225                 230

<210> SEQ ID NO 7
<211> LENGTH: 233
<212> TYPE: PRT
<213> ORGANISM: Artificial Sequence
<220> FEATURE:
<223> OTHER INFORMATION: secBFP2 comprising a S114V mutation

<400> SEQUENCE: 7

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
                20                  25                  30

Lys Pro Tyr Glu Gly Thr Gln Thr Met Arg Ile Lys Val Val Glu Gly
            35                  40                  45

Gly Pro Leu Pro Phe Ala Phe Asp Ile Leu Ala Thr Ser Phe Leu Tyr
        50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Val Leu Ile Tyr Asn Val Lys Ile Arg Gly Val Asp Phe Thr Ser
        115                 120                 125

Asn Gly Pro Val Met Gln Lys Lys Thr Leu Gly Trp Glu Ala Phe Thr
            130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
        195                 200                 205

Thr Tyr Val Glu Gln His Glu Val Ala Val Ala Arg Tyr Ser Asp Leu
    210                 215                 220

Pro Ser Lys Leu Gly His Lys Leu Asn
225                 230

<210> SEQ ID NO 8
<211> LENGTH: 233
<212> TYPE: PRT
<213> ORGANISM: Artificial Sequence
<220> FEATURE:
<223> OTHER INFORMATION: secBFP2 comprising a S114T mutation

<400> SEQUENCE: 8

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Thr Leu Ile Tyr Asn Val Lys Ile Arg Gly Val Asp Phe Thr Ser
        115                 120                 125

Asn Gly Pro Val Met Gln Lys Lys Thr Leu Gly Trp Glu Ala Phe Thr
            130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
        195                 200                 205

Thr Tyr Val Glu Gln His Glu Val Ala Val Ala Arg Tyr Ser Asp Leu
    210                 215                 220

Pro Ser Lys Leu Gly His Lys Leu Asn
225                 230

<210> SEQ ID NO 9

```
<211> LENGTH: 233
<212> TYPE: PRT
<213> ORGANISM: Artificial Sequence
<220> FEATURE:
<223> OTHER INFORMATION: secBFP2 comprising a V124T mutation

<400> SEQUENCE: 9

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Ser Leu Ile Tyr Asn Val Lys Ile Arg Gly Thr Asp Phe Thr Ser
        115                 120                 125

Asn Gly Pro Val Met Gln Lys Lys Thr Leu Gly Trp Glu Ala Phe Thr
130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
        195                 200                 205

Thr Tyr Val Glu Gln His Glu Val Ala Val Ala Arg Tyr Ser Asp Leu
210                 215                 220

Pro Ser Lys Leu Gly His Lys Leu Asn
225                 230

<210> SEQ ID NO 10
<211> LENGTH: 233
<212> TYPE: PRT
<213> ORGANISM: Artificial Sequence
<220> FEATURE:
<223> OTHER INFORMATION: secBFP2 comprising a V124Y mutation

<400> SEQUENCE: 10

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
```

```
                        85                  90                  95
Glu Asp Gly Gly Val Leu Thr Ala Thr Gln Asp Thr Ser Leu Gln Asp
                100                 105                 110

Gly Ser Leu Ile Tyr Asn Val Lys Ile Arg Gly Tyr Asp Phe Thr Ser
            115                 120                 125

Asn Gly Pro Val Met Gln Lys Thr Leu Gly Trp Glu Ala Phe Thr
        130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
                180                 185                 190

Tyr Tyr Val Asp Tyr Arg Leu Glu Arg Ile Lys Glu Ala Asn Asp Glu
                195                 200                 205

Thr Tyr Val Glu Gln His Glu Val Ala Val Ala Arg Tyr Ser Asp Leu
                210                 215                 220

Pro Ser Lys Leu Gly His Lys Leu Asn
225                 230
```

<210> SEQ ID NO 11
<211> LENGTH: 233
<212> TYPE: PRT
<213> ORGANISM: Artificial Sequence
<220> FEATURE:
<223> OTHER INFORMATION: secBFP2 comprising a V124W mutation

<400> SEQUENCE: 11

```
Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
                20                  25                  30

Lys Pro Tyr Glu Gly Thr Gln Thr Met Arg Ile Lys Val Val Glu Gly
            35                  40                  45

Gly Pro Leu Pro Phe Ala Phe Asp Ile Leu Ala Thr Ser Phe Leu Tyr
50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
                100                 105                 110

Gly Ser Leu Ile Tyr Asn Val Lys Ile Arg Gly Trp Asp Phe Thr Ser
            115                 120                 125

Asn Gly Pro Val Met Gln Lys Thr Leu Gly Trp Glu Ala Phe Thr
        130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
                180                 185                 190

Tyr Tyr Val Asp Tyr Arg Leu Glu Arg Ile Lys Glu Ala Asn Asp Glu
                195                 200                 205

Thr Tyr Val Glu Gln His Glu Val Ala Val Ala Arg Tyr Ser Asp Leu
```

Pro Ser Lys Leu Gly His Lys Leu Asn
225                 230

<210> SEQ ID NO 12
<211> LENGTH: 233
<212> TYPE: PRT
<213> ORGANISM: Artificial Sequence
<220> FEATURE:
<223> OTHER INFORMATION: secBFP2 comprising a T127P mutation

<400> SEQUENCE: 12

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Ser Leu Ile Tyr Asn Val Lys Ile Arg Gly Val Asp Phe Pro Ser
        115                 120                 125

Asn Gly Pro Val Met Gln Lys Lys Thr Leu Gly Trp Glu Ala Phe Thr
130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
        195                 200                 205

Thr Tyr Val Glu Gln His Glu Val Ala Val Ala Arg Tyr Ser Asp Leu
210                 215                 220

Pro Ser Lys Leu Gly His Lys Leu Asn
225                 230

<210> SEQ ID NO 13
<211> LENGTH: 233
<212> TYPE: PRT
<213> ORGANISM: Artificial Sequence
<220> FEATURE:
<223> OTHER INFORMATION: secBFP2 comprising a T127L mutation

<400> SEQUENCE: 13

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

```
Gly Pro Leu Pro Phe Ala Phe Asp Ile Leu Ala Thr Ser Phe Leu Tyr
        50                  55                  60
Gly Ser Lys Thr Phe Ile Asp His Thr Gln Gly Ile Pro Asp Phe Phe
 65                  70                  75                  80
Lys Gln Ser Phe Pro Glu Gly Phe Thr Trp Glu Arg Val Thr Thr Tyr
                 85                  90                  95
Glu Asp Gly Gly Val Leu Thr Ala Thr Gln Asp Thr Ser Leu Gln Asp
            100                 105                 110
Gly Ser Leu Ile Tyr Asn Val Lys Ile Arg Gly Val Asp Phe Leu Ser
        115                 120                 125
Asn Gly Pro Val Met Gln Lys Lys Thr Leu Gly Trp Glu Ala Phe Thr
130                 135                 140
Glu Thr Leu Tyr Pro Ala Asp Gly Gly Leu Glu Gly Arg Asn Asp Met
145                 150                 155                 160
Ala Leu Lys Leu Val Gly Gly Ser His Leu Ile Ala Asn Ala Lys Thr
                165                 170                 175
Thr Tyr Arg Ser Lys Lys Pro Ala Lys Asn Leu Lys Met Pro Gly Val
            180                 185                 190
Tyr Tyr Val Asp Tyr Arg Leu Glu Arg Ile Lys Glu Ala Asn Asp Glu
        195                 200                 205
Thr Tyr Val Glu Gln His Glu Val Ala Val Ala Arg Tyr Ser Asp Leu
    210                 215                 220
Pro Ser Lys Leu Gly His Lys Leu Asn
225                 230

<210> SEQ ID NO 14
<211> LENGTH: 233
<212> TYPE: PRT
<213> ORGANISM: Artificial Sequence
<220> FEATURE:
<223> OTHER INFORMATION: secBFP2 comprising a T127R mutation

<400> SEQUENCE: 14

Ser Glu Glu Leu Ile Lys Glu Asn Met His Met Lys Leu Tyr Met Glu
 1               5                  10                  15
Gly Thr Val Asp Asn His His Phe Lys Cys Thr Ser Glu Gly Glu Gly
             20                  25                  30
Lys Pro Tyr Glu Gly Thr Gln Thr Met Arg Ile Lys Val Val Glu Gly
         35                  40                  45
Gly Pro Leu Pro Phe Ala Phe Asp Ile Leu Ala Thr Ser Phe Leu Tyr
     50                  55                  60
Gly Ser Lys Thr Phe Ile Asp His Thr Gln Gly Ile Pro Asp Phe Phe
 65                  70                  75                  80
Lys Gln Ser Phe Pro Glu Gly Phe Thr Trp Glu Arg Val Thr Thr Tyr
                 85                  90                  95
Glu Asp Gly Gly Val Leu Thr Ala Thr Gln Asp Thr Ser Leu Gln Asp
            100                 105                 110
Gly Ser Leu Ile Tyr Asn Val Lys Ile Arg Gly Val Asp Phe Arg Ser
        115                 120                 125
Asn Gly Pro Val Met Gln Lys Lys Thr Leu Gly Trp Glu Ala Phe Thr
130                 135                 140
Glu Thr Leu Tyr Pro Ala Asp Gly Gly Leu Glu Gly Arg Asn Asp Met
145                 150                 155                 160
Ala Leu Lys Leu Val Gly Gly Ser His Leu Ile Ala Asn Ala Lys Thr
                165                 170                 175
```

```
Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
        195                 200                 205

Thr Tyr Val Glu Gln His Glu Val Ala Val Ala Arg Tyr Ser Asp Leu
        210                 215                 220

Pro Ser Lys Leu Gly His Lys Leu Asn
225                 230

<210> SEQ ID NO 15
<211> LENGTH: 233
<212> TYPE: PRT
<213> ORGANISM: Artificial Sequence
<220> FEATURE:
<223> OTHER INFORMATION: secBFP2 comprising a T127D mutation

<400> SEQUENCE: 15

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Ser Leu Ile Tyr Asn Val Lys Ile Arg Gly Val Asp Phe Asp Ser
        115                 120                 125

Asn Gly Pro Val Met Gln Lys Lys Thr Leu Gly Trp Glu Ala Phe Thr
130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
        195                 200                 205

Thr Tyr Val Glu Gln His Glu Val Ala Val Ala Arg Tyr Ser Asp Leu
        210                 215                 220

Pro Ser Lys Leu Gly His Lys Leu Asn
225                 230

<210> SEQ ID NO 16
<211> LENGTH: 233
<212> TYPE: PRT
<213> ORGANISM: Artificial Sequence
<220> FEATURE:
<223> OTHER INFORMATION: secBFP2 comprising a D151G mutation

<400> SEQUENCE: 16

Ser Glu Glu Leu Ile Lys Glu Asn Met His Met Lys Leu Tyr Met Glu
1               5                   10                  15
```

```
Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Ser Leu Ile Tyr Asn Val Lys Ile Arg Gly Val Asp Phe Thr Ser
        115                 120                 125

Asn Gly Pro Val Met Gln Lys Lys Thr Leu Gly Trp Glu Ala Phe Thr
130                 135                 140

Glu Thr Leu Tyr Pro Ala Gly Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
        180                 185                 190

Tyr Tyr Val Asp Tyr Arg Leu Glu Arg Ile Lys Glu Ala Asn Asp Glu
    195                 200                 205

Thr Tyr Val Glu Gln His Glu Val Ala Val Ala Arg Tyr Ser Asp Leu
210                 215                 220

Pro Ser Lys Leu Gly His Lys Leu Asn
225                 230

<210> SEQ ID NO 17
<211> LENGTH: 233
<212> TYPE: PRT
<213> ORGANISM: Artificial Sequence
<220> FEATURE:
<223> OTHER INFORMATION: secBFP2 comprising a N173T mutation

<400> SEQUENCE: 17

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Ser Leu Ile Tyr Asn Val Lys Ile Arg Gly Val Asp Phe Thr Ser
        115                 120                 125

Asn Gly Pro Val Met Gln Lys Lys Thr Leu Gly Trp Glu Ala Phe Thr
130                 135                 140
```

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Thr Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
        195                 200                 205

Thr Tyr Val Glu Gln His Glu Val Ala Val Ala Arg Tyr Ser Asp Leu
210                 215                 220

Pro Ser Lys Leu Gly His Lys Leu Asn
225                 230

<210> SEQ ID NO 18
<211> LENGTH: 233
<212> TYPE: PRT
<213> ORGANISM: Artificial Sequence
<220> FEATURE:
<223> OTHER INFORMATION: secBFP2 comprising a N173H mutation

<400> SEQUENCE: 18

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Ser Leu Ile Tyr Asn Val Lys Ile Arg Gly Val Asp Phe Thr Ser
        115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala His Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
        195                 200                 205

Thr Tyr Val Glu Gln His Glu Val Ala Val Ala Arg Tyr Ser Asp Leu
210                 215                 220

Pro Ser Lys Leu Gly His Lys Leu Asn
225                 230

<210> SEQ ID NO 19
<211> LENGTH: 233
<212> TYPE: PRT
<213> ORGANISM: Artificial Sequence
<220> FEATURE:
<223> OTHER INFORMATION: secBFP2 comprising a N173R mutation

<400> SEQUENCE: 19

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Ser Leu Ile Tyr Asn Val Lys Ile Arg Gly Val Asp Phe Thr Ser
        115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Arg Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
        195                 200                 205

Thr Tyr Val Glu Gln His Glu Val Ala Val Ala Arg Tyr Ser Asp Leu
    210                 215                 220

Pro Ser Lys Leu Gly His Lys Leu Asn
225                 230

<210> SEQ ID NO 20
<211> LENGTH: 233
<212> TYPE: PRT
<213> ORGANISM: Artificial Sequence
<220> FEATURE:
<223> OTHER INFORMATION: secBFP2 comprising a N173S mutation

<400> SEQUENCE: 20

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp

```
                    100                 105                 110
Gly Ser Leu Ile Tyr Asn Val Lys Ile Arg Gly Val Asp Phe Thr Ser
            115                 120                 125

Asn Gly Pro Val Met Gln Lys Lys Thr Leu Gly Trp Glu Ala Phe Thr
        130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Ser Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
        195                 200                 205

Thr Tyr Val Glu Gln His Glu Val Ala Val Ala Arg Tyr Ser Asp Leu
    210                 215                 220

Pro Ser Lys Leu Gly His Lys Leu Asn
225                 230

<210> SEQ ID NO 21
<211> LENGTH: 233
<212> TYPE: PRT
<213> ORGANISM: Artificial Sequence
<220> FEATURE:
<223> OTHER INFORMATION: secBFP2 comprising a R198V mutation

<400> SEQUENCE: 21

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Ser Leu Ile Tyr Asn Val Lys Ile Arg Gly Val Asp Phe Thr Ser
        115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Val Leu Glu Arg Ile Lys Glu Ala Asn Asp Glu
        195                 200                 205

Thr Tyr Val Glu Gln His Glu Val Ala Val Ala Arg Tyr Ser Asp Leu
    210                 215                 220

Pro Ser Lys Leu Gly His Lys Leu Asn
225                 230
```

<210> SEQ ID NO 22
<211> LENGTH: 233
<212> TYPE: PRT
<213> ORGANISM: Artificial Sequence
<220> FEATURE:
<223> OTHER INFORMATION: secBFP2 comprising a R198L mutation

<400> SEQUENCE: 22

Ser Glu Glu Leu Ile Lys Glu Asn Met His Met Lys Leu Tyr Met Glu
1               5                   10                  15

Gly Thr Val Asp Asn His His Phe Lys Cys Thr Ser Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Ser Leu Ile Tyr Asn Val Lys Ile Arg Gly Val Asp Phe Thr Ser
        115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Leu Leu Glu Arg Ile Lys Glu Ala Asn Asp Glu
        195                 200                 205

Thr Tyr Val Glu Gln His Glu Val Ala Val Ala Arg Tyr Ser Asp Leu
    210                 215                 220

Pro Ser Lys Leu Gly His Lys Leu Asn
225                 230

<210> SEQ ID NO 23
<211> LENGTH: 233
<212> TYPE: PRT
<213> ORGANISM: Artificial Sequence
<220> FEATURE:
<223> OTHER INFORMATION: secBFP2 comprising the mutations of T18W, S28A,
      S114V, V124T, T127P, D151G, N173T, and R198L

<400> SEQUENCE: 23

Ser Glu Glu Leu Ile Lys Glu Asn Met His Met Lys Leu Tyr Met Glu
1               5                   10                  15

Gly Trp Val Asp Asn His His Phe Lys Cys Thr Ala Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Val Leu Ile Tyr Asn Val Lys Ile Arg Gly Thr Asp Phe Pro Ser
            115                 120                 125

Asn Gly Pro Val Met Gln Lys Lys Thr Leu Gly Trp Glu Ala Phe Thr
130                 135                 140

Glu Thr Leu Tyr Pro Ala Gly Gly Leu Glu Gly Arg Asn Asp Met
145                 150                 155                 160

Ala Leu Lys Leu Val Gly Gly Ser His Leu Ile Ala Thr Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Leu Leu Glu Arg Ile Lys Glu Ala Asn Asp Glu
            195                 200                 205

Thr Tyr Val Glu Gln His Glu Val Ala Val Ala Arg Tyr Ser Asp Leu
            210                 215                 220

Pro Ser Lys Leu Gly His Lys Leu Asn
225                 230

<210> SEQ ID NO 24
<211> LENGTH: 233
<212> TYPE: PRT
<213> ORGANISM: Artificial Sequence
<220> FEATURE:
<223> OTHER INFORMATION: secBFP2 comprising the mutations of S28A,
      S114T, T127L, and N173H

<400> SEQUENCE: 24

Ser Glu Glu Leu Ile Lys Glu Asn Met His Met Lys Leu Tyr Met Glu
1               5                   10                  15

Gly Thr Val Asp Asn His His Phe Lys Cys Thr Ala Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Thr Leu Ile Tyr Asn Val Lys Ile Arg Gly Val Asp Phe Leu Ser
            115                 120                 125

Asn Gly Pro Val Met Gln Lys Lys Thr Leu Gly Trp Glu Ala Phe Thr
130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala His Ala Lys Thr
                165                 170                 175

Thr Tyr Arg Ser Lys Lys Pro Ala Lys Asn Leu Lys Met Pro Gly Val

```
                    180                 185                 190
Tyr Tyr Val Asp Tyr Arg Leu Glu Arg Ile Lys Glu Ala Asn Asp Glu
            195                 200                 205

Thr Tyr Val Glu Gln His Glu Val Ala Val Ala Arg Tyr Ser Asp Leu
    210                 215                 220

Pro Ser Lys Leu Gly His Lys Leu Asn
225                 230

<210> SEQ ID NO 25
<211> LENGTH: 233
<212> TYPE: PRT
<213> ORGANISM: Artificial Sequence
<220> FEATURE:
<223> OTHER INFORMATION: comprises secBFP2 comprising the mutations of
      S28A and S114T

<400> SEQUENCE: 25

Ser Glu Glu Leu Ile Lys Glu Asn Met His Met Lys Leu Tyr Met Glu
1               5                   10                  15

Gly Thr Val Asp Asn His His Phe Lys Cys Thr Ala Glu Gly Glu Gly
            20                  25                  30

Lys Pro Tyr Glu Gly Thr Gln Thr Met Arg Ile Lys Val Val Glu Gly
        35                  40                  45

Gly Pro Leu Pro Phe Ala Phe Asp Ile Leu Ala Thr Ser Phe Leu Tyr
    50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Tyr
                85                  90                  95

Glu Asp Gly Gly Val Leu Thr Ala Thr Gln Asp Thr Ser Leu Gln Asp
            100                 105                 110

Gly Thr Leu Ile Tyr Asn Val Lys Ile Arg Gly Val Asp Phe Thr Ser
        115                 120                 125

Asn Gly Pro Val Met Gln Lys Lys Thr Leu Gly Trp Glu Ala Phe Thr
130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala Asn Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
        195                 200                 205

Thr Tyr Val Glu Gln His Glu Val Ala Val Ala Arg Tyr Ser Asp Leu
    210                 215                 220

Pro Ser Lys Leu Gly His Lys Leu Asn
225                 230

<210> SEQ ID NO 26
<211> LENGTH: 233
<212> TYPE: PRT
<213> ORGANISM: Artificial Sequence
<220> FEATURE:
<223> OTHER INFORMATION: secBFP2 comprising the mutations of S28A,
      S114T, and N173H

<400> SEQUENCE: 26

Ser Glu Glu Leu Ile Lys Glu Asn Met His Met Lys Leu Tyr Met Glu
```

```
            1               5                  10                 15
Gly Thr Val Asp Asn His His Phe Lys Cys Thr Ala Glu Gly Glu Gly
                20                 25                 30
Lys Pro Tyr Glu Gly Thr Gln Thr Met Arg Ile Lys Val Val Glu Gly
                35                 40                 45
Gly Pro Leu Pro Phe Ala Phe Asp Ile Leu Ala Thr Ser Phe Leu Tyr
         50                 55                 60
Gly Ser Lys Thr Phe Ile Asp His Thr Gln Gly Ile Pro Asp Phe Phe
 65                 70                 75                 80
Lys Gln Ser Phe Pro Glu Gly Phe Thr Trp Glu Arg Val Thr Thr Tyr
                85                 90                 95
Glu Asp Gly Gly Val Leu Thr Ala Thr Gln Asp Thr Ser Leu Gln Asp
                100                105                110
Gly Thr Leu Ile Tyr Asn Val Lys Ile Arg Gly Val Asp Phe Thr Ser
                115                120                125
Asn Gly Pro Val Met Gln Lys Lys Thr Leu Gly Trp Glu Ala Phe Thr
 130                135                140
Glu Thr Leu Tyr Pro Ala Asp Gly Gly Leu Glu Gly Arg Asn Asp Met
145                 150                155                160
Ala Leu Lys Leu Val Gly Gly Ser His Leu Ile Ala His Ala Lys Thr
                165                170                175
Thr Tyr Arg Ser Lys Lys Pro Ala Lys Asn Leu Lys Met Pro Gly Val
                180                185                190
Tyr Tyr Val Asp Tyr Arg Leu Glu Arg Ile Lys Glu Ala Asn Asp Glu
                195                200                205
Thr Tyr Val Glu Gln His Glu Val Ala Val Ala Arg Tyr Ser Asp Leu
 210                215                220
Pro Ser Lys Leu Gly His Lys Leu Asn
225                 230

<210> SEQ ID NO 27
<211> LENGTH: 233
<212> TYPE: PRT
<213> ORGANISM: Artificial Sequence
<220> FEATURE:
<223> OTHER INFORMATION: secBFP2 comprising the mutations of S28A, Y96F,
      S114T, and N173H

<400> SEQUENCE: 27

Ser Glu Glu Leu Ile Lys Glu Asn Met His Met Lys Leu Tyr Met Glu
 1               5                  10                 15
Gly Thr Val Asp Asn His His Phe Lys Cys Thr Ala Glu Gly Glu Gly
                20                 25                 30
Lys Pro Tyr Glu Gly Thr Gln Thr Met Arg Ile Lys Val Val Glu Gly
                35                 40                 45
Gly Pro Leu Pro Phe Ala Phe Asp Ile Leu Ala Thr Ser Phe Leu Tyr
         50                 55                 60
Gly Ser Lys Thr Phe Ile Asp His Thr Gln Gly Ile Pro Asp Phe Phe
 65                 70                 75                 80
Lys Gln Ser Phe Pro Glu Gly Phe Thr Trp Glu Arg Val Thr Thr Phe
                85                 90                 95
Glu Asp Gly Gly Val Leu Thr Ala Thr Gln Asp Thr Ser Leu Gln Asp
                100                105                110
Gly Thr Leu Ile Tyr Asn Val Lys Ile Arg Gly Val Asp Phe Thr Ser
                115                120                125
```

```
Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala His Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
            195                 200                 205

Thr Tyr Val Glu Gln His Glu Val Ala Val Ala Arg Tyr Ser Asp Leu
    210                 215                 220

Pro Ser Lys Leu Gly His Lys Leu Asn
225                 230
```

<210> SEQ ID NO 28
<211> LENGTH: 233
<212> TYPE: PRT
<213> ORGANISM: Artificial Sequence
<220> FEATURE:
<223> OTHER INFORMATION: secBFP2 comprising the mutations of S28A, Y96F, S114T, T127L, and N173H

<400> SEQUENCE: 28

```
Ser Glu Glu Leu Ile Lys Glu Asn Met His Met Lys Leu Tyr Met Glu
1               5                   10                  15

Gly Thr Val Asp Asn His His Phe Lys Cys Thr Ala Glu Gly Glu Gly
                20                  25                  30

Lys Pro Tyr Glu Gly Thr Gln Thr Met Arg Ile Lys Val Val Glu Gly
            35                  40                  45

Gly Pro Leu Pro Phe Ala Phe Asp Ile Leu Ala Thr Ser Phe Leu Tyr
        50                  55                  60

Gly Ser Lys Thr Phe Ile Asp His Thr Gln Gly Ile Pro Asp Phe Phe
65                  70                  75                  80

Lys Gln Ser Phe Pro Glu Gly Phe Thr Trp Glu Arg Val Thr Thr Phe
                85                  90                  95

Glu Asp Gly Gly Val Leu Thr Ala Thr Gln Asp Thr Ser Leu Gln Asp
            100                 105                 110

Gly Thr Leu Ile Tyr Asn Val Lys Ile Arg Gly Val Asp Phe Leu Ser
        115                 120                 125

Asn Gly Pro Val Met Gln Lys Lys Thr Leu Gly Trp Glu Ala Phe Thr
    130                 135                 140

Glu Thr Leu Tyr Pro Ala Asp Gly Gly Leu Glu Gly Arg Asn Asp Met
145                 150                 155                 160

Ala Leu Lys Leu Val Gly Gly Ser His Leu Ile Ala His Ala Lys Thr
                165                 170                 175

Thr Tyr Arg Ser Lys Lys Pro Ala Lys Asn Leu Lys Met Pro Gly Val
            180                 185                 190

Tyr Tyr Val Asp Tyr Arg Leu Glu Arg Ile Lys Glu Ala Asn Asp Glu
            195                 200                 205

Thr Tyr Val Glu Gln His Glu Val Ala Val Ala Arg Tyr Ser Asp Leu
    210                 215                 220

Pro Ser Lys Leu Gly His Lys Leu Asn
225                 230
```